(12) United States Patent
Clifford et al.

(10) Patent No.: US 7,846,211 B2
(45) Date of Patent: Dec. 7, 2010

(54) SURGICAL IMPLANTATION METHOD AND DEVICES FOR AN EXTRA-ARTICULAR MECHANICAL ENERGY ABSORBING APPARATUS

(75) Inventors: Anton G. Clifford, Mountain View, CA (US); Mary O'Connell, Menlo Park, CA (US); Michael E. Landry, Austin, TX (US); Stefan Gabriel, Mattapoisett, MA (US)

(73) Assignee: Moximed, Inc., Hayward, CA (US)

( * ) Notice: Subject to any disclaimer, the term of this patent is extended or adjusted under 35 U.S.C. 154(b) by 53 days.

(21) Appl. No.: 12/113,157

(22) Filed: Apr. 30, 2008

(65) Prior Publication Data

US 2009/0014016 A1 Jan. 15, 2009

Related U.S. Application Data

(63) Continuation-in-part of application No. 11/775,139, filed on Jul. 9, 2007, now Pat. No. 7,611,540, and a continuation-in-part of application No. 11/775,149, filed on Jul. 9, 2007, now Pat. No. 7,655,041, and a continuation-in-part of application No. 11/775,145, filed on Jul. 9, 2007, now Pat. No. 7,678,147.

(51) Int. Cl.
*A61F 2/38* (2006.01)
*A61F 2/08* (2006.01)

(52) U.S. Cl. .................................. 623/20.21; 623/13.12
(58) Field of Classification Search .............. 623/13.13, 623/13.12, 20.21
See application file for complete search history.

(56) References Cited

U.S. PATENT DOCUMENTS 4,246,660 A * 1/1981 Wevers .................... 623/13.13
4,759,765 A 7/1988 Van Kampen
4,776,851 A * 10/1988 Bruchman et al. ........ 623/13.11
4,923,471 A 5/1990 Morgan
4,959,065 A 9/1990 Arnett et al.
4,969,895 A * 11/1990 McLeod et al. ............... 606/96
5,071,410 A * 12/1991 Pazell ..................... 604/164.01
5,318,567 A 6/1994 Vichard
5,601,553 A 2/1997 Trebling et al.
5,716,357 A 2/1998 Rogozinski (Continued)

FOREIGN PATENT DOCUMENTS

CA 1205602 6/1986

(Continued)

OTHER PUBLICATIONS

Andriacchi, Thomas P., Ph.D. et al.; "Methods for evaluating the progression of osteoarthritis"; Journal of Rehabilitation Research and Development, vol. 37, No. 2, Mar./Apr. 2000, pp. 163-170.

(Continued)

*Primary Examiner*—Bruce E Snow
*Assistant Examiner*—Melissa Hoban
(74) *Attorney, Agent, or Firm*—Steptoe & Johnson LLP

(57) ABSTRACT

A surgical implantation approach for preparing a patient and precisely and effectively placing an energy absorbing apparatus relative to the patient's anatomy. Various surgical implantation apparatus and methods for achieving proper device-to-anatomy juxtapositional relationships are employed in the implantation approach.

7 Claims, 49 Drawing Sheets

U.S. PATENT DOCUMENTS

| | | | |
|---|---|---|---|
| 6,139,550 | A | 10/2000 | Michelson |
| 6,315,852 | B1 | 11/2001 | Magrini et al. |
| 6,364,881 | B1 | 4/2002 | Apgar et al. |
| 6,692,497 | B1 | 2/2004 | Tormala et al. |
| 6,692,498 | B1 | 2/2004 | Niiranen et al. |
| 6,709,433 | B1 | 3/2004 | Schoenefeld |
| 6,884,242 | B2 | 4/2005 | LeHuec et al. |
| 6,997,940 | B2 | 2/2006 | Bonutti |
| 7,235,077 | B1 | 6/2007 | Wang et al. |
| 7,238,203 | B2 | 7/2007 | Bagga et al. |
| 7,285,134 | B2 | 10/2007 | Berry et al. |
| 2002/0151978 | A1 | 10/2002 | Zacouto et al. |
| 2003/0220643 | A1* | 11/2003 | Ferree .......................... 606/61 |
| 2005/0113927 | A1* | 5/2005 | Malek ...................... 623/17.16 |
| 2005/0251080 | A1 | 11/2005 | Hyde, Jr. |
| 2007/0244488 | A1 | 10/2007 | Metzger et al. |
| 2008/0015591 | A1 | 1/2008 | Castaneda et al. |
| 2008/0015592 | A1 | 1/2008 | Long et al. |
| 2008/0015593 | A1 | 1/2008 | Pfefferle et al. |
| 2008/0071373 | A1 | 3/2008 | Molz et al. |
| 2008/0071375 | A1 | 3/2008 | Carver et al. |
| 2008/0097434 | A1 | 4/2008 | Moumene et al. |
| 2008/0097441 | A1 | 4/2008 | Hayes et al. |
| 2008/0132954 | A1 | 6/2008 | Sekhon et al. |

FOREIGN PATENT DOCUMENTS

| | | |
|---|---|---|
| EP | 1728480 | 12/2006 |
| EP | 1770302 | 4/2007 |
| GB | 1507953 | 4/1978 |
| GB | 2250919 | 10/1993 |
| JP | 59-131348 | 7/1984 |
| JP | 7-100159 | 4/1994 |
| JP | 100159 | 4/1995 |
| JP | 2532346 | 4/1995 |
| JP | 2000-503865 | 4/2000 |
| JP | 2001-145647 | 4/2000 |
| JP | 2003-102744 | 5/2001 |
| JP | 2006-280951 | 10/2006 |
| JP | 2007-167318 | 7/2007 |
| JP | 2007-167319 | 7/2007 |
| JP | 2007-170969 | 7/2007 |
| RU | 1186204 | 10/1985 |
| RU | 1251889 | 8/1986 |
| RU | 1588404 | 8/1990 |
| RU | 2085148 | 7/1997 |
| RU | 2217105 | 11/2003 |
| RU | 2241400 | 9/2004 |
| SU | 578063 | 11/1977 |
| SU | 578957 | 11/1977 |
| SU | 624613 | 8/1978 |
| SU | 640740 | 1/1979 |
| SU | 704605 | 12/1979 |
| SU | 719612 | 3/1980 |
| SU | 741872 | 7/1980 |
| SU | 1316666 A1 | 6/1987 |
| SU | 1699441 A1 | 12/1991 |
| SU | 1769868 A1 | 10/1992 |
| WO | WO91/07137 | 5/1991 |
| WO | WO03039330 | 5/2003 |
| WO | WO2006/045091 | 4/2006 |
| WO | WO2006/049993 | 5/2006 |
| WO | WO 2007109132 | 9/2007 |
| WO | WO 2007109140 | 9/2007 |
| WO | WO 2007109436 | 9/2007 |

OTHER PUBLICATIONS

Arendt, Elizabeth, M.D.; Anatomy and Malalignment of the Patellofemoral Joint—Its Relation to Patellofemoral Arthrosis; Clinical Orthopaedics and Related Research; 2005, No. 436, pp. 71-75.

Coathup, M.J. et al.; "Osseo-mechanical induction of extra-cortical plates with reference to their surface properties and gemoetric designs", Elsevier, Biomaterials 20 (1999) 793-800.

Gunther, Klaus-Peter, M.D.; "Surgical approaches for osteoarthritis"; Best Practice & Research Clinical Rheumatology, vol. 15, No. 4, pp. 627-643, 2001.

Leon, Heriberto Ojeda, M.D. et al.; "Minimally Invasive Selective Osteotomy of the Knee: A New Surgical Technique"; Arthroscopy: The Journal of Arthroscopic and Related Surgery, vol. 17, No. 5 (May-Jun.), 2001: pp. 510-516.

Pilliar et al., Bone Ingrowth and Stress Shielding with a Porous Surface Coated Fracture Fixation Plate, Journal of Biomedical Materials Research, vol. 13, 799-810 (1979).

Pollo, Fabian E. et al.; "Reduction of Medial Compartment Loads With Valgus Bracing of the Osteoarthritic Knee"; American Journal Sports Medicine, vol. 30, No. 3, 2002; pp. 414-421.

Repicci, John A., M.D. et al. "Minimally invasive unicondylar knee arthroplasty for the treatment of unicompartmental osteoarthritis: an outpatient arthritic bypass procedure"; Orthopedic Clinics of North America, 35 (2004), pp. 201-216.

Sharma, Leena et al.; "The Mechanism of the Effect of Obesity in Knee Osteoarthritis-The Mediating Role of Malalignment"; Arthritis & Rheumatism, vol. 43, No. 3, Mar. 2000, pp. 568-575.

Sharma, Leena, M.D. et al.; "The Role of Knee Alignment in Disease Progression and Functional Decline in Knee Osteoarthritis"; JAMA, Jul. 11, 2001, vol. 286, No. 2, pp. 188-196.

Van Der Esch, M. et al.; "Structural joint changes, malalignment, and laxity in osteoarthritis of the knee"; Scand J Rheumatol 2005; 34:298-301.

Lapinskaya, Valentina Spiridonovna, "Treatment of Diseases and Injuries of Hip Joint Using a Method of Distraction", Kuibyshev Medical Institute, 1990.

Larionov d. Yu, et al., "Medical Devices", Scientific and Technical Bimonthly Journal, May-Jun. 2008.

PCT search report dated Dec. 8, 2009 from PCT application No. PCT/US2009/002722 as issued by the European Patent Office as searching authority.

Lapinskaya, V.S., et al., "An Endoapparatus For Restoration of the Hip Joint", Writers Collective, 2008, UDK 615.472.03:616.728.2-089.28.

Lentsner, A.A., et al., "Device For Functional Relief of Hip Joint in Cotyloid Cavity Fracture Cases", Ortop Travmatol Protez. Apr. 1990 (4) 44-6.

* cited by examiner

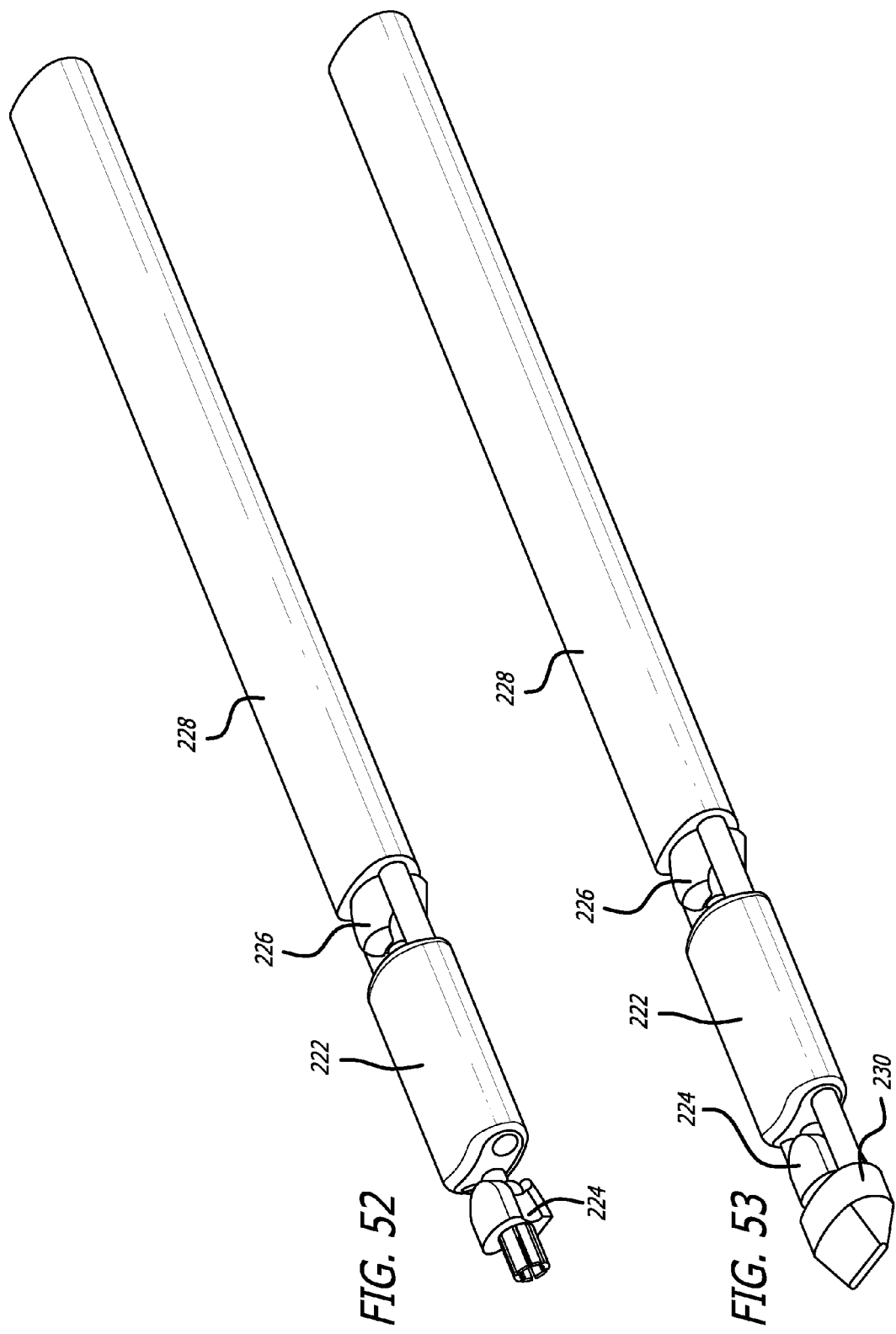

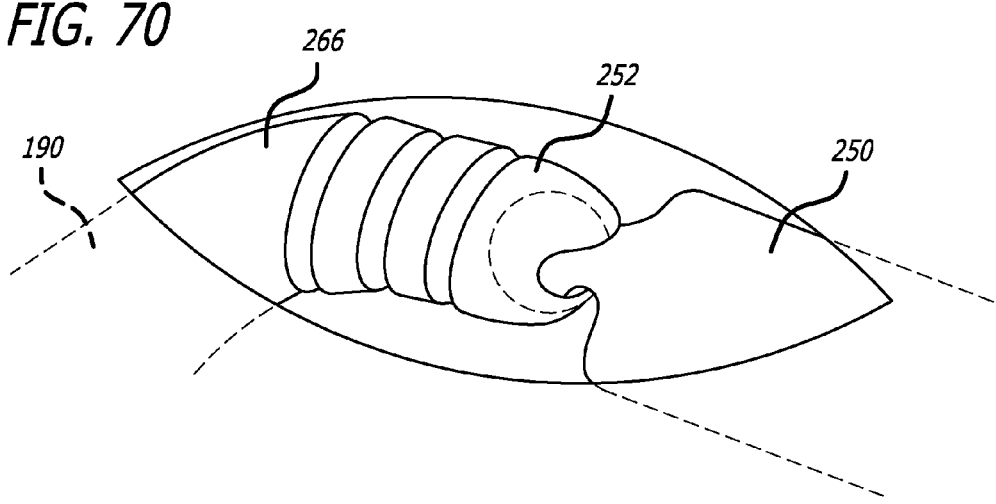
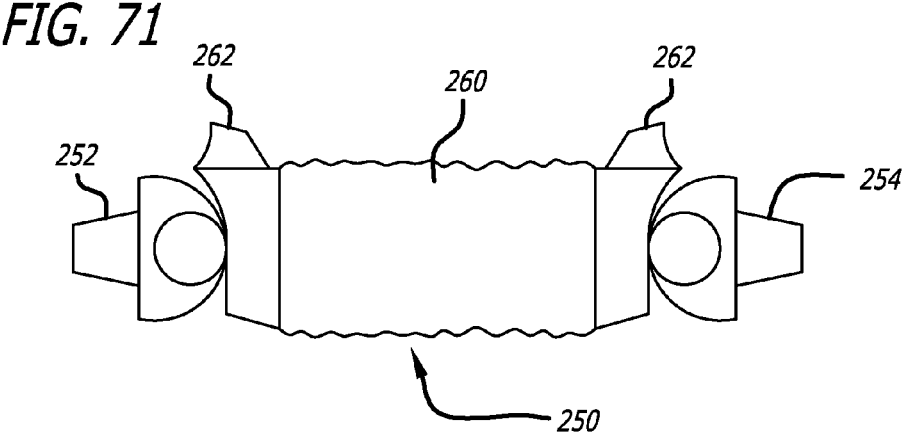
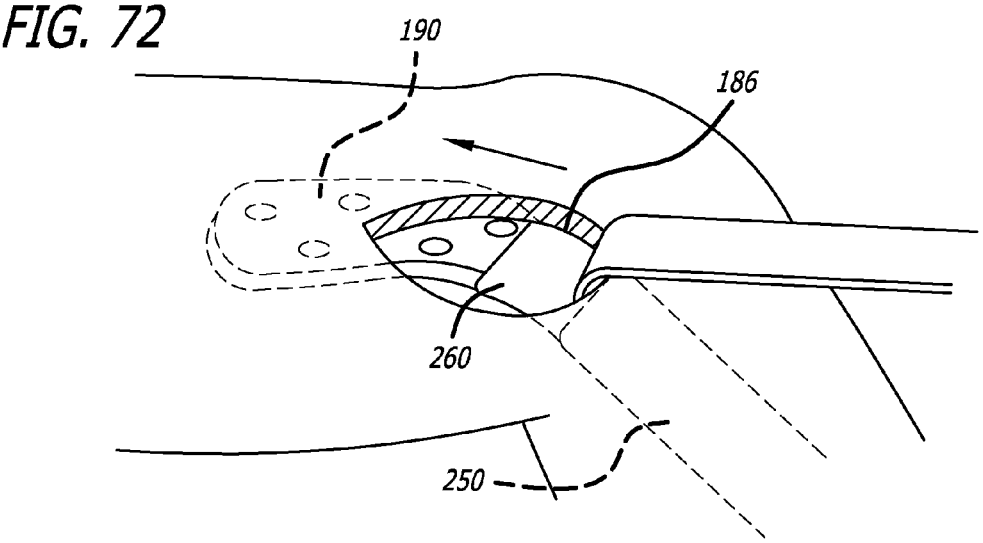

SURGICAL IMPLANTATION METHOD AND DEVICES FOR AN EXTRA-ARTICULAR MECHANICAL ENERGY ABSORBING APPARATUS

CROSS REFERENCE TO RELATED APPLICATIONS

This application is a continuation-in-part of U.S. application Ser. No. 11/775,139, filed Jul. 9, 2007 now U.S. Pat. No. 7,611,540, a continuation-in-part of U.S. application Ser. No. 11/775,149, filed Jul. 9, 2007 now U.S. Pat. No. 7,655,041 and a continuation-in-part of U.S. application Ser. No. 11/775,145, filed Jul. 9, 2007 now U.S. Pat. No. 7,678,147, the entire disclosures of which are expressly incorporated herein by reference.

BACKGROUND

The present disclosure is directed towards methods for treating tissue of a body and more particularly, towards procedures and devices for implanting an extra-articular mechanical energy absorbing apparatus.

Both humans and other mammals belong to the subphylum known as vertebrata. The defining characteristic of a vertebrate is considered the backbone or spinal cord, a brain case, and an internal skeleton. In biology, the skeleton or skeletal system is the biological system providing physical support in living organisms. Skeletal systems are commonly divided into three types—external (an exoskeleton), internal (an endoskeleton), and fluid based (a hydrostatic skeleton).

An internal skeletal system consists of rigid (or semi-rigid) structures, within the body, moved by the muscular system. If the structures are mineralized or ossified, as they are in humans and other mammals, they are referred to as bones. Cartilage is another common component of skeletal systems, supporting and supplementing the skeleton. The human ear and nose are shaped by cartilage. Some organisms have a skeleton consisting entirely of cartilage and without any calcified bones at all, for example sharks. The bones or other rigid structures are connected by ligaments and connected to the muscular system via tendons.

A joint is the location at which two or more bones make contact. They are constructed to allow movement and provide mechanical support, and are classified structurally and functionally. Structural classification is determined by how the bones connected to each other, while functional classification is determined by the degree of movement between the articulating bones. In practice, there is significant overlap between the two types of classifications.

There are three structural classifications of joints, namely fibrous or immovable joints, cartilaginous joints and synovial joints. Fibrous/Immovable bones are connected by dense connective tissue, consisting mainly of collagen. The fibrous joints are further divided into three types:

sutures which are found between bones of the skull;
syndesmosis which are found between long bones of the body; and
gomphosis which is a joint between the root of a tooth and the sockets in the maxilla or mandible.

Cartilaginous bones are connected entirely by cartilage (also known as "synchondroses"). Cartilaginous joints allow more movement between bones than a fibrous joint but less than the highly mobile synovial joint. Synovial joints have a space between the articulating bones for synovial fluid. This classification contains joints that are the most mobile of the three, and includes the knee and shoulder. These are further classified into ball and socket joints, condyloid joints, saddle joints, hinge joints, center of rotation joints, and gliding joints.

Joints can also be classified functionally, by the degree of mobility they allow. Synarthrosis joints permit little or no mobility. They can be categorized by how the two bones are joined together. That is, synchrondoses are joints where the two bones are connected by a piece of cartilage. Synostoses are where two bones that are initially separated eventually fuse together as a child approaches adulthood. By contrast, amphiarthrosis joints permit slight mobility. The two bone surfaces at the joint are both covered in hyaline cartilage and joined by strands of fibrocartilage. Most amphiarthrosis joints are cartilaginous.

Finally, diarthrosis joints permit a variety of movements (e.g. flexion, adduction, pronation). Only synovial joints are diarthrodial and they can be divided into six classes: 1. ball and socket—such as the shoulder or the hip and femur; 2. hinge—such as the elbow; 3. center of rotation—such as the radius and ulna; 4. condyloidal (or ellipsoidal)—such as the wrist between radius and carps, or knee; 5. saddle—such as the joint between carpal thumbs and metacarpals; and 6. gliding—such as between the carpals.

Synovial joints (or diarthroses, or diarthroidal joints) are the most common and most moveable type of joints in the body. As with all other joints in the body, synovial joints achieve movement at the point of contact of the articulating bones. Structural and functional differences distinguish the synovial joints from the two other types of joints in the body, with the main structural difference being the existence of a cavity between the articulating bones and the occupation of a fluid in that cavity which aids movement. The whole of a diarthrosis is contained by a ligamentous sac, the joint capsule or articular capsule. The surfaces of the two bones at the joint are covered in cartilage. The thickness of the cartilage varies with each joint, and sometimes may be of uneven thickness. Articular cartilage is multi-layered. A thin superficial layer provides a smooth surface for the two bones to slide against each other. Of all the layers, it has the highest concentration of collagen and the lowest concentration of proteoglycans, making it very resistant to shear stresses. Deeper than that is an intermediate layer, which is mechanically designed to absorb shocks and distribute the load efficiently. The deepest layer is highly calcified, and anchors the articular cartilage to the bone. In joints where the two surfaces do not fit snugly together, a meniscus or multiple folds of fibro-cartilage within the joint correct the fit, ensuring stability and the optimal distribution of load forces. The synovium is a membrane that covers all the non-cartilaginous surfaces within the joint capsule. It secretes synovial fluid into the joint, which nourishes and lubricates the articular cartilage. The synovium is separated from the capsule by a layer of cellular tissue that contains blood vessels and nerves.

Cartilage is a type of dense connective tissue and as shown above, it forms a critical part of the functionality of a body joint. It is composed of collagenous fibers and/or elastin fibers, and cells called chondrocytes, all of which are embedded in a firm gel-like ground substance called the matrix. Articular cartilage is avascular (contains no blood vessels) and nutrients are diffused through the matrix. Cartilage serves several functions, including providing a framework upon which bone deposition can begin and supplying smooth surfaces for the movement of articulating bones. Cartilage is found in many places in the body including the joints, the rib cage, the ear, the nose, the bronchial tubes and between intervertebral discs. There are three main types of cartilage: hyaline, elastic and fibrocartilage.

Chondrocytes are the only cells found in cartilage. They produce and maintain the cartilaginous matrix. Experimental evidence indicates that cells are sensitive to their mechanical (stress-strain) state, and react directly to mechanical stimuli. The biosynthetic response of chondrocytes was found to be sensitive to the frequency and amplitude of loading (Wong et al., 1999 and Kurz et al., 2001). Recent experimental studies further indicate that excessive, repetitive loading may induce cell death, and cause morphological and cellular damage, as seen in degenerative joint disease (Lucchinetti et al., 2002 and Sauerland et al., 2003). Islam et al. (2002) found that continuous cyclic hydrostatic pressure (5 MPa, 1 Hz for 4 hours) induced apoptosis in human chondrocytes derived from osteoarthritic cartilage in vitro. In contrast, cyclic, physiological-like loading was found to trigger a partial recovery of morphological and ultra-structural aspects in osteoarthritic human articular chondrocytes (Nerucci et al., 1999).

Cancellous bone (also known as trabecular, or spongy) is a type of osseous tissue which also forms an important aspect of a body joint. Cancellous bone has a low density and strength but very high surface area, that fills the inner cavity of long bones. The external layer of cancellous bone contains red bone marrow where the production of blood cellular components (known as hematopoiesis) takes place. Cancellous bone is also where most of the arteries and veins of bone organs are found. The second type of osseous tissue is known as cortical bone, forming the hard outer layer of bone organs.

Various maladies can affect the joints, one of which is arthritis. Arthritis is a group of conditions where there is damage caused to the joints of the body. Arthritis is the leading cause of disability in people over the age of 65.

There are many forms of arthritis, each of which has a different cause. Rheumatoid arthritis and psoriatic arthritis are autoimmune diseases in which the body is attacking itself. Septic arthritis is caused by joint infection. Gouty arthritis is caused by deposition of uric acid crystals in the joint that results in subsequent inflammation. The most common form of arthritis, osteoarthritis is also known as degenerative joint disease and occurs following trauma to the joint, following an infection of the joint or simply as a result of aging.

Unfortunately, all arthritides feature pain. Patterns of pain differ among the arthritides and the location. Rheumatoid arthritis is generally worse in the morning; in the early stages, patients often do not have symptoms following their morning shower.

Osteoarthritis (OA, also known as degenerative arthritis or degenerative joint disease, and sometimes referred to as "arthrosis" or "osteoarthrosis" or in more colloquial terms "wear and tear"), is a condition in which low-grade inflammation results in pain in the joints, caused by wearing of the cartilage that covers and acts as a cushion inside joints. As the bone surfaces become less well protected by cartilage, the patient experiences pain upon weight bearing, including walking and standing. Due to decreased movement because of the pain, regional muscles may atrophy, and ligaments may become more lax. OA is the most common form of arthritis.

The main symptoms of osteoarthritis is chronic pain, causing loss of mobility and often stiffness. "Pain" is generally described as a sharp ache, or a burning sensation in the associated muscles and tendons. OA can cause a crackling noise (called "crepitus") when the affected joint is moved or touched, and patients may experience muscle spasm and contractions in the tendons. Occasionally, the joints may also be filled with fluid. Humid weather increases the pain in many patients.

OA commonly affects the hand, feet, spine, and the large weight-bearing joints, such as the hips and knees, although in theory, any joint in the body can be affected. As OA progresses, the affected joints appear larger, are stiff and painful, and usually feel worse, the more they are used and loaded throughout the day, thus distinguishing it from rheumatoid arthritis. With progression in OA, cartilage looses its viscoelastic properties and it's ability to absorb load.

Generally speaking, the process of clinical detectable osteoarthritis is irreversible, and typical treatment consists of medication or other interventions that can reduce the pain of OA and thereby improve the function of the joint. According to an article entitled *Surgical approaches for osteoarthritis* by Klaus-Peter Günther, MD, over recent decades, a variety of surgical procedures have been developed with the aim of decreasing or eliminating pain and improving function in patients with advanced osteoarthritis (OA). The different approaches include preservation or restoration of articular surfaces, total joint replacement with artificial implants, and arthrodeses.

Arthrodeses are described as being reasonable alternatives for treating OA of small hand and foot joints as well as degenerative disorders of the spine, but were deemed to be rarely indicated in large weight-bearing joints such as the knee due to functional impairment of gait, cosmetic problems and further side-effects. Total joint replacement was characterized as an extremely effective treatment for severe joint disease. Moreover, recently developed joint-preserving treatment modalities were identified as having a potential to stimulate the formation of a new articular surface in the future. However, it was concluded that such techniques do not presently predictably restore a durable articular surface to an osteoarthritic joint. Thus, the correction of mechanical abnormalities by osteotomy and joint debridement are still considered as treatment options in many patients. Moreover, patients with limb malalignment, instability and intra-articular causes of mechanical dysfunction can benefit from an osteotomy to provide pain relief. The goal being the transfer of weight-bearing forces from arthritic portions to healthier locations of a joint.

Joint replacement is one of the most common and successful operations in modern orthopaedic surgery. It consists of replacing painful, arthritic, worn or diseased parts of the joint with artificial surfaces shaped in such a way as to allow joint movement. Such procedures are a last resort treatment as they are highly invasive and require substantial periods of recovery. Joint replacement sometimes called total joint replacement indicating that all joint surfaces are replaced. This contrasts with hemiarthroplasty (half arthroplasty) in which only one bone's joint surface is replaced and unincompartmental arthroplasty in which both surfaces of the knee, for example, are replaced but only on the inner or outer sides, not both. Thus, arthroplasty as a general term, is an operative procedure of orthopaedic surgery performed, in which the arthritic or dysfunctional joint surface is replaced with something better or by remodeling or realigning the joint by osteotomy or some other procedure. These procedures are also characterized by relatively long recovery times and their highly invasive procedures. The currently available therapies are not condroprotective. Previously, a popular form of arthroplasty was interpositional arthroplasty with interposition of some other tissue like skin, muscle or tendon to keep inflammatory surfaces apart or excisional arthroplasty in which the joint surface and bone was removed leaving scar tissue to fill in the gap. Other forms of arthroplasty include resection(al) arthroplasty, resurfacing arthroplasty, mold arthroplasty, cup arthroplasty, silicone replacement arthroplasty, etc. Osteotomy to restore or modify joint congruity is also an arthroplasty.

Osteotomy is a related surgical procedure involving cutting of bone to improve alignment. The goal of osteotomy is to relieve pain by equalizing forces across the joint as well as increase the lifespan of the joint. This procedure is often used in younger, more active or heavier patients. High tibial osteotomy (HTO) is associated with a decrease in pain and improved function. However, HTO does not address ligamentous instability—only mechanical alignment. HTO is associated with good early results, but results deteriorate over time.

Other approaches to treating osteoarthritis involve an analysis of loads which exist at a joint. Both cartilage and bone are living tissues that respond and adapt to the loads they experience. If a joint surface remains unloaded for appreciable periods of time the cartilage tends to soften and weaken. Further, as with most materials that experience structural loads, particularly cyclic structural loads, both bone and cartilage begin to show signs of failure at loads that are below their ultimate strength. However, cartilage and bone have some ability to repair themselves. There is also a level of load at which the skeleton will fail catastrophically. Accordingly, it has been concluded that the treatment of osteoarthritis and other conditions is severely hampered when a surgeon is not able to precisely control and prescribe the levels of joint load. Furthermore, bone healing research has shown that some mechanical stimulation can enhance the healing response and it is likely that the optimum regime for a cartilage/bone graft or construct will involve different levels of load over time, e.g. during a particular treatment schedule. Thus, there has been identified a need for devices which facilitate the control of load on a joint undergoing treatment or therapy, to thereby enable use of the joint within a healthy loading zone.

Certain other approaches to treating osteoarthritis contemplate external devices such as braces or fixators which control the motion of the bones at a joint or apply cross-loads at a joint to shift load from one side of the joint to the other. Various of these approaches have had some success in alleviating pain but suffer from patient compliance or lack an ability to facilitate and support the natural motion and function of the diseased joint. Notably, the motion of bones forming a joint can be as distinctive as a finger print, and thus, each individual has his or her own unique set of problems to address. Therefore, mechanical approaches to treating osteoarthritis have had limited applications.

Prior approaches to treating osteoarthritis have also been remiss in acknowledging all of the basic functions of the various structures of a joint in combination with its unique movement. That is, in addition to addressing loads at a joint and joint movement, there has not been an approach which also acknowledges the dampening and energy absorption functions of the anatomy, and taking a minimally invasive approach in implementing solutions. Prior devices designed to reduce the load transferred by the natural joint typically describe rigid body systems that are incompressible. Mechanical energy is the product of force (F) and displacement distance (s) of a given mass (i.e., E=Fxs, for a given mass M). These systems have zero displacement within their working body (s=0). Since there is no displacement within the device it is reasonable to say that there is no energy storage or absorption in the device. Such devices act to transfer and not absorb energy from the joint. By contrast the natural joint is not a rigid body but is comprised of elements of different compliance characteristics such as bone, cartilage, synovial fluid, muscles, tendons, ligaments, etc. as described above. These dynamic elements act to both transfer and absorb energy about the joint. For example cartilage compresses under applied force and therefore the resultant force displacement product represents the energy absorbed by cartilage. In addition cartilage has a non linear force displacement behavior and is considered viscoelastic. Such systems not only absorb and store, but additionally act to dissipate energy.

Approaches for surgically implanting extra-articular mechanical energy absorbing apparatus have been developed. As precise and effective placement are critical to the efficacy of an implanted extra-articular mechanical absorbing apparatus, further advancements in patient preparation and device-to-anatomy juxapositional relationships have been found to be both useful and necessary.

Therefore, what is needed are further refinements and other approaches to properly and effectively implant energy absorbing apparatus.

The present invention satisfies these and other needs.

SUMMARY OF THE DISCLOSURE

Briefly and in general terms, the present disclosure is directed towards a surgical procedure for implanting a medical device. More particularly, the procedure involves placement of an extra-articular mechanical energy absorbing apparatus across anatomy being treated. In one aspect, the energy absorbing apparatus is placed across an articulating joint.

In one embodiment, the contemplated approach involves one or more of patient preparation, identification of device position relative to anatomy, structure of proper device components and device implantation. Various devices and implantation aids are disclosed to accomplish effective and proper placement of a medical device.

In one contemplated approach, the position of the patient and treatment areas are selected for easy access and to achieve proper alignment at an implantation site. Use of vacuum lock supports and arch bed structure accomplishes desired treatment site stabilization and orientation. An adjustable surgical table also facilitates desired positioning.

Moreover, in various contemplated approaches, guide structures are configured adjacent a treatment site to aid in identifying a proper juxtapositional relationship between patient body anatomy and mechanical energy absorbing apparatus. In one particular aspect, guide structures can be embodied in a multi-directional center of rotation locator configured to identify a center of rotation of an articulating limb. Further, remote visualization as well as templates are contemplated for use in both identifying device-to-anatomy mounting locations as well as incision sites. Further, anatomical references can be used to locate the center of rotation, and the target location can be manually positioned by referencing these anatomical references.

In further contemplated approaches, proper size and configuration of components of the mechanical energy absorbing apparatus involves understanding the anatomy of the treatment area as well as the unique characteristics of the anatomy of the patient. When the energy absorbing apparatus includes one or more bases which are to be fixed to a bone, such bases are selected to provide surfaces which approximate the bone to which it is to be attached and includes desired separation from the bone to provide connecting structure. In this regard, remote sizing devices and a direct physical inspection of the anatomy is undertaken. Furthermore, fixed distance links, dummy links and base locating tools are employed to facilitate both selection of base implantation sites and proper component identification.

Assemblies for preparing bone mount sites and providing access thereto are used in contemplated implantable procedures. Structure in the form of base trials are used to identify and initiate device mounting and act as drill guides. Also, tools are provided to connect various components of an energy absorbing apparatus at the treatment site. Kirscher wires (K-wires) and Steinmann pins are employed to help maintain alignment of components within the interventional site. In the art, "Kirscher wire" or "K-wire" is generally used to refer to wires up to 2 mm in diameter. "Steinmann pin" is generally used to refer to wires above 2 mm in diameter. For the purpose of this application, the term "K-wire" is used generically to cover both Kirscher wires and Steinmann pins. Both compression and locking screws are contemplated for fixation purposes.

Moreover, an elongated handle with a distal attachment to a component of an energy absorbing apparatus is contemplated to form a tunnel or other access area at an interventional site as well as to deliver components thereto. Devices and approaches are also contemplated for advancing components through the tunnel formed below a patient's skin and for both temporary fixation and permanent assembly of parts. Post-implanted and post operative examination is also contemplated to ensure proper operation of the mechanical absorbing device.

The mechanical energy absorbing apparatus has the capacity to absorb energy in addition to transfer energy from the joint. Various joints of the body can be treated employing the systems and methods of the present invention. In particular, articulating bones involved in synovial joints can benefit from the present invention. Accordingly, there are contemplated applications to the joints in the knee, ankle, shoulder, hip, hand, wrist, elbow, mandible, and foot.

In one specific embodiment, the presently disclosed apparatus is embodied in a device utilizing an element, or elements functioning as a unit, which responds to bending or changes in elongation. Further, the device is used to reduce the loading experienced by the articular surfaces of the tibiofemoral joint. In one embodiment, the device is designed to reduce load on the joint during knee extension with energy absorption. Joint load reduction in this phase is governed by the compression of the device—increased compression yields greater joint reduction. The device is anchored in a position which ensures device elongation resulting from knee flexion. As the knee moves into flexion, the device is un-compressed and will cause little to no joint load changes. The device may have other features which ensure correct device alignment, and prevent against buckling, as the device transitions into a compressed state. The device can also be configured to provide joint load reductions during flexion or throughout the nearly full range of motion.

Other features of the present disclosure will become apparent from the following detailed description, taken in conjunction with the accompanying drawings, which illustrate, by way of example, the principles of the approach.

BRIEF DESCRIPTION OF THE DRAWINGS

FIG. 52 is a perspective view, depicting the fixed distance link of FIG. 51 attached to a distal end of a handle assembly;

FIG. 53 is a perspective view, depicting the arrangement of FIG. 52 further including a cover installed on a distal end of the fixed distance link;

FIG. 70 is an enlarged view, depicting a connection between a link assembly and a base component;

FIG. 71 is a side view, depicting a link assembly including socket locks;

FIG. 72 is a partial cross-sectional view, depicting configuring a portion of a sheath about a portion of a first base component;

DETAILED DESCRIPTION

Figure 1:
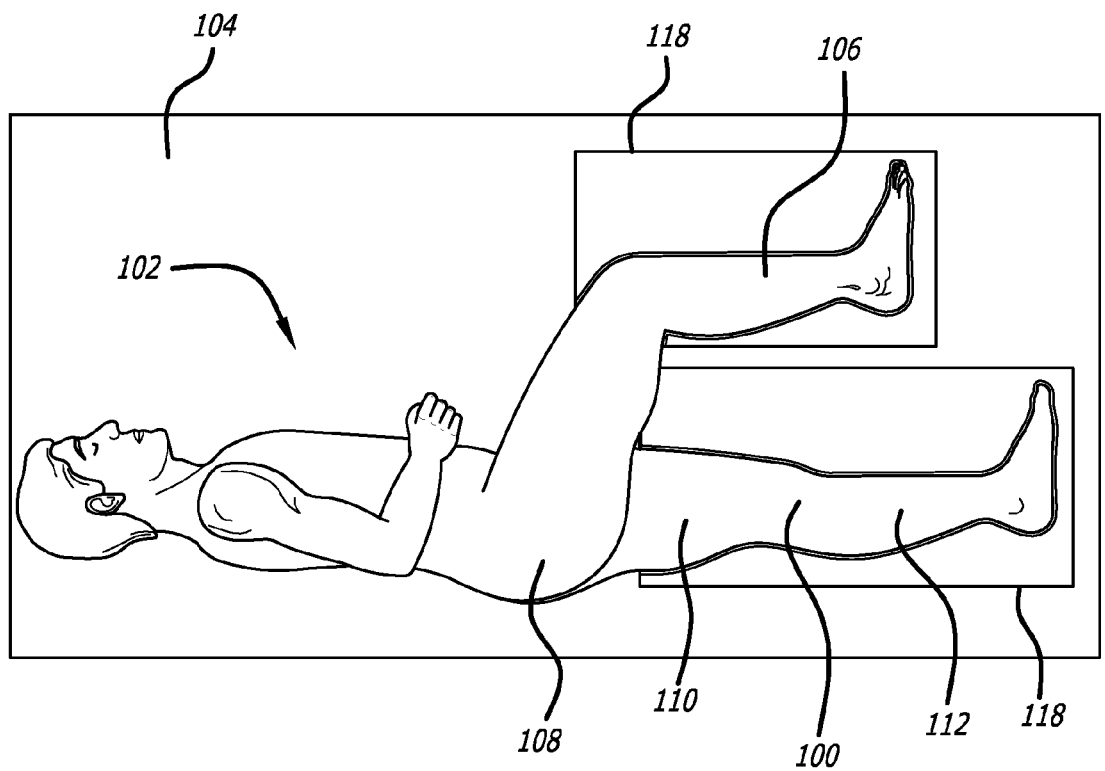
FIG. 1 is a perspective view, depicting a patient position for an interventional procedure.

Referring now to the drawings, which are provided by way of example and not limitation, the present disclosure is directed towards apparatus for treating body tissues. In applications relating to the treatment of body joints, the described approach seeks to alleviate pain associated with the function of diseased or malaligned members forming a body joint. Whereas the present invention is particularly suited to address issues associated with osteoarthritis, the energy manipulation accomplished by the present invention lends itself well to broader applications. Moreover, the present invention is particularly suited to treating synovial joints such as the knee, finger, wrist, ankle and shoulder.

In one particular aspect, the presently disclosed method seeks to permit and complement the unique articulating motion of the members defining a body joint of a patient while simultaneously manipulating energy being experienced by both cartilage and osseous tissue (cancellous and cortical bone). Approaches involving varying energy absorption and transfer during the rotation of the joint and selecting a geometry for the energy absorption assembly to provide necessary flexibility are implemented into various embodiments of the present invention. Certain of the embodiments include geometry which accomplishes variable energy absorption designed to minimize and complement the dampening effect and energy absorption provided by the anatomy of the body, such as that found at a body joint. It has been postulated that to minimize pain, in an osteoarthritic joint absorption of 1-40% of forces, in varying degrees, may be necessary. Variable absorption in the range of 5-20% can be a target for certain applications. In certain specific applications, temporary distraction (e.g., less than 3 months) is employed in the energy manipulation approach.

Conventional or surgical or minimally invasive approaches are taken to gain access to a body joint or other anatomy requiring attention. Arthroscopic approaches are thus contemplated when reasonable to both implant the energy manipulation assembly as well as to accomplish adjusting an implanted assembly. Moreover, biologically inert materials of various kinds can be employed in constructing the energy manipulation assemblies of the present invention.

In one approach for treating a knee, an implantable extra-articular absorber is designed to reduce medial compartment loads of the knee. The absorber system is comprised of two contoured base components, a kinematic load absorber and a set of bone screws. The implanted system is both extra articular and extra capsular and resides in the subcutaneous tissue on the medial aspect of the knee. The device is inserted through two small incisions superior to the medial femoral condyle and inferior to the tibial plateau. The contoured base components are fixed to the medial cortices of the femur and tibia using bone screws.

The femoral and tibial base components are contoured to ensure optimal fit to the bony surfaces and are plasma sprayed and coated with hydroxyapatite on bone contacting surfaces to promote bony ingrowth and enhance osteointegration. The orthopedic bone screws provide immediate fixation of the base components to the bone during osteointegration.

The kinematic absorber is attached to the base components between two mobile ball and socket joints. It is comprised of two helically wound springs on a sliding stabilizer. The springs act to absorb load from the medial compartment of the knee while the sliding stabilizer and the ball/sockets allow the device to accommodate full knee range of motion.

The load bypassing knee support system is indicated for patients suffering with medial knee pain secondary to osteoarthritis who have failed medical treatments.

It is contemplated that the absorber system is supplied packaged in a set of individually sealed Tyvek/film pouches. The base components and absorber assemblies will each be individually packaged and labeled. Moreover, the load bypassing knee support system and all its components are provided sterile and are not intended for reuse/re-sterilization by the user. These devices are sterilized using EtO. Surgical instruments, positioning and locking instruments must be sterilized using normal hospital orthopedic instrument sterilization methods.

Figure 1A:
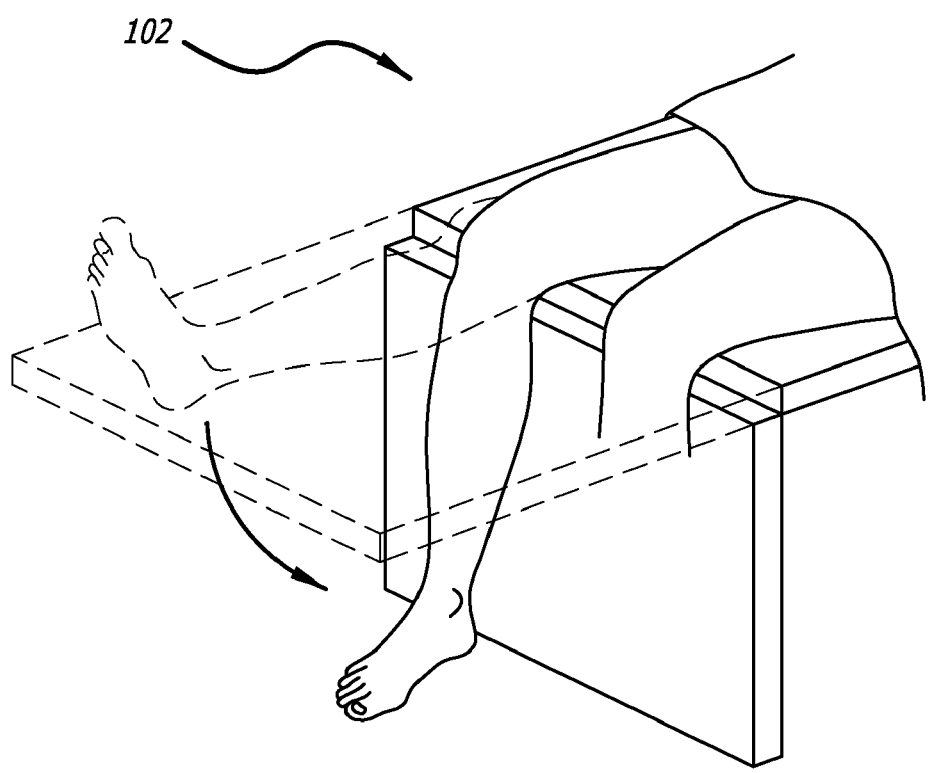
FIG. 1A is a perspective view, depicting an alternative positioning for a patient.
Figure 2:
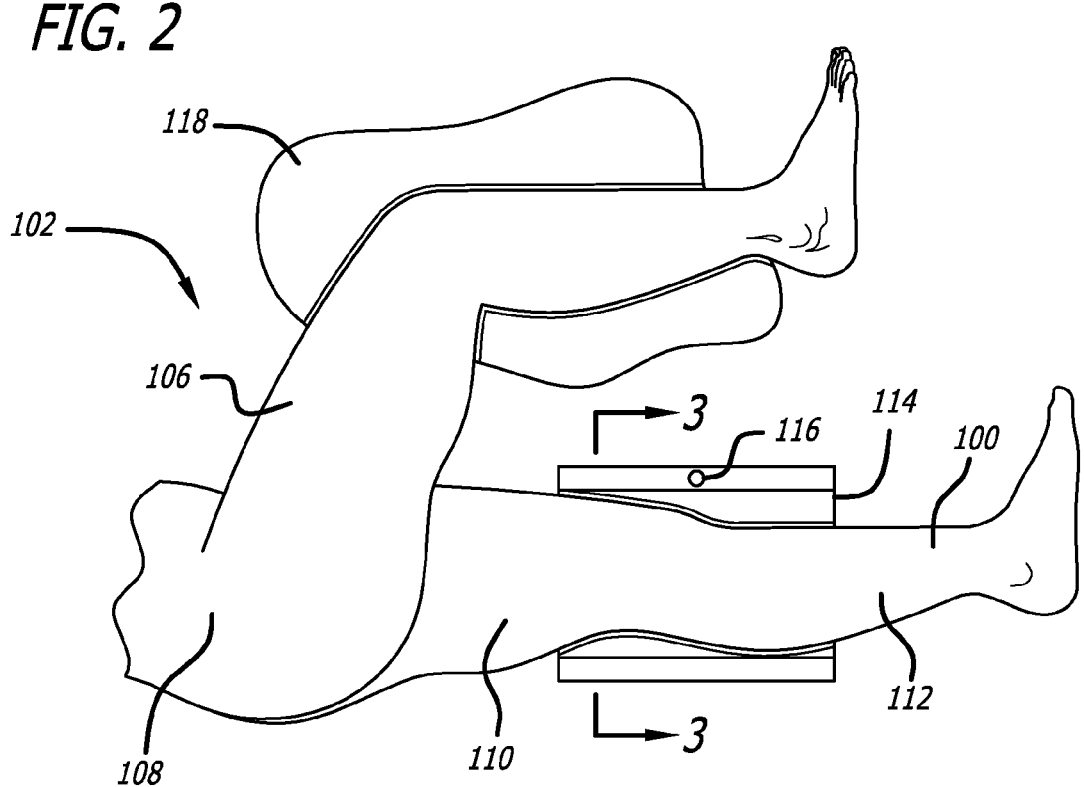
FIG. 2 is a perspective view, depicting an alternate approach for securing a limb of a patient.
Figure 3:
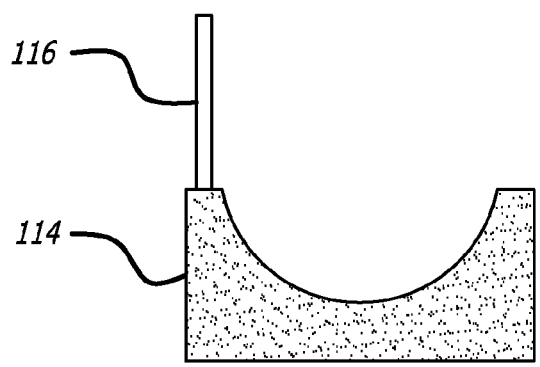
FIG. 3 is a cross-sectional view taken along lines 3-3, depicting apparatus of FIG. 2.

In one particular approach, turning now to FIGS. 1-5, there are shown various apparatus for positioning a patient and preparing the patient for an interventional procedure. Although the disclosed apparatus can be configured for use in various procedures, for purposes of illustration, the apparatus have been depicted in conjunction with treatment of a leg 100 of a patient 102. For such a procedure, the patient 102 is placed upon a surgical table 104 in a lateral decubitus position with the patient 102 laying generally on his or her side as shown in FIG. 1. Alternatively, depending on surgeon preference, the patient can be placed in a supine position with an ability to flex the knee (See FIG. 1A).

While in a lateral decubitus position, a top leg 106 of the patient 102 is flexed forward at the hip 108. A medial side 110 of the bottom leg 112 is exposed and in full extension. Fluoroscopic imagery is utilized to ensure that the knee is in full extension and in a true lateral position. The operating table may be airplaned and/or moved into slight trendelenberg or reverse trendelenberg to assist in obtaining and maintaining true lateral knee fluoroscopy. Any gap between the medial condyles of the articulating bone structure of the leg is closed by supporting a lateral side of the distal tibia of the bottom leg 112. In this regard, an arch bed 114 can be provided to help properly align the bottom leg 112. The arch bed 114 can further include a post 116 to which interventional tools can be mounted.

The patient and limb can be stabilized with a bean bag or peg board per physician preference. Moreover, the upper leg 106 can be supported by a vacuum lock support 118. The vacuum lock support 118 can be configured to assume a desired shape and subsequently be locked into the desired shape during the interventional procedure. The vacuum lock support 118 structure can also be employed to support other areas of the patient including the lower leg 100 as shown in FIG. 1. Where such structure is utilized, a femoral side of the lower leg 100 should be locked throughout the procedure, whereas the tibial side should be able to be locked and unlocked to allow for rotation. Various angulations of the limbs are necessary during tibial base component fixation and full flexion knee motions must be available.

Figure 4:
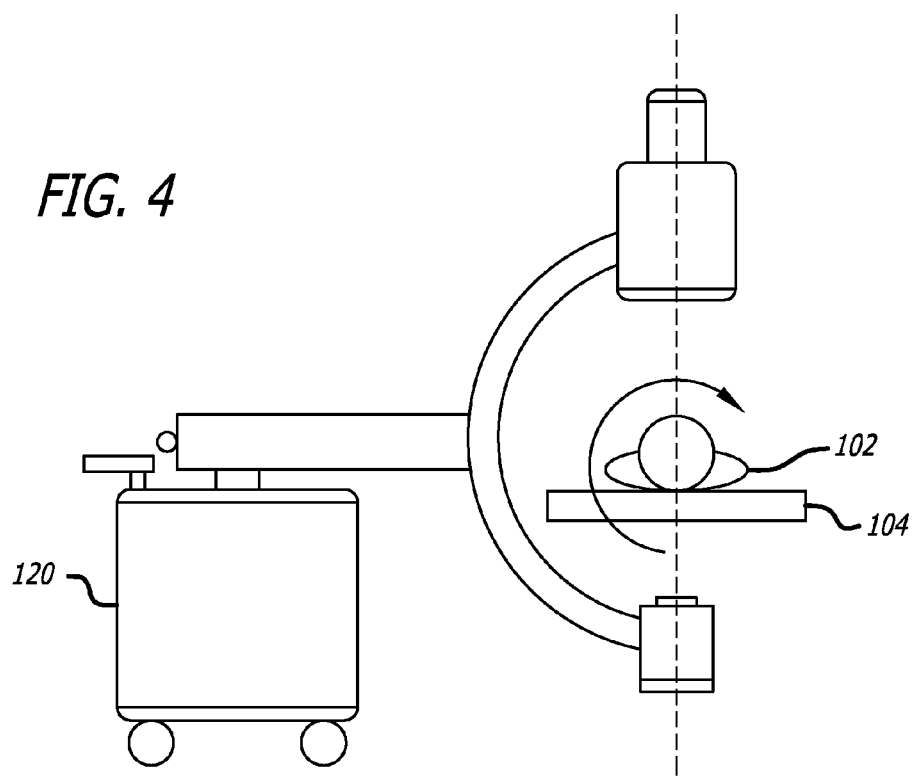
FIG. 4 is a top view, depicting a patient on a surgical platform.
Figure 5:
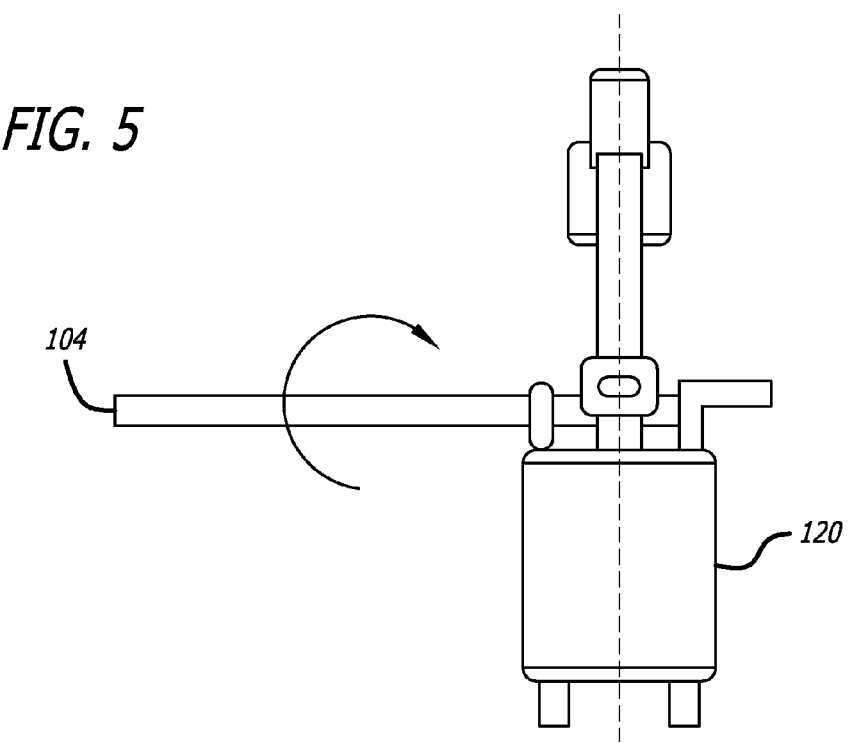
FIG. 5 is a side view, depicting further control of the device shown in FIG. 4.

Once the limbs of the patient are properly positioned, the interventional area is cleaned and shaved as necessary. The entire leg, thigh through foot should be prepared. Under fluoroscopy or other remote imaging means 120, femoral condyles (not shown) are aligned by pivoting the table 104 with table adjustment controls and to again ensure a true lateral view. As shown in FIGS. 4 and 5, the table 104 can be rotated laterally to align posterior condyles and can be rotated longitudinally to align inferior condyles. When necessary, the table 104 can also be rotated along a third axis of rotation to achieve proper leg position-to-remote viewing orientation. Alternatively, the fluoroscopy can be rotated to ensure a true lateral view.

During the interventional procedure, the operative articulating knee joint and foot of the patient 102 should be completely exposed and configured outside a drape covering the patient 102. The knee should be free to flex and extend as needed and preferably up to 135° of flexion. Again, any medial condyle gap should be closed by supporting the lateral side of the distal tibia and/or ankle. Once the physician is satisfied with leg positioning and preparation, using palpation to define bone position, tibia and femur base contours are traced onto the skin with a surgical marker.

Figure 6:
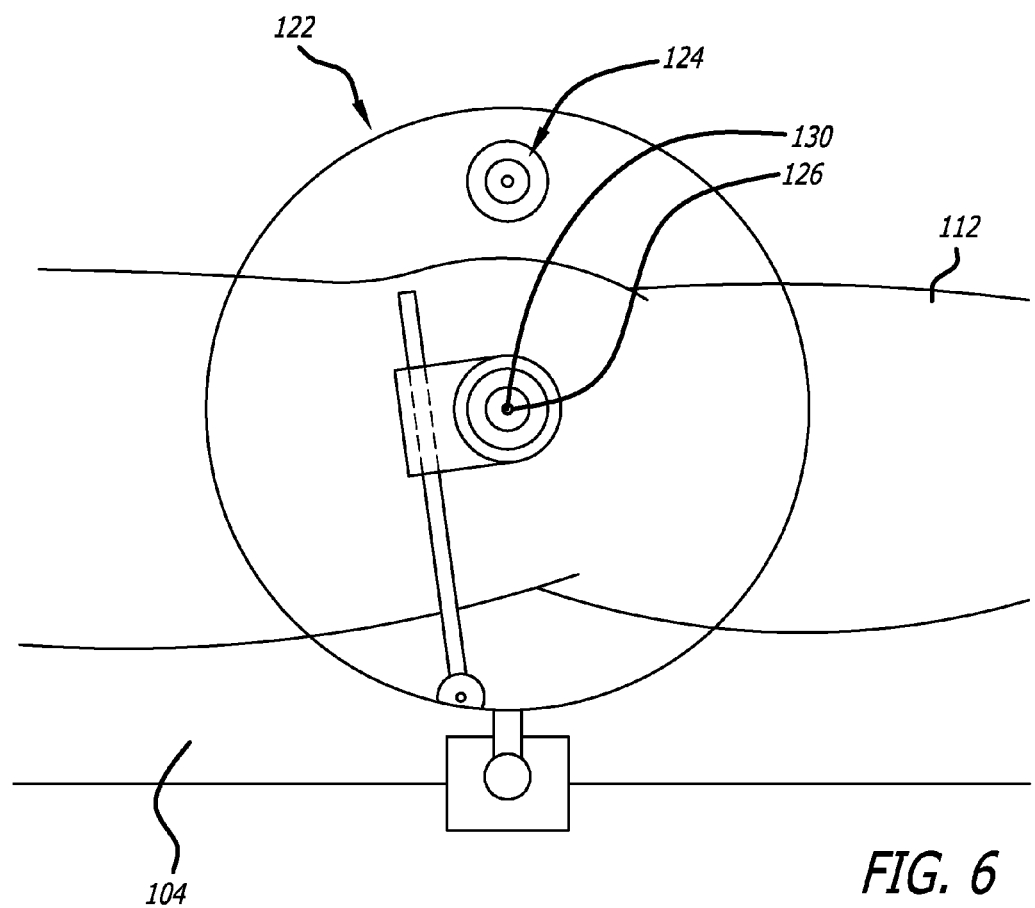
FIG. 6 is a top view, depicting one approach for identifying target patient anatomy.
Figure 6A:
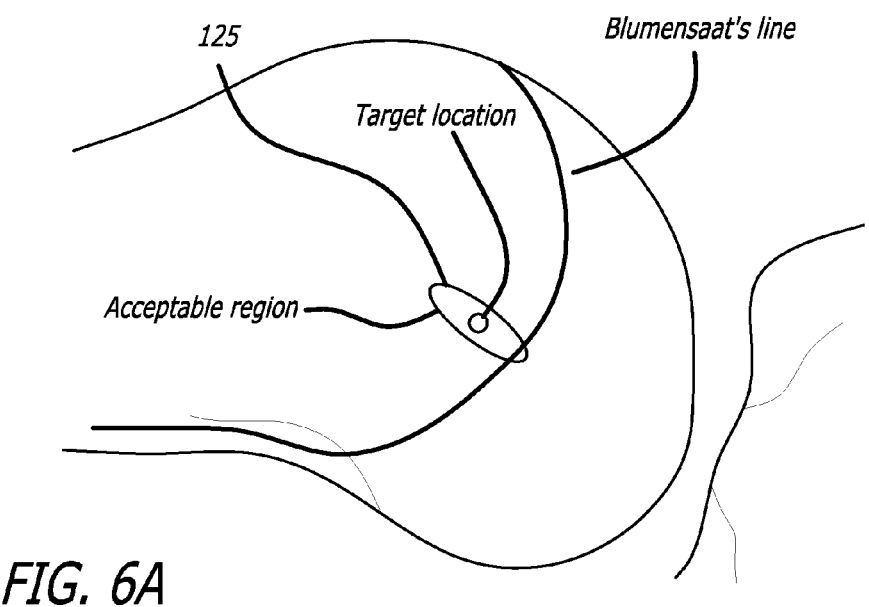
FIG. 6A is a perspective view, depicting a target location on a patient's anatomy.

In one approach, with reference to FIG. 6, an initial step in treatment involves identifying a patient's Blumensaat's line, which is a structural feature of a femur. With the patient laying on a surgical table as described above with respect to FIG. 1, fluoroscopy or other remote imaging techniques are used to view the anatomy of the lower leg 112. A leveling guide and platform assembly 122 is provided and clamped to the table 104. The platform 122 includes a bubble level 124 to aid in leveling the platform 122 relative to the leg 112. After proper orientation of the platform 122 is obtained, and a K-wire guide portion of the platform assembly is positioned as necessary above the patient's Blumensaat's line, the platform 122 is locked into position. The K-wire guide portion 126 of the platform assembly 122 is then employed as a guide through which a K-wire 130 (shown as a point in FIG. 6) is inserted and driven through tissue and into underlying bone at the Blumensaat's line. Additionally, anatomical landmarks (e.g., center of Blumensaat's line, inferior and posterior regions of the femoral condyles) can aid in manually positioning a K-wire in the target location and oriented lateral to the fluoroscopic view using the bulls-eye instrument. So positioning the K-wire aids in subsequently positioning a mechanical energy absorbing structure across a joint. This necessarily involves identifying a center of rotation of the femur. In one approach, the center of rotation is assumed or determined to be at a midpoint of Blumensaat's line. Other approaches recognize that the center of rotation is displaced from the midpoint of Blumensaat's line. As shown in FIG. 6A, using Blumensaat's line as an anatomical landmark, an acceptable region and target location 125 can be identified for placement of a center of a femoral socket (not shown).

Figure 7:
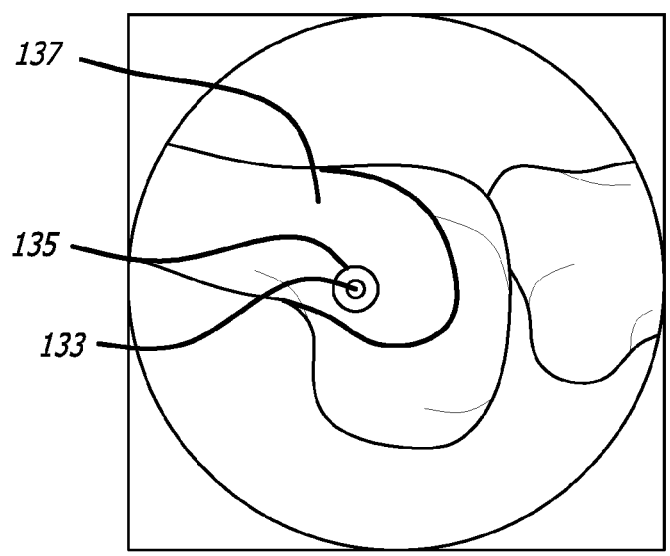
FIG. 7 is a side view, depicting use of a target for placement of a first K-wire into a femur.
Figure 8:
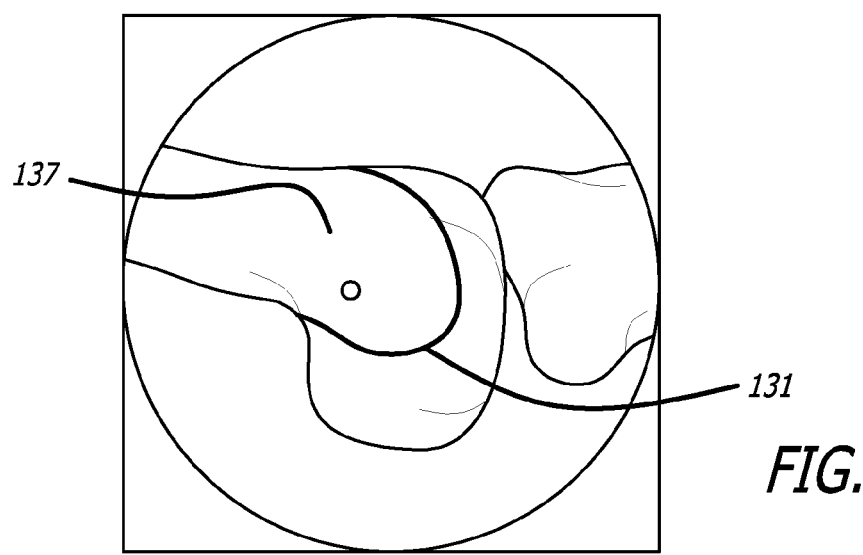
FIG. 8 is a side view, depicting placement of a K-wire into a femur.

In a preferred alternative approach, a femoral location for an energy manipulation device is identified. Palpation of the medial epicondyle allows a physician to find the recess/sulcus of the epicondyle which is considered the center of rotation of the knee. Alternatively, you can find the insertion of the MCL and that is considered the center of the knee rotation. First, a physician palpates the medial epicondyle and positions a K-wire antero proximal to the midpoint of Blumensaat's line 131 (See FIGS. 7 and 8). Using a bulls-eye instrument 133, a 2.4 mm K-wire 135 is inserted perpendicular to the lateral view of a femur 137. Care is taken to achieve accuracy as poor positioning of K-wires may lead to inappropriate placement and malfunction of an implanted device.

Figure 9:
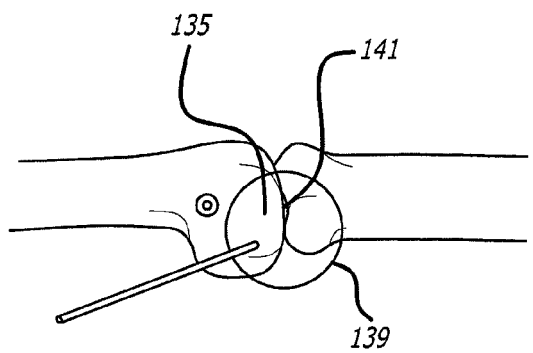
FIG. 9 is a perspective view, depicting use of a femoral guide.
Figure 10A:
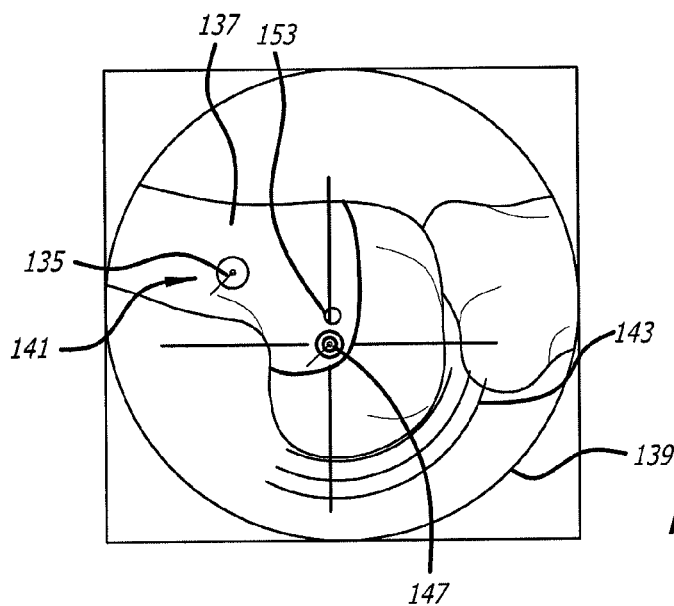
FIG. 10A is a side view, depicting use of the femoral guide of FIG. 9.
Figure 10B:
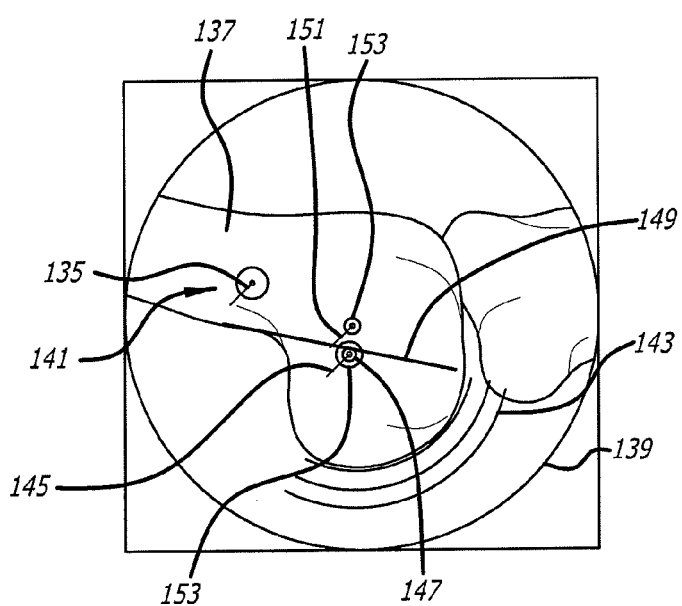
FIG. 10B is a side view, depicting further use of the femoral guide.

Next, with reference to FIGS. 9 and 10A, B, a femoral guide 139 is employed to accurately identify the femoral center of rotation. A moveable hole 141 in the femoral guide 139 is slid over the implanted K-wire 135. Under fluoroscopy, a physician determines which arc 143 on the guide 139 best fits the inferior and posterior regions of the femoral condyle. The selected arc is then aligned with the condylar curve. If the condylar curve falls between two arcs, the larger arc is selected. While maintaining arc alignment, a second K-wire 145 is drilled through a center hole 147 of the guide 139 (See FIG. 10B). Alternatively, a circle guide can be used. The circle guide can be, but is not limited to, the following forms: a series of concentric full circles or a series of concentric arcs (e.g., 90 deg, 140 deg, 135 deg) designed to match the posterior & inferior femoral region of femoral condyle.

Another form of the circle guide is a laminate applied to the fluoroscopic screen that the physician is viewing. Once the lateral view is achieved, patient position is maintained, and a laminate guide is attached to the fluoroscopic screen. The arcs or curves or circles of the laminate are positioned to align with the posterior and inferior regions of the femoral condyle. Magnification of fluoro can aide in this process. The laminate directly identifies the target location, and the physician inserts a K-wire into this target location on the patient by matching the location of the K-wire on the patient's anatomy to achieve the designated location shown by the target marker on the fluoro screen laminate. Further, the circle guide can be incorporated into the fluoroscopic screen (as part of the computer image) to simplify positioning of the arcs to the condyles on fluoro.

Additionally, a circle guide on the opposite side of the joint as that being operated provides an alternative means of finding the target location. This contralateral location provides the added benefit that distance of the guide from the joint (variable among patients due to the thickness of the soft tissue in this region) results in proportional magnification of the arcs relative to the condyles. Further, a combination of top and bottom circle guides can be employed The femoral guide 139 is then rotated until a straight line 149 extending across a portion of the guide 139 is aligned parallel to the femoral shaft 137. A third K-wire 151 is next drilled into an offset hole 153. Thereafter, the previously placed K-wires 135, 147 are removed as is the femoral guide 139, leaving the third K-wire in situ. The position of the third K-wire is used subsequently for accurate placement of a femoral rotational component of an energy manipulation assembly.

Figure 11:
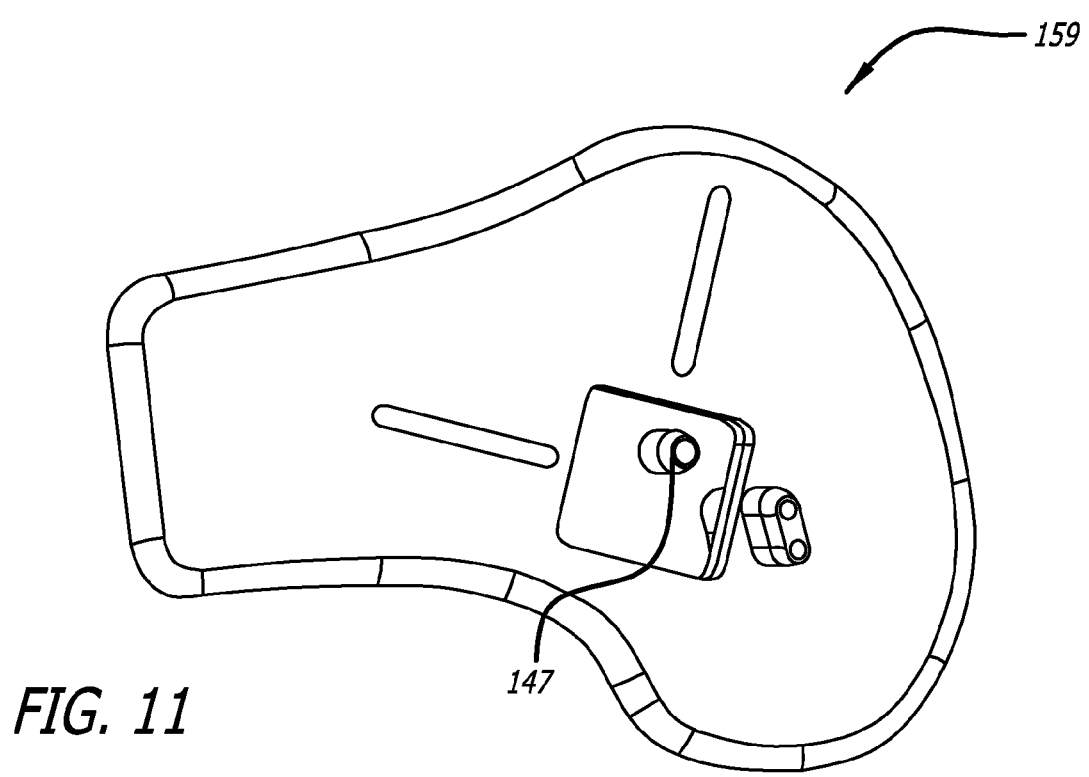
FIG. 11 is a side view, depicting an alternative embodiment of a guide.
Figure 12:
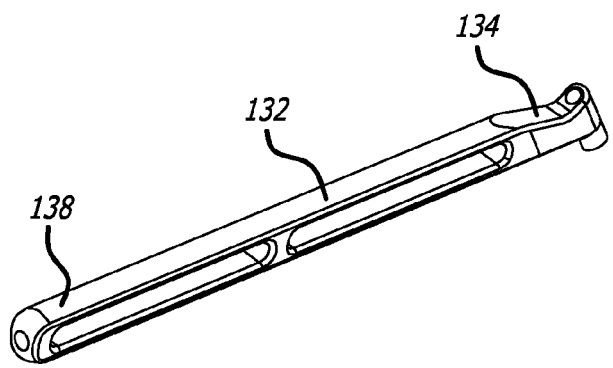
FIG. 12 is a perspective view, depicting an elongate holder apparatus.
Figure 13:
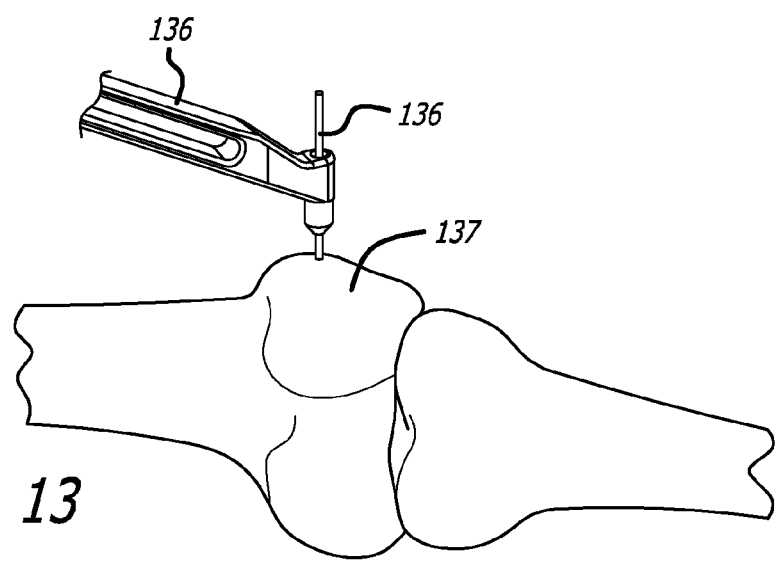
FIG. 13 is a perspective view, depicting the elongate holder apparatus positioned over body anatomy.
Figure 14:
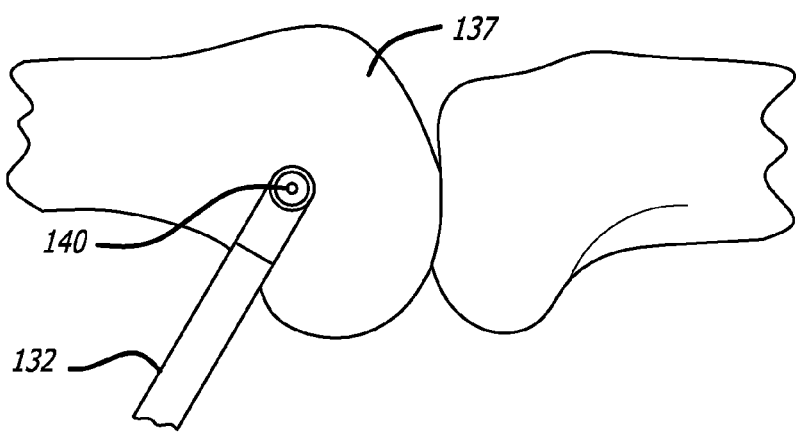
FIG. 14 is a side view, depicting the holder apparatus positioned over body anatomy.

One specific approach to an alternate design of a guide is shown in FIG. 11. Here, the guide 159 is configured for a left knee but other embodiments can be employed for other anatomy such as the right knee. The guide 159 also includes a center hole for receiving a K-wire and further embodies arcs (not shown) which show up under fluoroscopy. The arcs can similarly facilitate alignment with local anatomy and the ultimate positioning of a rotational component of an energy manipulation assembly.

Figure 15:
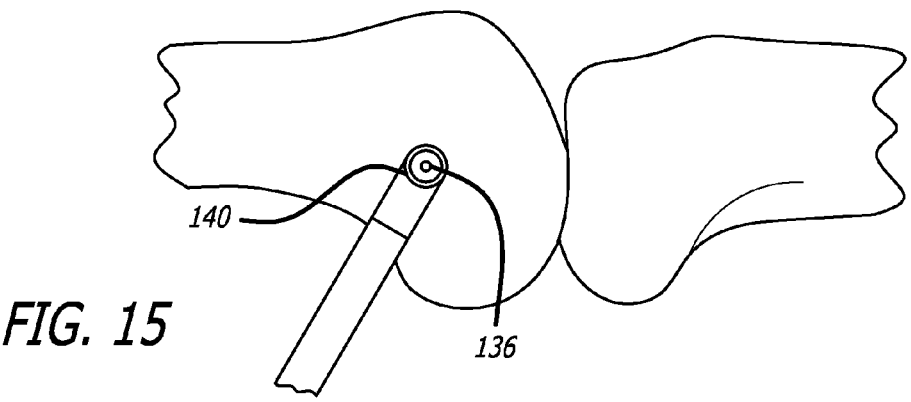
FIG. 15 is a side view, depicting target structure of the elongate holder apparatus.
Figure 16:
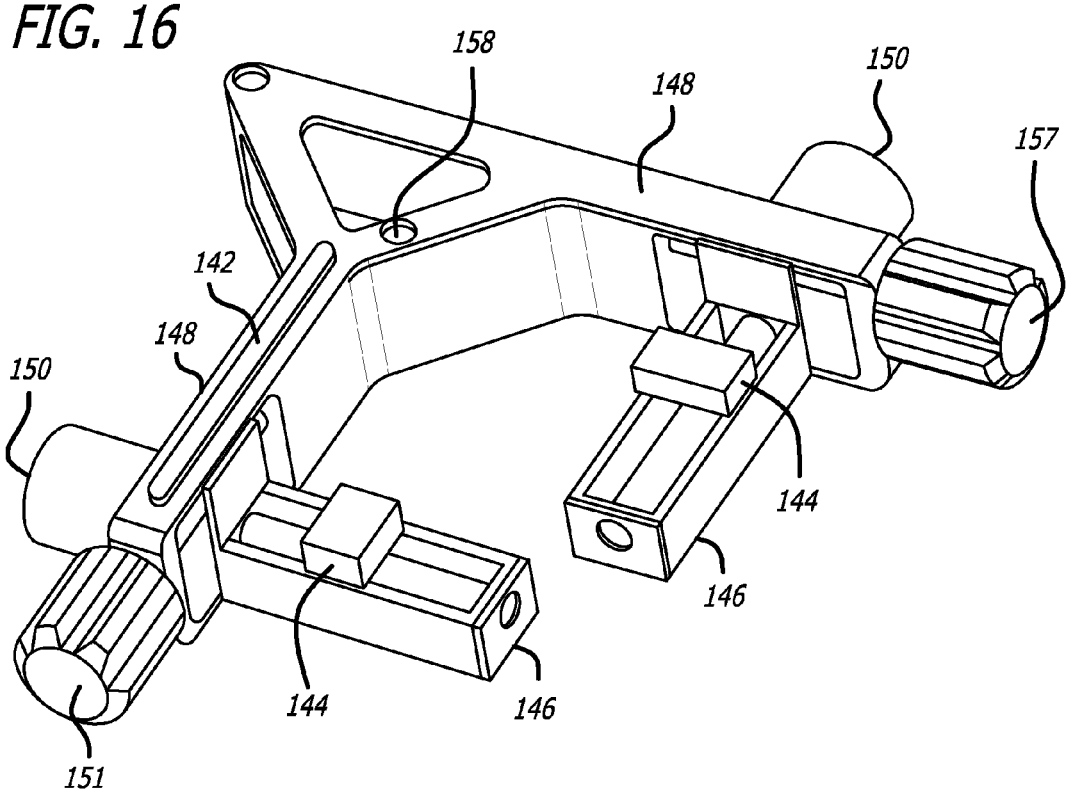
FIG. 16 is a perspective view, depicting a guide for approximating a center of rotation location of an articulating member.
Figure 17:
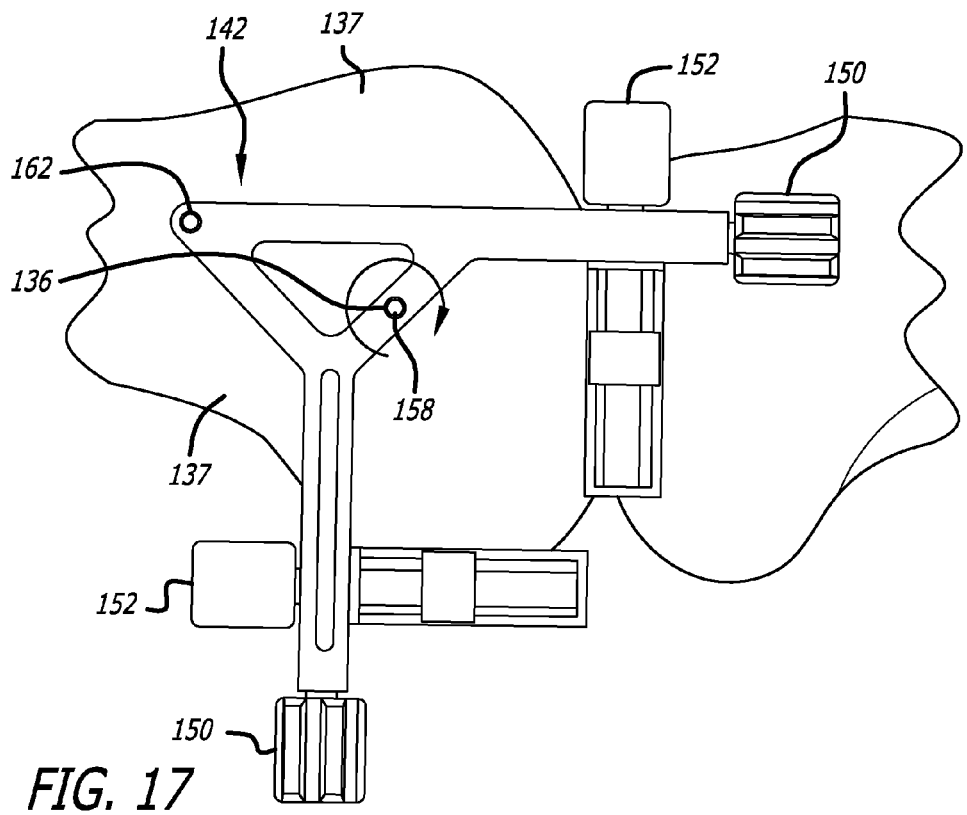
FIG. 17 is a side view, depicting a first step in employing the guide of FIG. 16.
Figure 18:
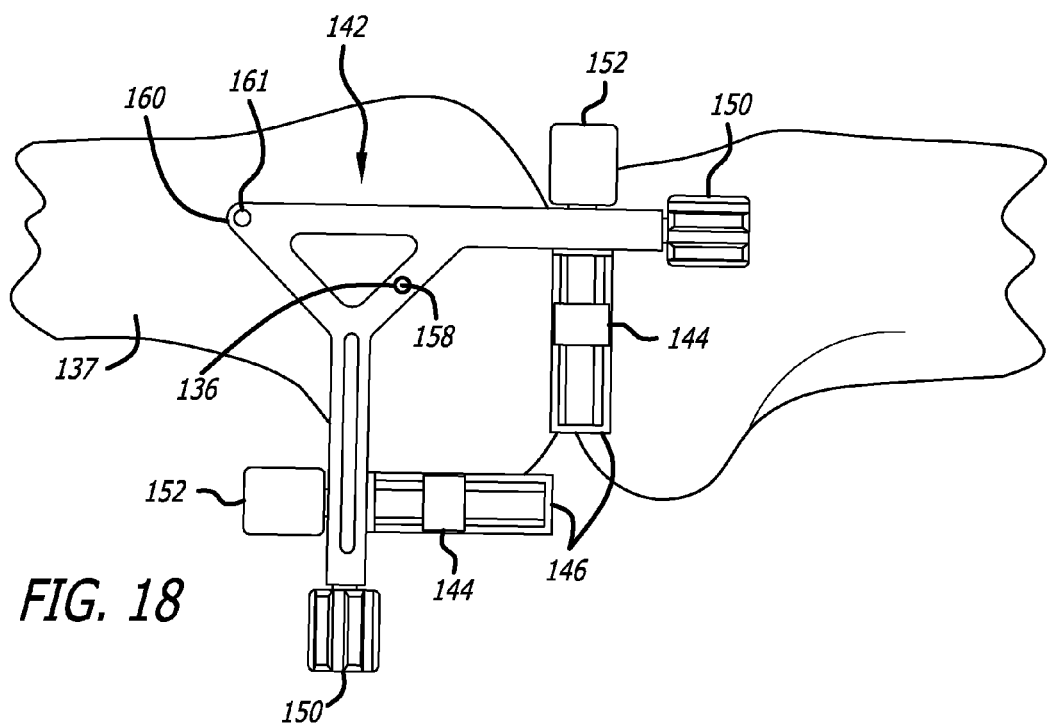
FIG. 18 is a side view, depicting a subsequent use of the guide of FIG. 16.

In yet another alternative approach, as shown in FIGS. 12-22, an initial step in an interventional procedure involving implanting a mechanical energy absorbing structure includes approximating a femoral location. Here, an elongate handle 132 including an arm 134 configured at its distal end is provided and configured to engage a mid-section of a 2.4 mm K-wire 136 to ensure accurate trajectory. A proximal end 138 is mounted to the surgical table as described previously. The K-wire 136 is positioned perpendicularly and above a femur 137 (See FIG. 13) and is positioned in an upper left quadrant (See FIG. 14) of an image provided by a remote viewing device such as that described above. The C-arm 134 is further equipped with a bulls-eye structure 140 to aid in properly positioning the K-wire within the desired quadrant. A fluoroscopic view of the bulls eye 140 and K-wire 136 is shown in FIG. 15. The K-wire is then fixedly advanced within the femur 137 for use in further aspects of the center of rotation location procedure.

Next, a right-angle guide 142 is provided to cooperate with the K-wire 136. For this particular application, a left knee guide 142 is provided but it is to be understood that various other guides such as those for a right knee or for other articulating joints can also be implemented.

The right angle guide 142 includes a pair of sliding members 144 each of which are received in respective channels 146 arranged orthogonally to arms 148 defining the guide 142. Knobs 150 are further provided to accomplish translating the sliding members 144 along the channels 146. Moreover, knobs 157 are provided to effect movement of the channels along arms 148. Additionally, the channels 146 include one component 152 of a cross-hair 154 while the sliding members 144 include a second component 156 of a cross-hair 154 (See FIG. 19). The guide 142 is also equipped with a K-wire receiving hole 158 arranged perpendicularly to front and back faces of the guide 142.

In use, tack-wire receiving hole 158 of the guide 142 is placed over the K-wire 136 so that the guide is placed adjacent the leg of the patient. The guide 142 is then rotated about the K-wire 136 to align the guide 142 with a longitudinal axis of the femur 137. An optional axis guide (not shown) can be used to aid in alignment with the longitudinal axis. A second K-wire 160 is placed in a second through hole 162 formed in the guide 142 to fix the rotation of the guide 142 (See FIGS. 17 and 18).

Figure 19:
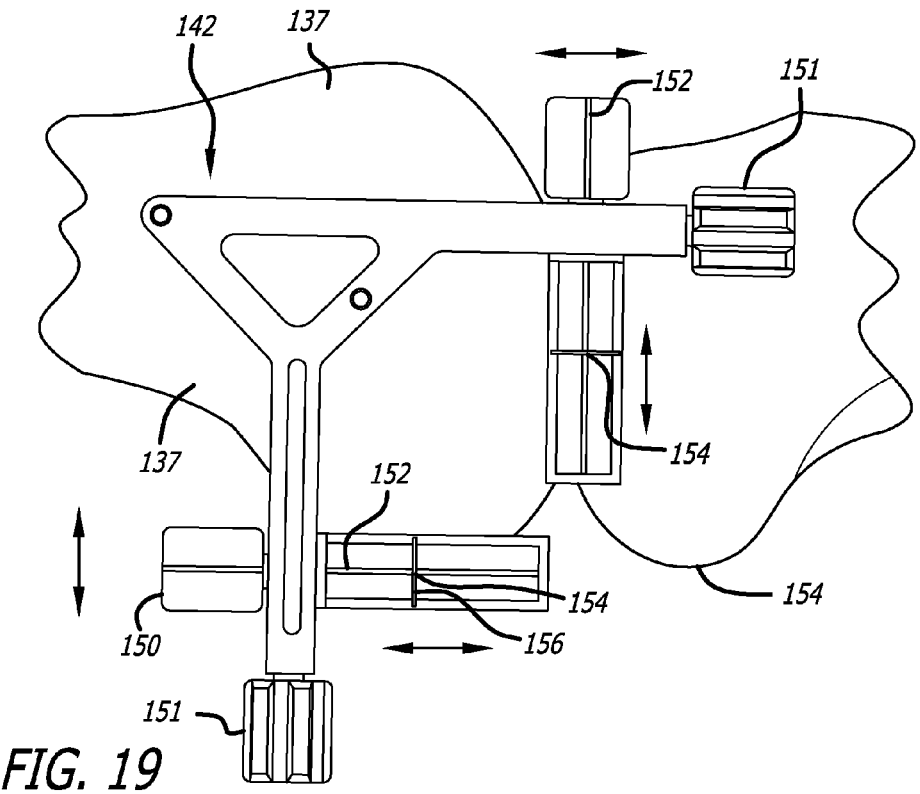
FIG. 19 is a side view, depicting further operation of the guide of FIG. 18.
Figure 20:
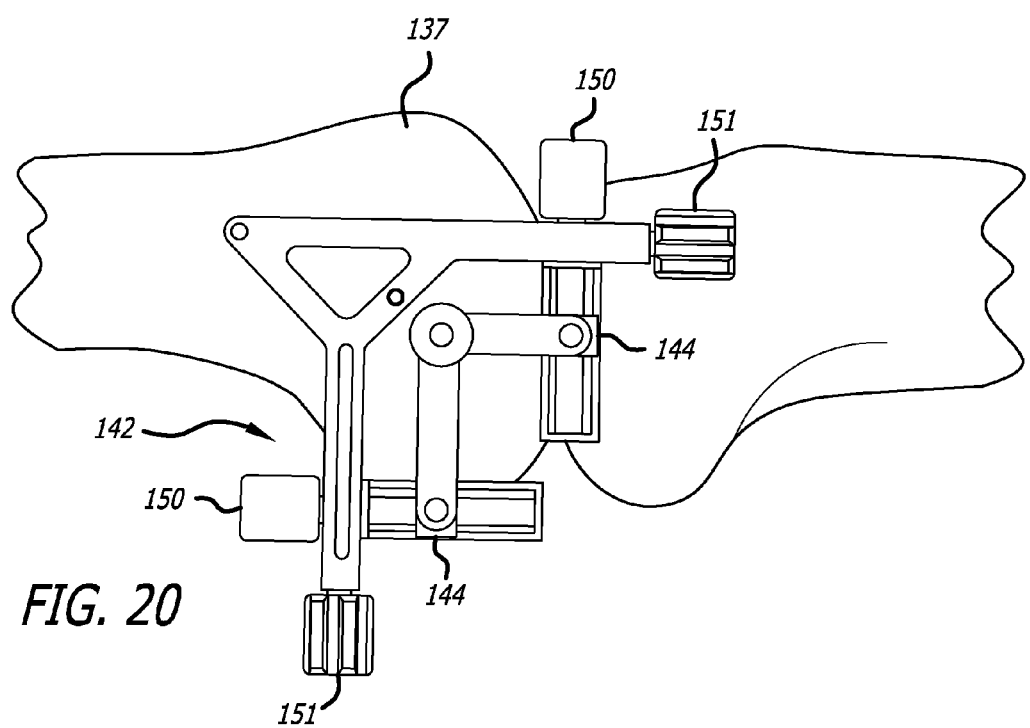
FIG. 20 is a side view, depicting use of a link in combination with the guide of FIG. 19.
Figure 21:
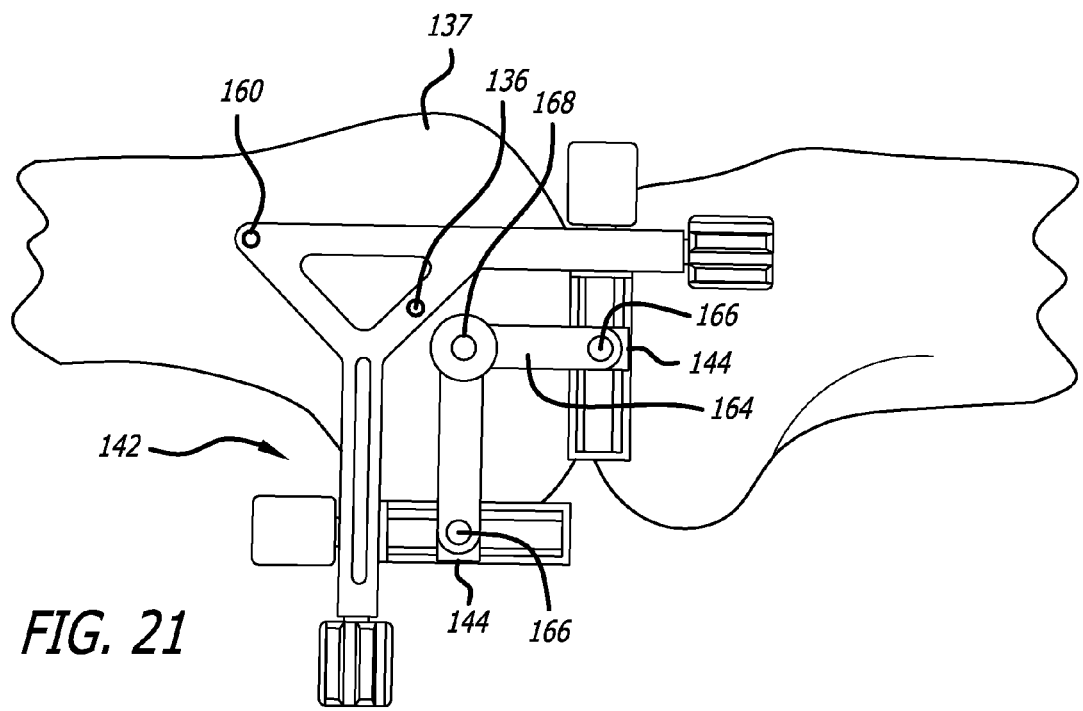
FIG. 21 is a side view, depicting yet further use of the guide of FIG. 20.

The cross hairs 154 are then aligned tangent and coincident to posterior and inferior condyles of the bones of the articulation joint (See FIG. 19). This is accomplished by rotating knobs 150 and 157 to move the channel 146 and slider 144 within the channel 146. Proper positioning of the cross-hair is accomplished through remote imaging techniques.

Thereafter, a linkage 164 is selected from a line of available, variably dimensioned linkages and is placed into engagement with the sliders 144. Notably, the links define a generally right angle device with terminal ends equipped with holes for receiving posts 166 extending from the sliders 144 (See FIG. 21).

Figure 22:
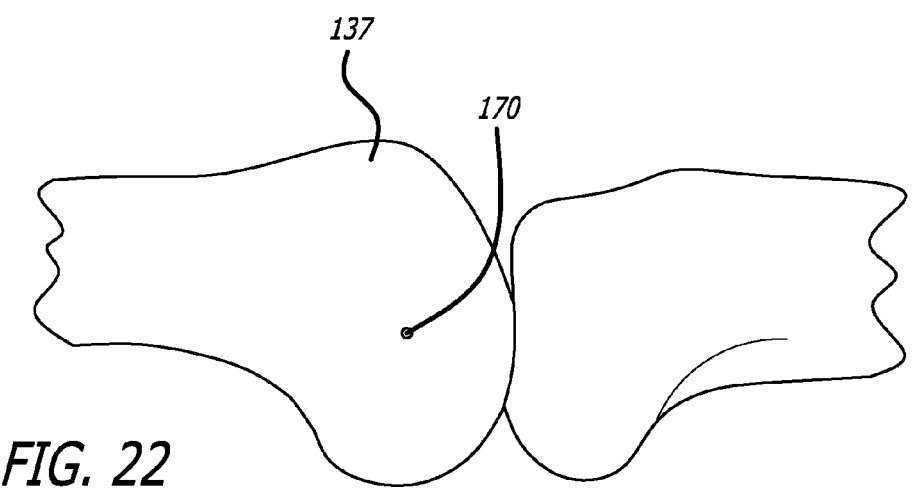
FIG. 22 is a side view, depicting body anatomy with the guide of FIG. 21 removed.

The linkage 164 further includes a K-wire receiving through hole 168 positioned at a junction between arms which define the linkage 164. This through hole lies above the femoral center of rotation. A further K-wire 170 is inserted through this hole 168 and fixedly attached to the femur 137 as shown in FIG. 22. Thereafter the linkage assembly 164 is removed along with the previously placed K-wires 136, 160.

An alternative form of targeting can be used, involving the linkage apparatus with an electronic readout of absorber length. Optimal position can be determined by moving the target location until the readout in extension and flexion provide the appropriate change. This can be aided using a set of rules guiding how to adjust position based on the readout results of the previous position.

Figure 23:
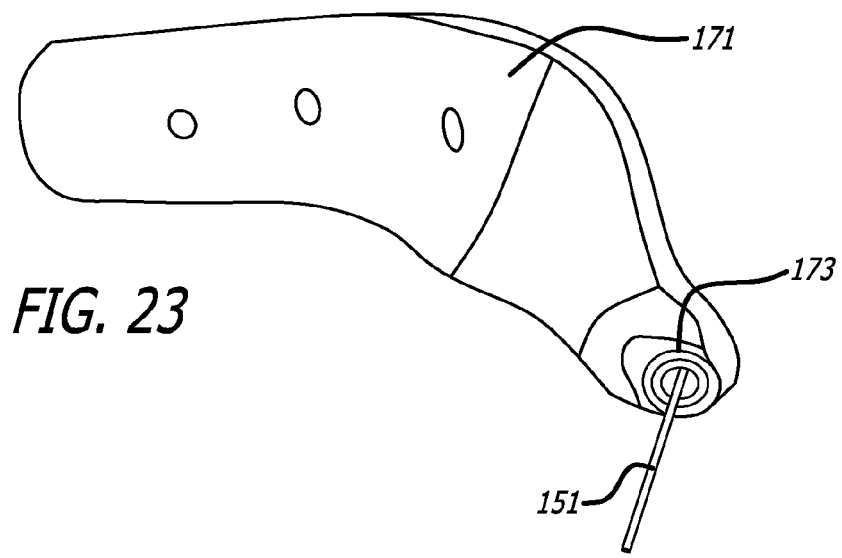
FIG. 23 is a perspective view, depicting use of a femoral base trial.
Figure 24:
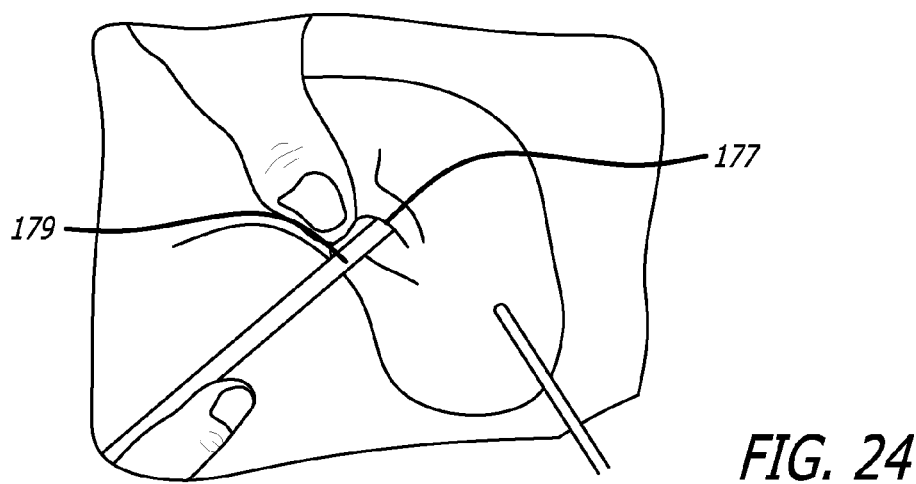
FIG. 24 is a perspective view, depicting gaining access to an implantation site.

Once the third K-wire 151 (FIG. 11) or K-wire 170 of FIG. 22 is placed at the center of rotation, the next challenge becomes identifying the areas for mounting components of a mechanical energy absorbing system. In one approach, a femoral base trial component 171 is slid over the remaining third K-wire 151 (See FIG. 23). The base trial 171 includes a connector mount 173 which references the K-wire 151. A 3-5 cm incision from the K-wire 151 extending along the posterior edge of the trial base component 171 is then made (See FIG. 24). Using blunt dissection, the vastus medialus is elevated and retracted anteriorly and laterally to provide sufficient bone exposure to enable adequate removal of periosteum 177 and base component placement. To accomplish this, a periosteum elevator 179 can be employed.

It is to be recognized that inadequate retraction of the muscle groups and exposure of bone may lead to poor visibility of the region and hinder base implant size selection and periostium removal. Moreover, it must be borne in mind that the medial superior genicular artery may cross the operative field just above the knee. If so, it should be protected, ligated or coagulated to avoid postoperative hematoma.

Next the trial femoral base component 171 is slid over the K-wire 151 and the fit is checked to determine if a continuous apposition of the base to bone exists around edges. Efforts are made to avoid the application of excessive force to preserve registration of the distal end K-wire location. Various templates are utilized to select a preferred base component. Sizing and positioning can be confirmed by using remote imaging (fluoroscopy) as well as a gap sizing tool (not shown) to ensure that a majority of the base component edge is secured against the bone with an acceptable minimum distance in any gap areas.

If osteointegration is required the base component should make intimate contact with the bone surface. In this case, the periostium in contacting regions of the femoral base can be removed using a blade, curette or the periosteal elevator 179. It is to be ensured that a sufficient region of periosteum is removed or retracted to provide intimate contact between an entire base component surface and bone. Further, when possible, the periostium should be pulled back so that it can be repositioned over the base component once the base has been attached. Here, measures are taken to avoid inadequate removal of periosteum as the same may prevent osteointegration of the bone into the base component. Moreover, excessive removal of periosteum beyond the base component margins should be avoided as that may reduce the bloody supply to the bone.

Figure 25:
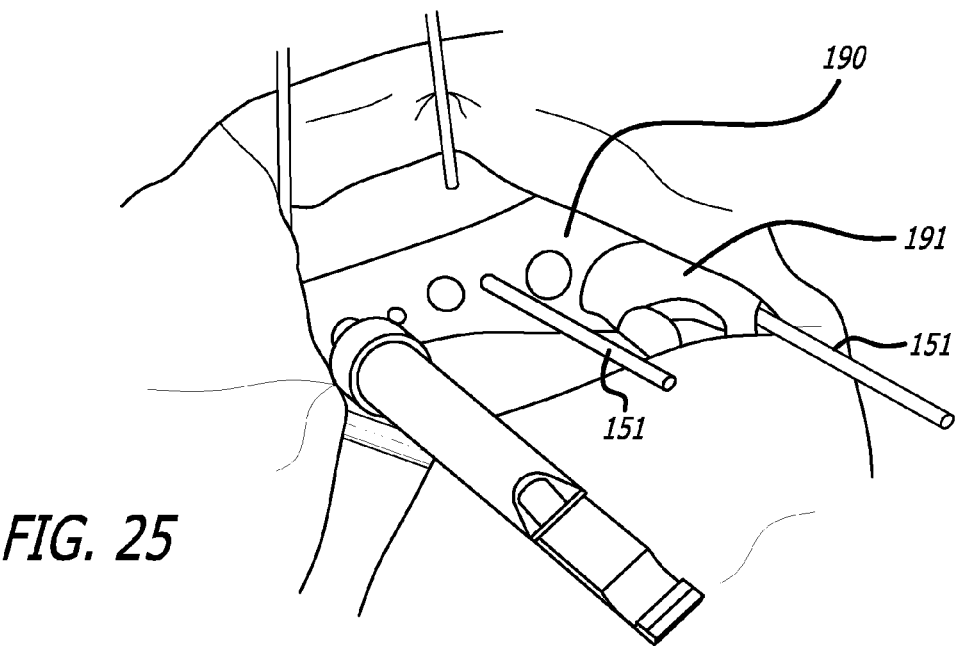
FIG. 25 is a perspective view, depicting placing a base component on a femur.

Once a preferred base component is selected, it is removed from its packaging and visually inspected for any obvious defects. If visual defects are observed another like part is selected. As shown in FIG. 25, the base component 190 is then placed on the prepared femoral bone 137 by sliding the ball and socket 191 over the femoral K-wire 151. At this point, a temporary ball and socket affixed to the base can be employed. Thereafter, two stabilizing K-wires are drilled into the available holes on the base component to maintain implant positioning. It is to be noted that slight adjustments in position of the base component at this point will assist in seating the base component on the bone and aid finding the best fit between the base component and the bone. Movements should be gently executed to preserve registration of the distal end K-wire location and protect the osteointegration surface.

Figure 26:
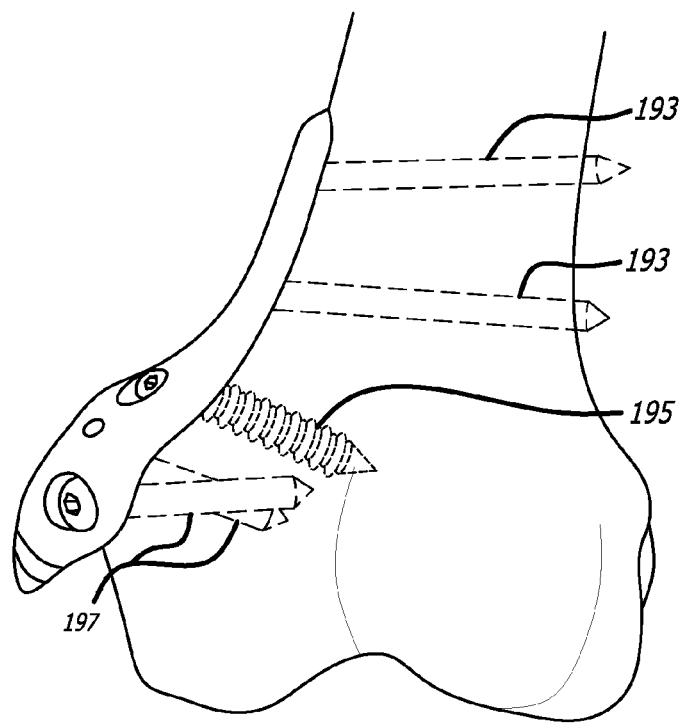
FIG. 26 is a perspective view, depicting attachment of a base to a femur.
Figure 26A:
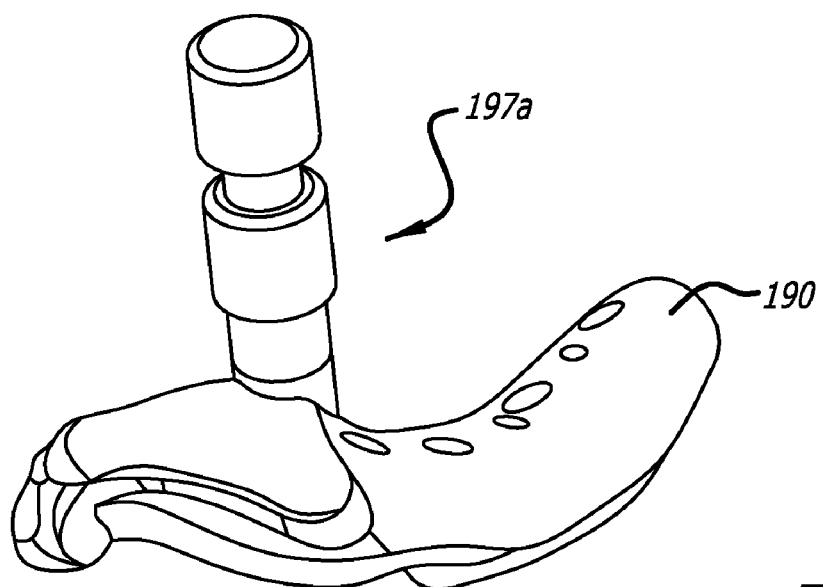
FIG. 26A is a perspective view, depicting a femoral placement guide.

Turning now to FIG. 26, the fixation of the base components to bone can begin, starting with the proximal 3.5 mm bicortical compression screws 193. An appropriate drill bit and drill guide are selected. Then screw length is determined by measuring drill holes with a depth gauge in standard fashion. In one approach, assurances should be made so that both cortices are captured by the compression screws 193. To ensure that the base 190 stays at a correct location relative to the K-wire 151 while the base 190 is attached to bone, a femoral placement guide 197a can be employed (See FIG. 26A). The guide 197a is configured to be temporarily attached to the base 190 and later removed when the base attachment is completed.

After placing the first bi-cortical screw 193 to the desired tightness, a gap sizing tool (not shown) can be used to ensure that the base 190 is properly positioned and that no new gaps have formed. If the gap sizing tool indicates an unacceptable gap, the base component must be repositioned or osteointegration may not occur properly. This procedure is repeated for the second 3.5 mm bicortical 193 and 6.5 mm unicortical compression 195 screws. All three compression screws are tightened to their final setting before initiating locking screw placement. The two K-wires are removed from the base component 190. A further verification is made at this time to ensure that the target K-wire 151 has not been bent or moved. It is to be noted that the compression screws 193, 195 should be inserted and fixed prior to initiation of the locking screws to ensure good compression of the base component 190 onto the femur 137, thereby maximizing osteointegration.

Figure 26B:
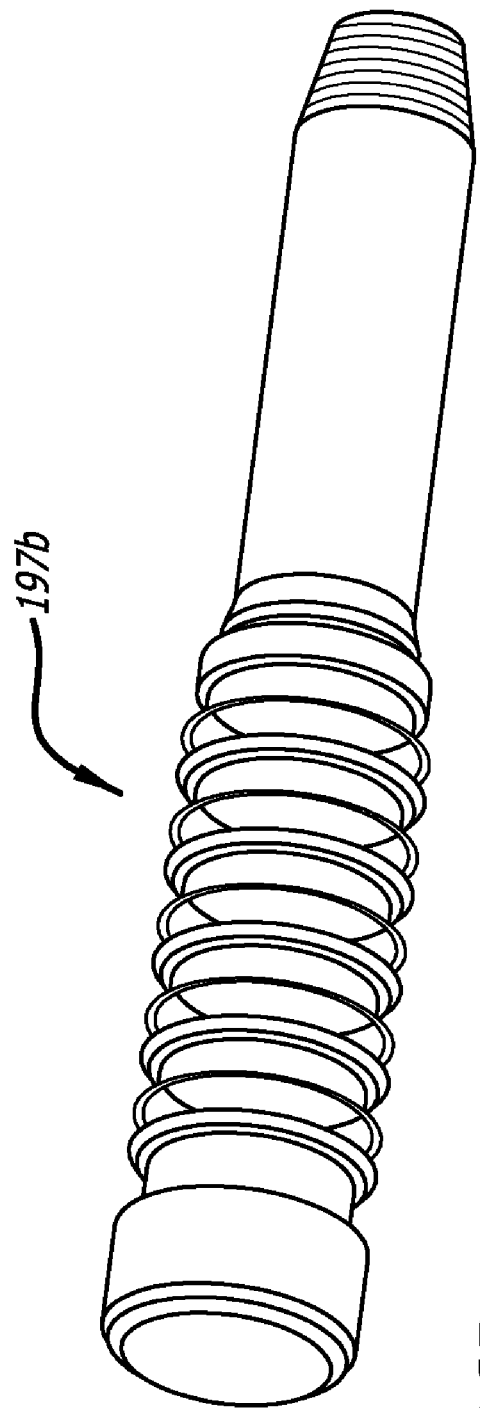
FIG. 26B is a perspective view, depicting a locking screw guide.

Next, in order to place locking screws 197, the correct drill bit and threaded drill guide 197a (See FIG. 26B) are selected, such as for 5.0 mm locking screws. The locking drill guide is threaded into the base component 190. A pilot hole is drilled while ensuring minimal disturbance to the base component 190. The locking screw 197 is then screwed in place to the specified tightness (such as 4 Nm torque). This procedure is repeated for the second locking screw 197. The locking screws are positioned in the area of the base component that is raised off of the bone surface. The locking of the screws to the base in this region and then extending into the bone create a rigid structure to minimize movement of the base.

Figure 27:
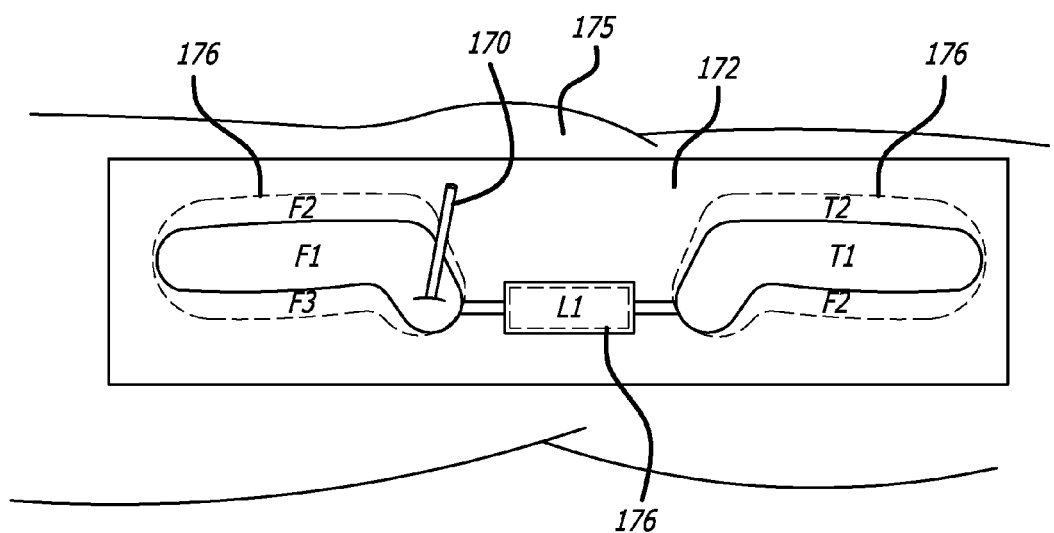
FIG. 27 is a side view, depicting a second approach to a template for a use at an interventional site.

In a second approach (See FIG. 27), a plastic template 172 is placed over the patient's leg 175 in the area where the interventional implantation procedure is to occur. Starting base component sizes $F_1$ and $T_1$ and a link component $C_1$ are roughly approximated to a patient's anatomy. A pen or other marker is used to outline appropriate base sizes 176. Perforated outlines can allow for directly marking a patient's skin. Incision lines (not shown) can also be made in the area.

Figure 28:
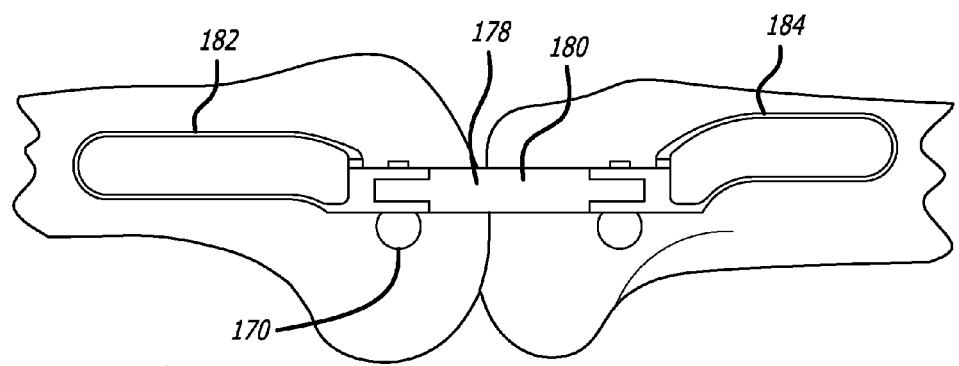
FIG. 28 is a side view, depicting second embodiment of a template for use at an interventional site.
Figure 29:
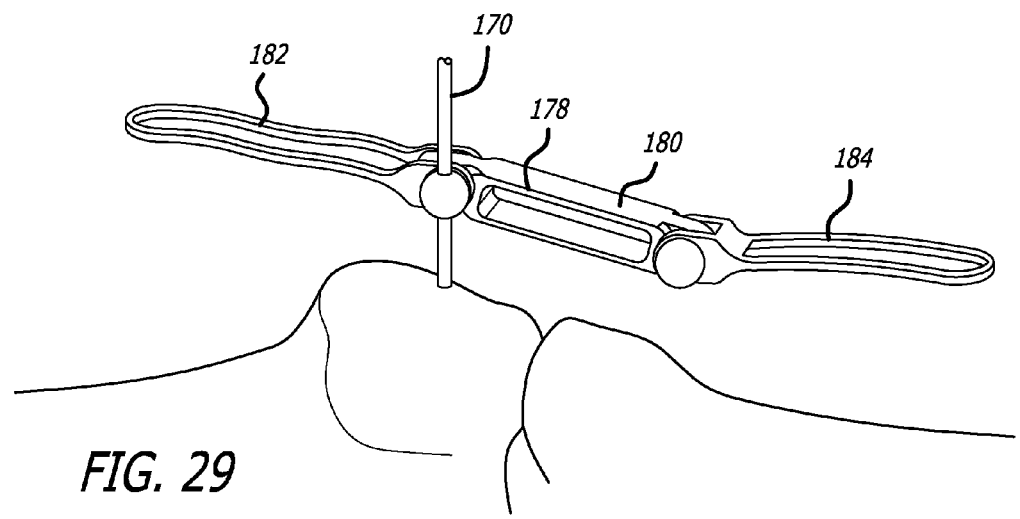
FIG. 29 is a perspective view, depicting the template of FIG. 27 adjacent body anatomy.

With reference to FIGS. 28 and 29, an alternative approach to a template 178 is depicted. This second approach involves an articulating assembly having a middle section 180 which approximates a link component, the middle section 180 having ends to which curved, elongate hoops 182, 184 are rotatably connected. The hoops 182, 184 have a length and shape approximating base components to be used on opposite sides of an articulating joint, such as a knee joint.

At the point of connection between the middle section 180 and a first elongate hoop 182, there is configured a guide 184 having a through hole sized to receive the K-wire 120 placed at a patient's anatomy center of rotation. Accordingly, the articulating template 178 is placed adjacent a patient's skin in the area of the implantable site to thereby provide structure for facilitating selection of proper components for a mechanical energy absorbing assembly. Again, marks 176 can be made on a patient's skin to map out a desired component shape and orientation, as well as to identify a location for initial incisions.

Figure 30:
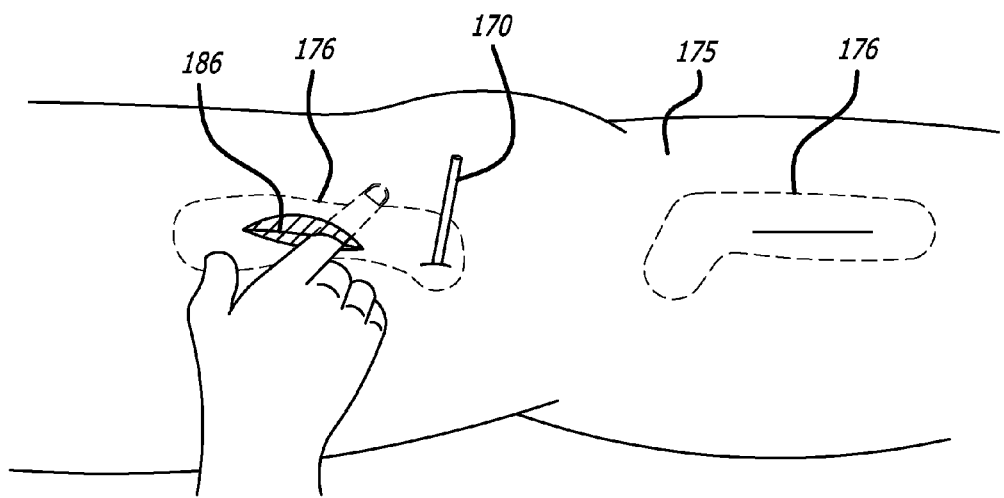
FIG. 30 is a perspective view, depicting physical examination of a mounting site within a patient's anatomy.
Figure 31:
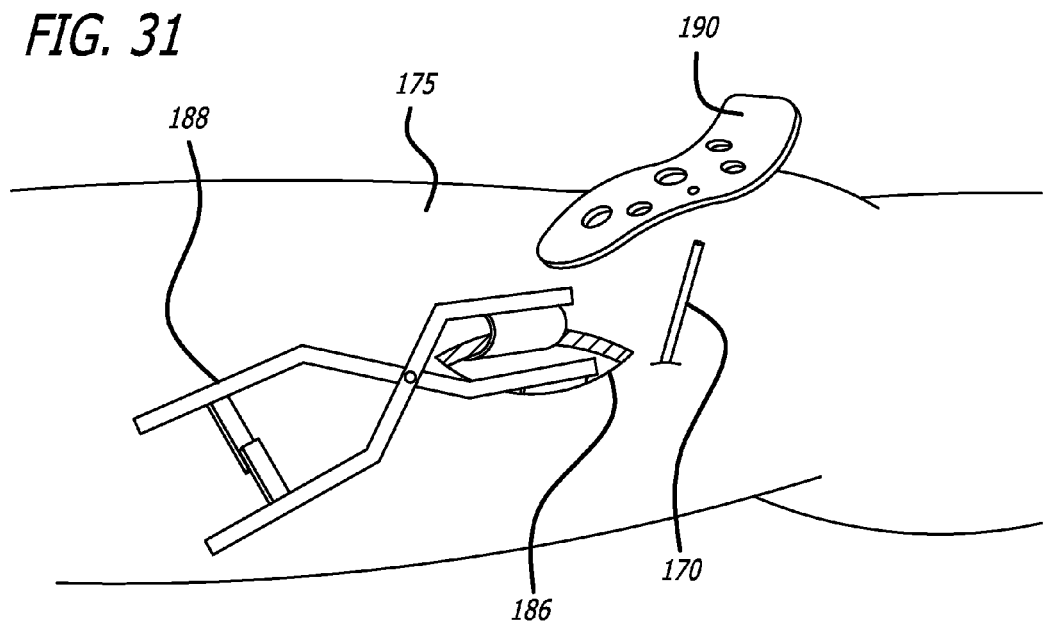
FIG. 31 is a perspective view, depicting use of a retractor at an interventional site.

After making a first incision 186 within the mapped area, tissue is dissected to the bone. As shown in FIGS. 30 and 31, in an application to the knee joint, the first incision 186 is made through skin and tissue coincident with the femur. The dissection is made vertically or longitudinally along the leg 175 and is made along natural tissue planes, posterior to the vastus medialus muscle (not shown). The underlying periostium is elevated and removed as necessary while employing standard surgical techniques and an effort is made to avoid disrupting the joint capsule. To prepare the implantation site, access is provided by a scissor-action retractor 188. When possible, the periosteum should be pulled back so that it can be repositioned over the base component once the base has been attached.

In most instances, an one inch incision on a femoral side of a knee joint is adequate. A tissue dilator or the surgeon's finger can be used for blunt dissection of tissue from the periostium in an area where a base component would be placed and extending to and beyond the point where the K-wire 170 is affixed to bone. The femoral base component 190 is test fitted based upon contact area with the bone and clearance from periostium. In this way, the general contour of a desirable femoral base component can be identified. The base component 190 is then removed from the area.

Figure 32:
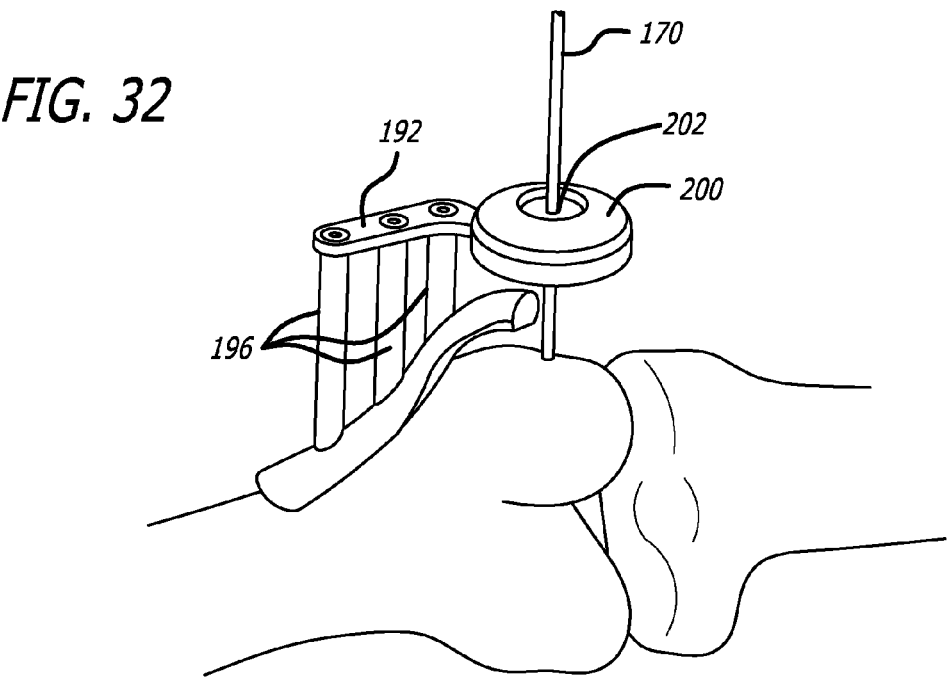
FIG. 32 is a perspective view, depicting use of a base trial at an interventional site.
Figure 33:
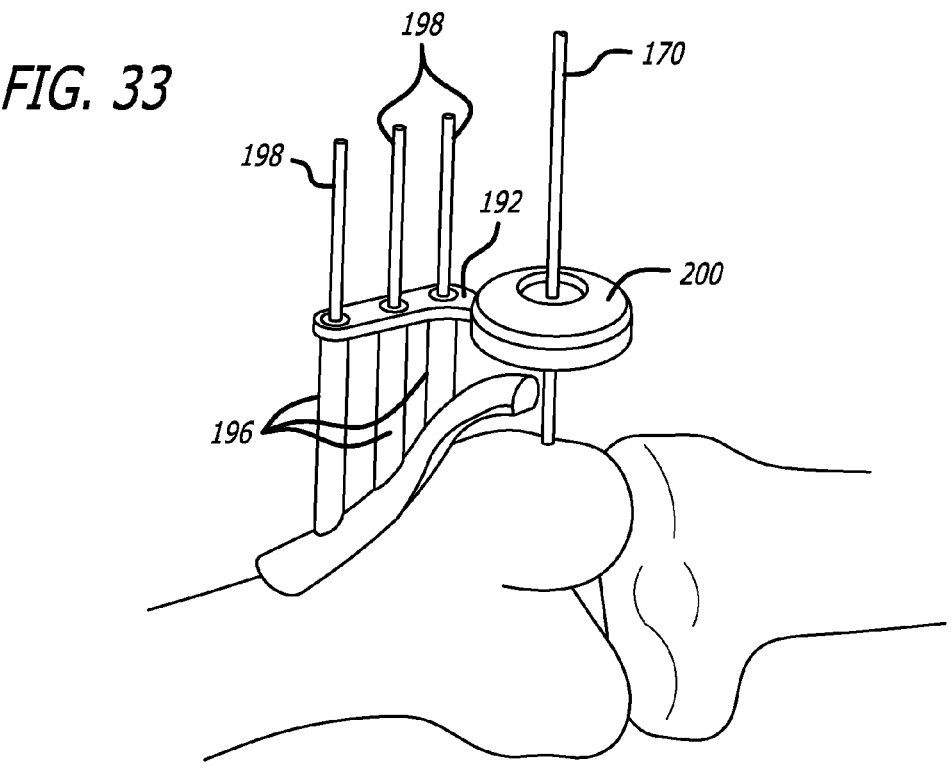
FIG. 33 is a perspective view, depicting further use of the base trial at the interventional site.

With reference to FIGS. 32 and 33, in one approach, a next step can include employing a base trial 192 to create initial mounting holes for a base component 190. The base trial 192 to be used can be one of a number of available trials and the selected trial 192 will embody a base component portion 194 having a shape and size approximating that previously identified as being desirable. Alternatively, the base trial itself can be used in place of a previously described series of steps to identify proper contour of the base 190. Extending vertically from the base component portion 194 are a plurality of tubes 196, each sized to receive a single K-wire 198. Attached to upper ends of the tubes 196 is an arm, a laterally displaced end of which defines a disk 200 having a hole 202 extending therethrough and being sized to receive the K-wire placed, in the present example, at the femur center of rotation. This disk 210 allows the trial 192 to move in three dimensions.

Figure 34:
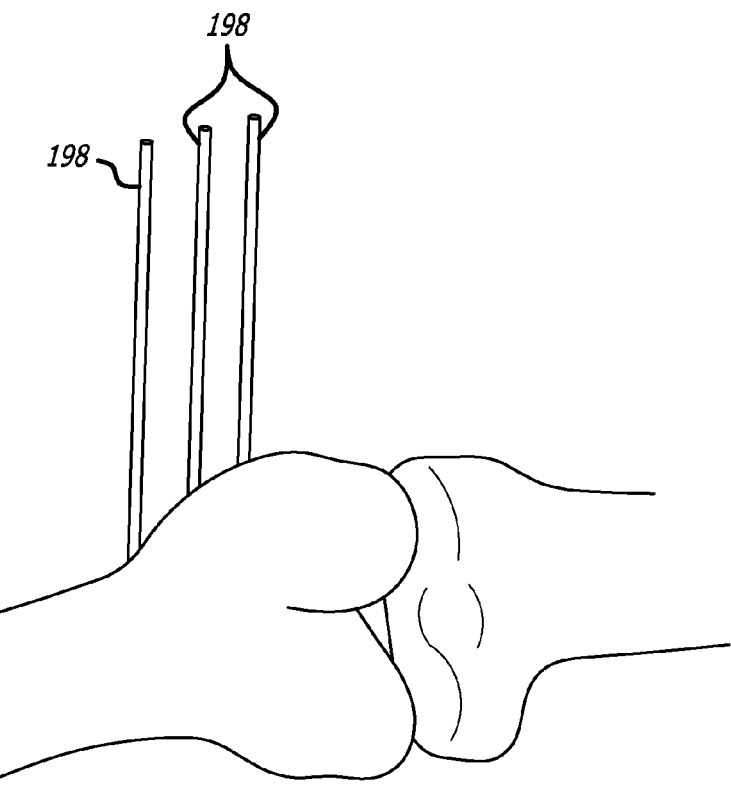
FIG. 34 is a perspective view, depicting the interventional site with the trial base of FIG. 24 removed.
Figure 35:
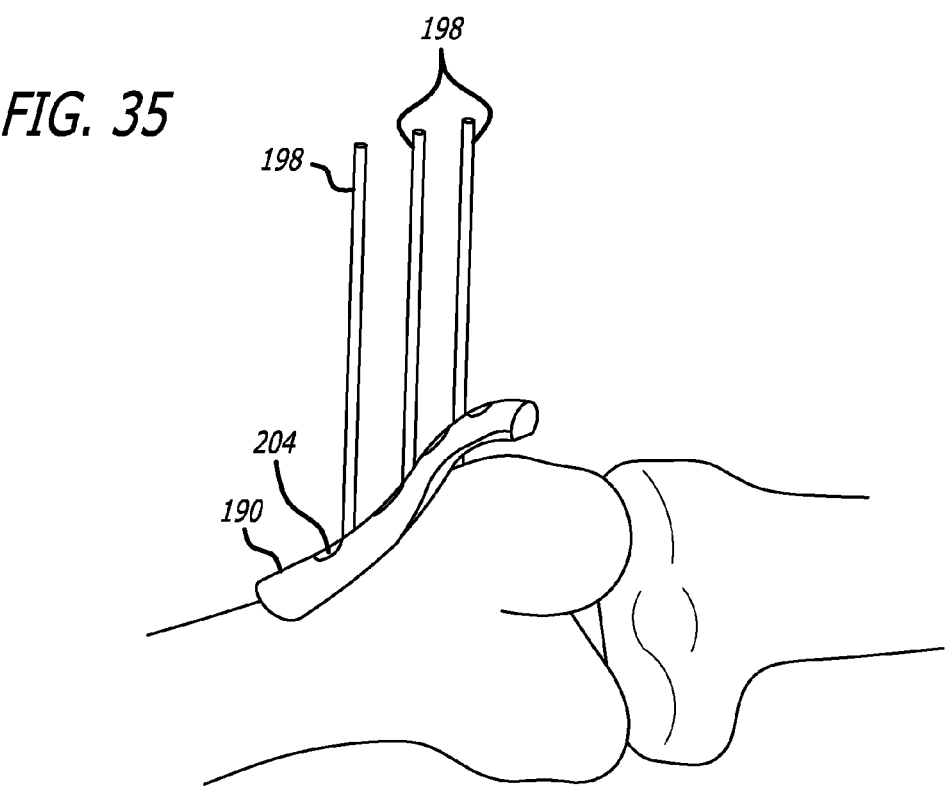
FIG. 35 is a perspective view, depicting placement of a first base component adjacent body anatomy.
Figure 36:
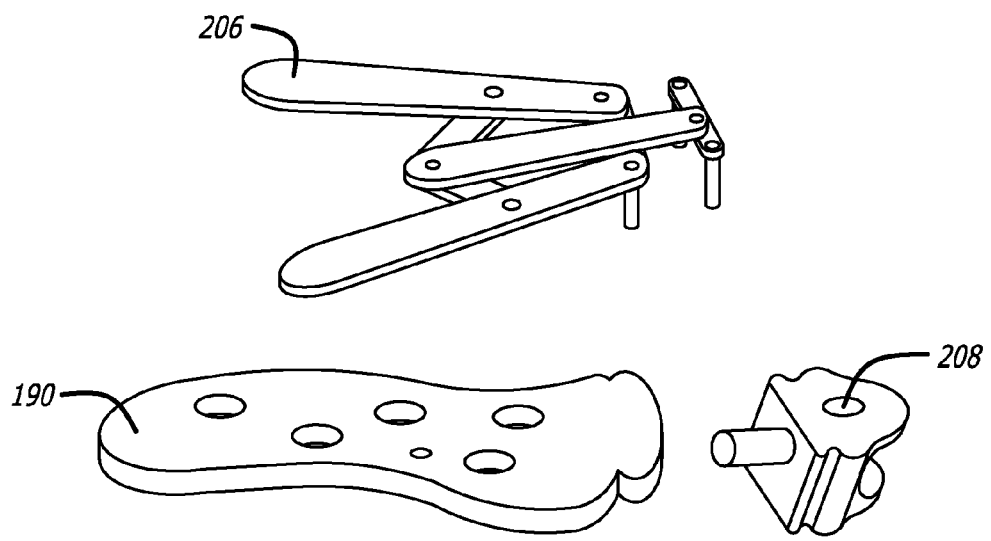
FIG. 36 is a perspective view, depicting a tool shaped for attaching a socket mount to a base component.
Figure 37:
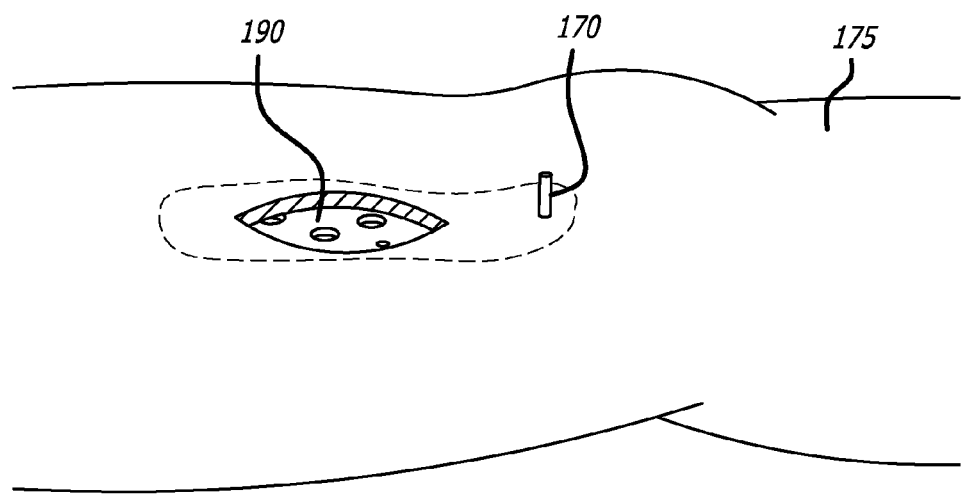
FIG. 37 is a perspective view, depicting a base component placed at an interventional site.
Figure 38:
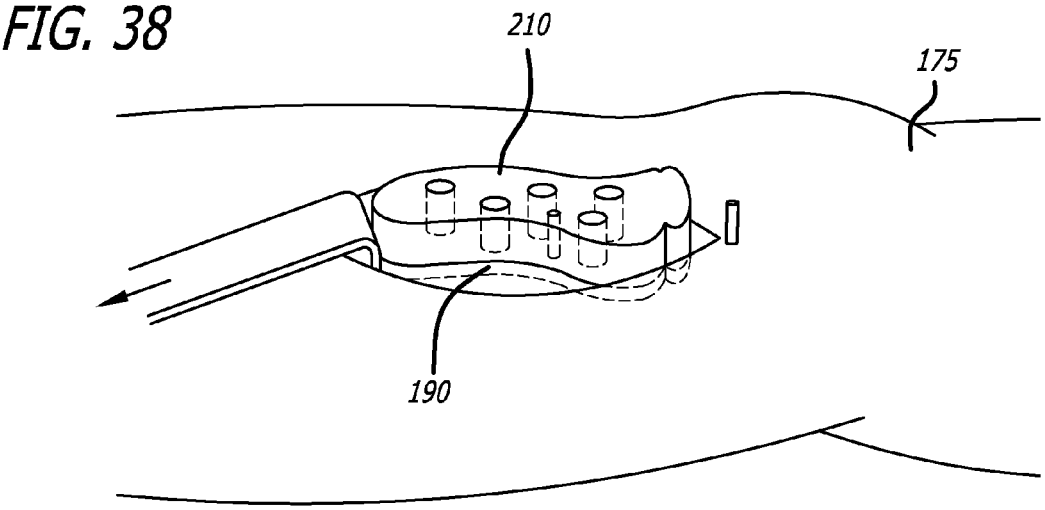
FIG. 38 is a perspective view, depicting use of a drill guide at the interventional site.
Figure 39:
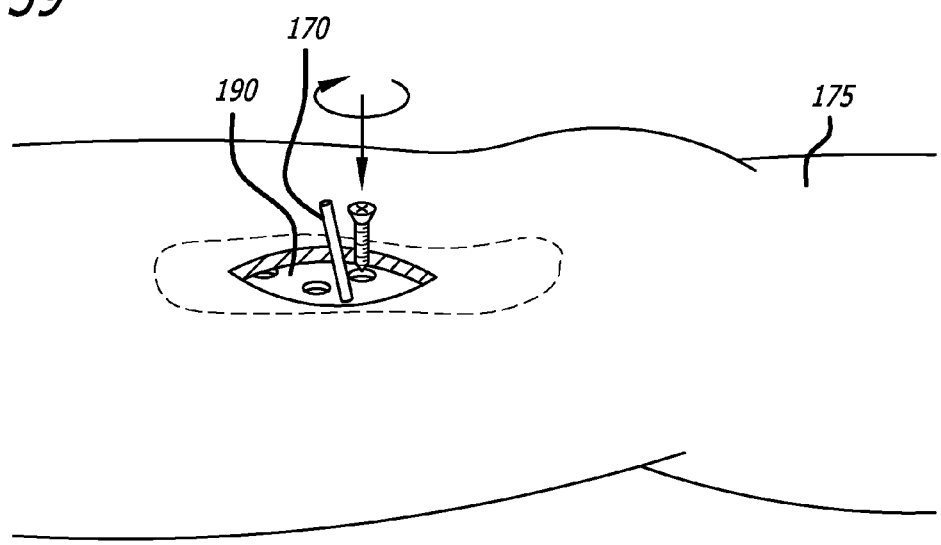
FIG. 39 is a perspective view, depicting attaching a base component at an interventional site using fastening devices.

After sliding the disk 200 of the base trial 192 over and along the K-wire 170, the base component portion 194 is placed adjacent bone. Next, the K-wires 198 are inserted through the tubes 196 and fixedly inserted into the femur (See FIG. 34). The K-wire 120 placed at the center of rotation is then removed. The base trial 192 is then also removed from the interventional site and a properly sized base component 190 including holes for receiving the K-wires 198 is placed against bone using the K-wires 198 as a guide for proper placement. In an alternative approach, a K-wire with a non-round shape (for example, triangular or square) with a matching hole on the base component 190 can be used in place of two K-wires. The non-round shape keeps the base component in the proper orientation.

Once placed against bone, mounting access holes 204 formed in the bone component 190 are employed to drill holes into underlying bone. Screws (not shown) are then used to affix the base component 190 in the desired orientation and the K-wires 198 are removed from the area.

In another approach, as shown in FIGS. 36-39, a base component 190 can alternatively be placed against a cleared surface on the bone, guidance therefor being provided by the K-wire 170 placed at a center of rotation. A component clamping tool 206 is employed to affix a K-wire socket 208 to the base 190, in the event the base 190 lacks such structure. One or more forms of this component clamping tool 206 is contemplated to be used to also subsequently assemble other components of the mechanical energy absorbing device in situ. Various temporary K-wire sockets can be used to match the K-wire hole at the center of rotation dependent on where the base component 190 best fits on the bone.

A femoral drill guide 210 is then used to provide a guide for directly attaching holes through the base component 190 and into bone at desired angles (See FIG. 29). Such desired angles are selected to achieve necessary affixation of the base 190 to the bone as dictated by the patient's anatomy as well as load carrying requirements. The base component is then affixed to bone as shown in FIG. 30.

Figure 40:
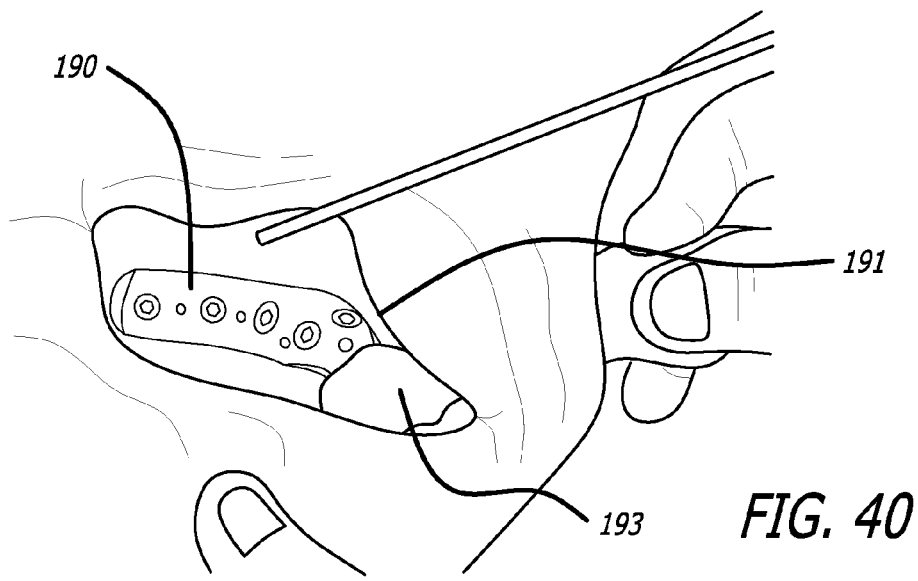
FIG. 40 is a perspective view, depicting forming a tunnel beneath the skin.

After the first base component 190 is attached to bone and the temporary K-wire socket is removed from the base, various approaches can be employed to assemble in situ the remaining components of an energy manipulating system. In one preferred approach, a first step involves creating an absorber tunnel. A distance of approximately 60 mm is measured from the femoral K-wire 151 along the direction of the tibial shaft. A 2-4 cm incision 191, beginning at the 60 mm mark is made and extends inferior along the tibial shaft. With reference to FIG. 40, using blunt dissection such as by the physician's finger or a tissue dilator, an extracapsular tunnel 193 for an absorber unit is formed beneath the skin and through soft tissue that extends from femoral to tibial incisions. The physician then ensures that the channel is free of fibrous attachments and can accommodate the absorber element. A clear and continuous channel should exist between the femoral base component an expected location for a tibial base component. Alternatively, the incision can be extended across the entire length to avoid tunneling. The energy manipulating system can be pushed or pulled through the tunnel between the two incisions. The energy manipulating system can be temporarily housed in a sheath or a dilating introducer.

Figure 41:
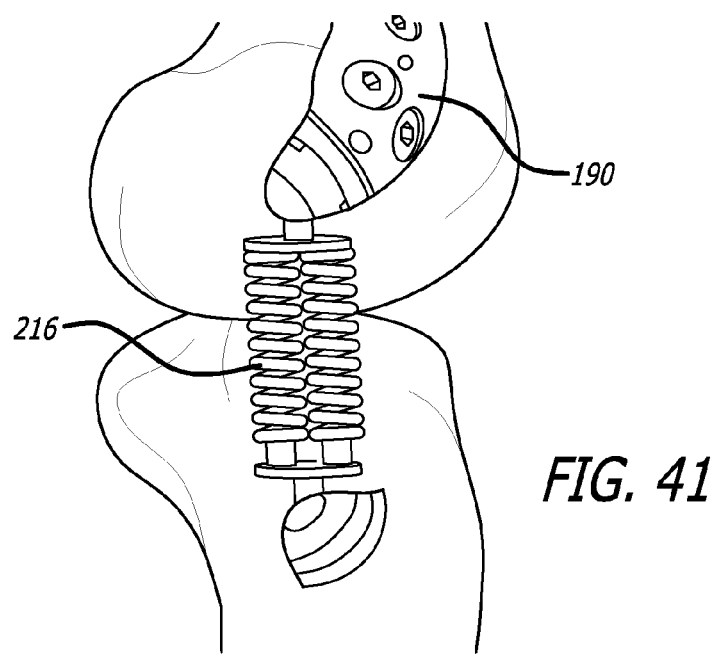
FIG. 41 is a perspective view, depicting the femur and tibia with a femoral base and an absorber unit.

Since the infrapatellar branch of the saphenous nerve may be located in this region, care should be taken to prevent injury to this structure. Moreover, it is to be noted that the knee must be in full extension during tibial positioning and attachment and the gap between the femur and tibia should be closed by the physician by applying a varus stress on the leg for a medial placement, a valgus stress on the leg for a lateral placement, and an axial stress on the leg for a bilateral placement of an absorber(s). Failure to maintain this position may result in incorrect absorber length, inadequate device function, or device failure. Next, using fluoroscopy, the absorber unit 216 is positioned so that it is perpendicular to the tibial plateau (See FIG. 41). It is to be noted that the absorber unit can be configured within a sheath and held in a compressed state, the ends of which can be folded during and held back for initial implantation. A K-wire can be drilled (not shown) at the neck of the ball to hold the absorber in this alignment.

Figure 42:
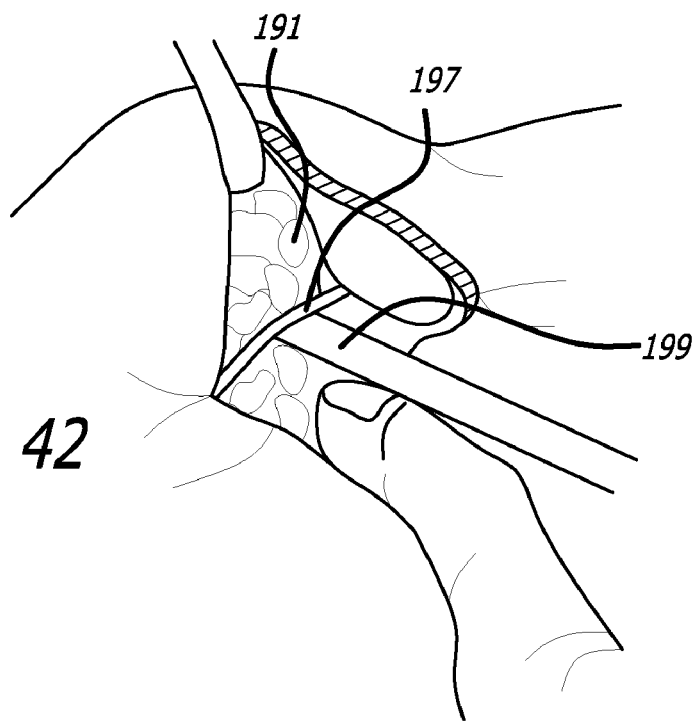
FIG. 42 is a perspective view, depicting forming a space for a tibia base component.

At this time, a tibial base component size is selected. As shown in FIG. 42, the skin is retracted to provide sufficient bone exposure for placement of the tibial base component. A tibial trial base component (not shown) can be placed at the side to check the fit (continuous apposition of base to bone is desired around edges). Excessive force of placement should be avoided to preserve integrity of the mounting location. Using sizing templates, the preferred base component can be selected. Sizing should be confirmed to ensure that a majority of the base component edge is secured against the bone with an acceptable minimum distance in any gap areas. These steps are taken while ensuring that absorber alignment is maintained at all times. The periostium 197 is removed in contacting regions of the tibial base using a blade, curette or periosteal elevator 199. A sufficient region of periosteum should be removed or retracted to provide intimate contact between the entire base component surface and bone. It is to be recognized that inadequate removal of periosteum may prevent osteointegration of the bone into the base component. Moreover, excessive removal of periosteum beyond the base component margins may reduce blood supply to the bone. When possible, the periostium should be pulled back so that it can be repositioned over the base component once the base has been attached.

Once a proper sized tibial base is selected, it is removed from its packaging and visually inspected for any obvious defects. If visual defects are observed, another component is selected. The tibial base 215 is then attached to the absorber 195 using an assembly tool (See FIGS. 74-80).

Figure 43:
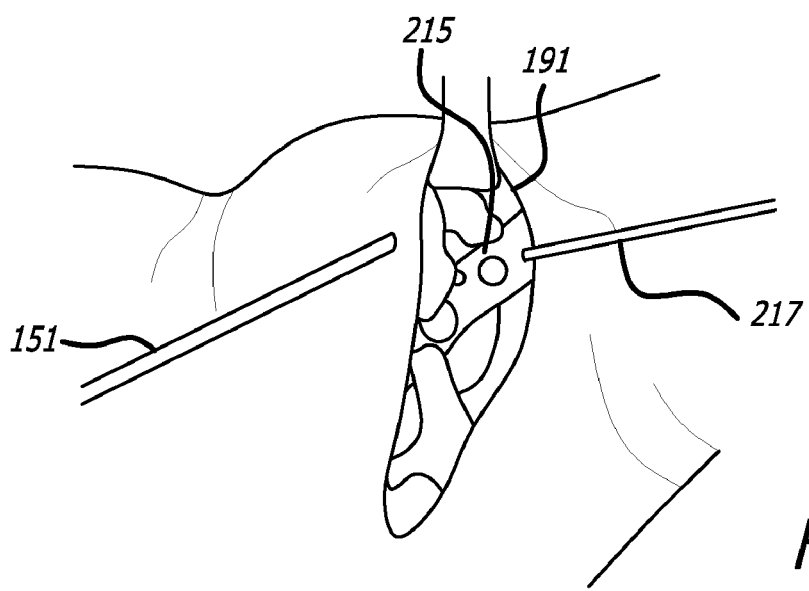
FIG. 43 is a perspective view, depicting attaching a tibia base to an absorber.

As shown in FIG. 43, the base component 215 is then placed onto the prepared tibial bone and it is readjusted to find the optimal positioning. During tibial attachment, the knee should be in full extension with varus stress for a medial placement. In certain applications as for example those relating to knee, it has been found to be beneficial to close a gap between the bones forming a joint and then selecting an optimum position for placement of the second base component. Further, varus or valgus stresses can be applied to close the gap between the joint members. In this way, the ultimate positioning of the second (tibial) base will then involve ensuring that there will be sufficient space between joint members when a complete extra-articular mechanical energy absorbing apparatus is placed across the joint. Moreover, slight adjustments in position of the tibial base component 215 at this point will assist in seating the base component on the bone and aid in finding the best fit between the base component and the bone. Alignment of the absorber 195 must be maintained at all times. Adjustments in base position should be gently executed to protect the osteointegration surface on the base component. One or more stabilization K-wires 217 can be drilled into the available holes on the tibial base component 215 to maintain position.

Figure 44:
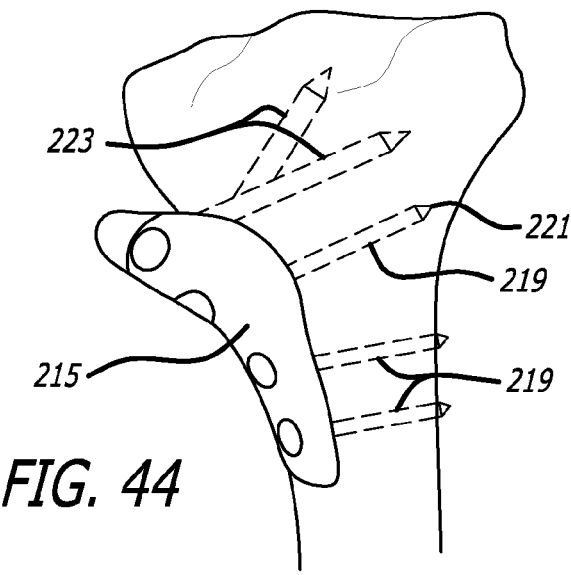
FIG. 44 is a perspective view, depicting the tibia with a base attached thereto.
Figure 45:
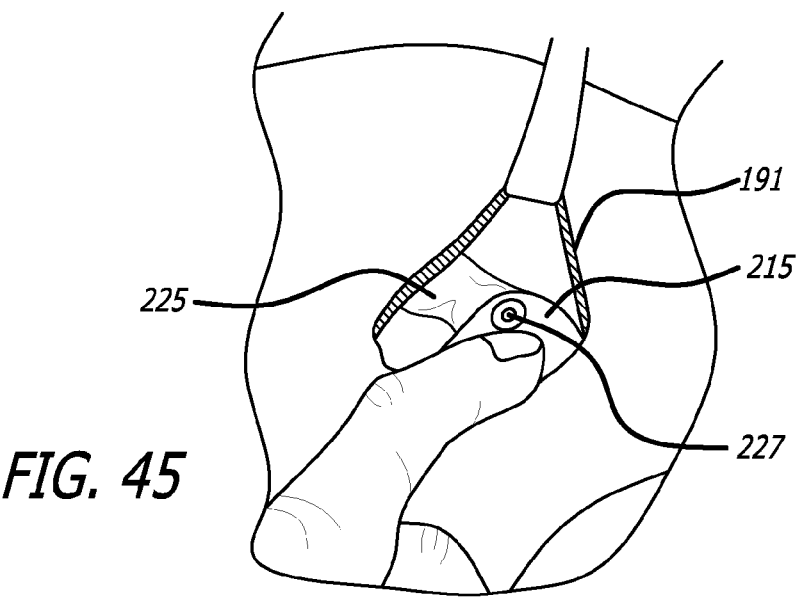
FIG. 45 is a perspective view, depicting manipulation of a sheath surrounding an absorber.

The fixation of the tibial base component to the bone with distal 3.5 mm compression screws 219 can now commence (See FIG. 44). An appropriate drill bit and drill guide (not shown) are selected and a pilot hole is drilled in the area. Appropriate screw lengths are then determined by measuring drill holes with a depth gauge in standard fashion. Steps are taken to ensure that both cortices are captured by the 3.5 mm compression screws.

After placing the first screw base to the desired tightness, a gap sizing tool (not shown) can be used to ensure that the base is properly positioned and that no new gaps have formed. If the gap sizing tool indicates an unacceptable gap, the base component should be repositioned. This procedure is repeated for the second 3.5 mm bicortical 219 and the 6.5 mm unicortical 221 compression screws. The three compression screws should be inserted and fixed prior to initiation of the 5.0 mm locking screws 223 to ensure good compression of the base component onto the tibia, thereby maximizing osteointegration. All of the compression screws are then tightened to their final setting. The K-wire 217 is removed from the tibial base component. A verification is made that the target K-wire 151 has not bent or moved and that the absorber unit remains aligned perpendicular to the tibial plateau.

The locking screws 223 are then selected. First, the correct drill bit and threaded drill guide to produce the correct hole size for the 5.0 mm locking screws is also selected. A locking drill guide (not shown) is threaded into the tibial base component 715. A pilot hole is then drilled while ensuring minimal disturbance to the base component. The locking screws are screwed in place to the specified tightness (about 4 Nm torque). This procedure is repeated for the second locking screw 223.

The sheath 225 covering the internal components of the longitudinally compressed absorber 216 is now released from its folded back configuration. First, the absorber 216 is released by cutting structures such as retention sutures or wires (not shown) from the femoral side. This releases both the absorber and retracted ePTFE sheath. The knee should be in extension during absorber release. Next, the sheath is drawn over the mount and adjacent base region until an affixation point of the hole in the sheath aligns with the hole 227 in the base component. A split pin can be inserted into the aligned hole to secure the sheath onto the femoral base component. The procedure is repeated to attach sheath to the tibial base component.

Thereafter, a final verification is conducted. Thus, after placement, the knee should be rotated through deep flexion and full extension. The knee and device should be free to move normally. Motion of the device may be confirmed visually using fluoroscopy. If motion of the knee or device has been compromised in an unexpected manner as a result of the surgery, the device should be removed. If excessive soft tissue binding is observed, widening of the subcutaneous tunneled channel may be necessary.

Finally, the wounds are flushed thoroughly. Each wound is closed layer by layer using physician's preferred technique and suture preference and cover the wound with dressing.

Figure 46:
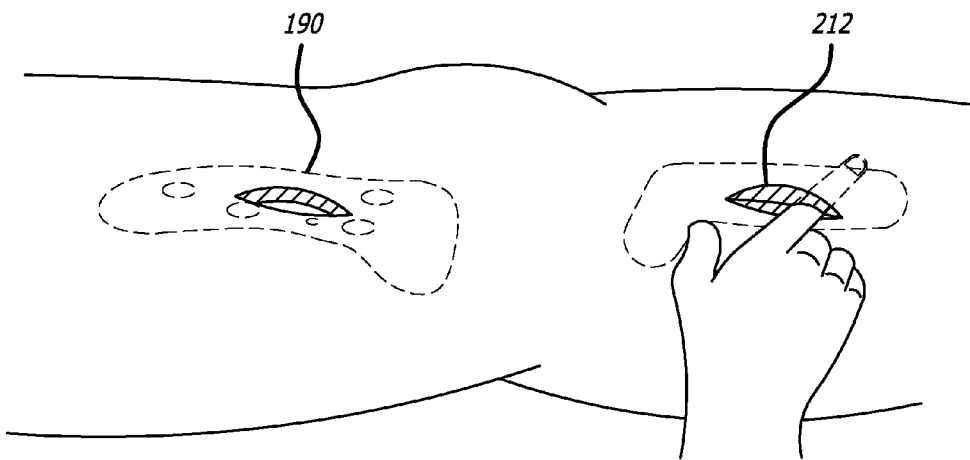
FIG. 46 is a perspective view, depicting physical inspection of a second mounting site at an interventional site of a patient.
Figure 47:
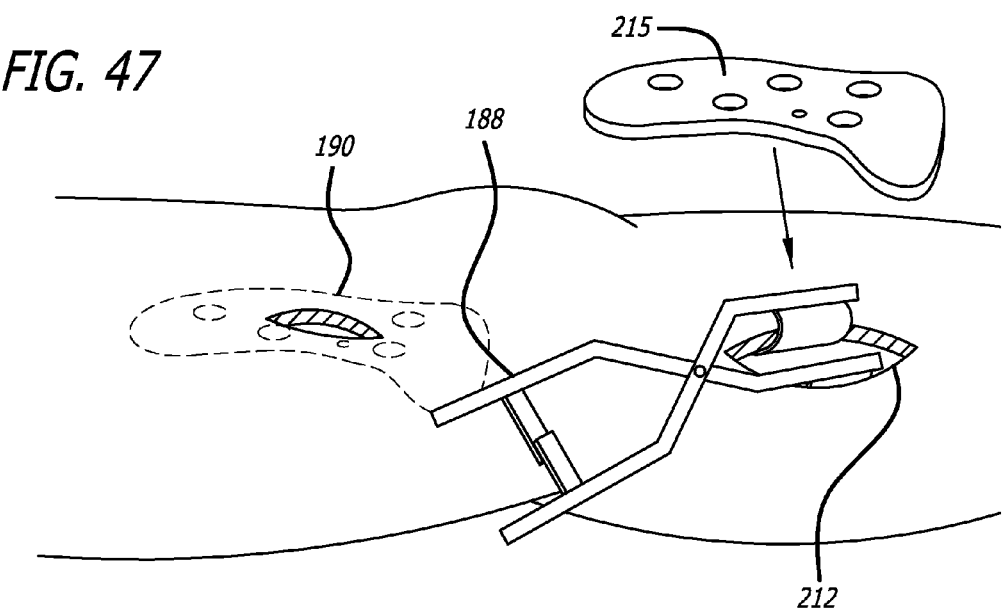
FIG. 47 is a perspective view, depicting a retractor providing access to the second mounting site depicted in FIG. 46.

With reference now to FIG. 46, in another approach, through a second incision 212 on an opposite side of articulating members at the interventional site, the bone is prepared for affixing a second base component 215. Again, the surgeon's finger is used for blunt dissection and along natural tissue planes, and the periostium in the area is removed and displaced. Tissue is scraped to the bone to expose a white, bleeding bone area while being cautious not to disrupt the joint capsule. The retractor 188 can again be used to stretch the tissue forming the opening during implantation site preparation. While holding the incision open, one or more possible second base components 215, here the tibia base component, are placed against the prepared bone to identify a desirable base-to-base component fit. As with all steps of the procedure, remote viewing such as that provided by fluoroscopy is employed to aid in proper sizing and fit.

Figure 48:
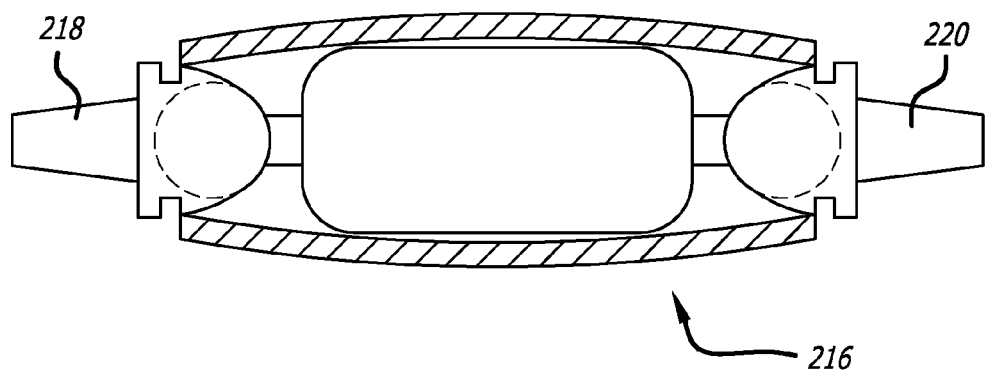
FIG. 48 is a partial cross-sectional view, depicting a dummy link assembly.
Figure 49:
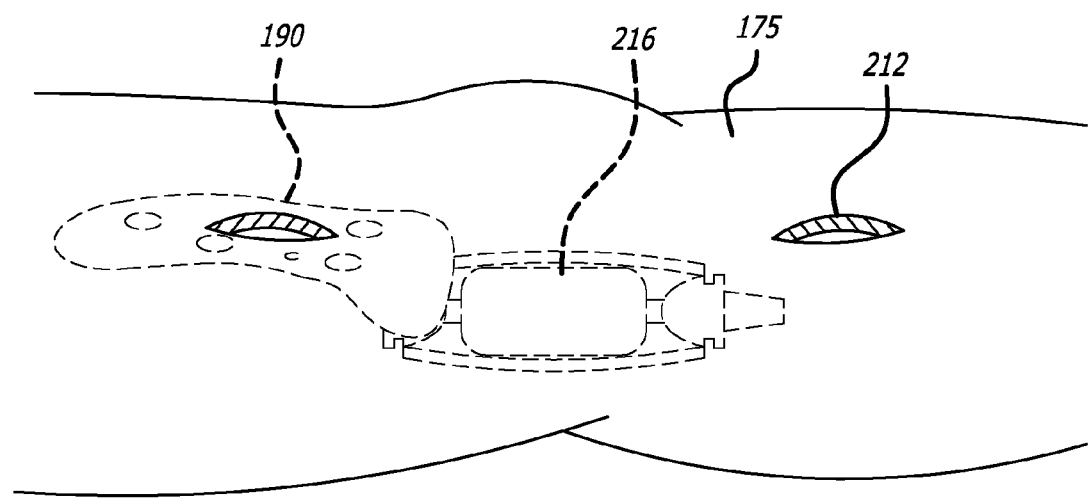
FIG. 49 is a partial cross-sectional view, depicting attachment of one end of the dummy link assembly of FIG. 48 to a first base.
Figure 50:
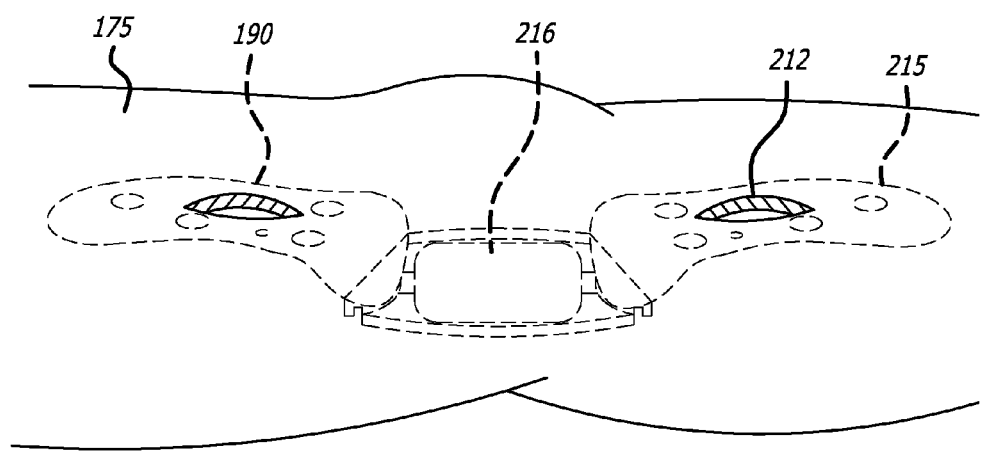
FIG. 50 is a partial cross-sectional view, depicting attachment of a second base component to a second end of the dummy link assembly of FIG. 49.
Figure 51:
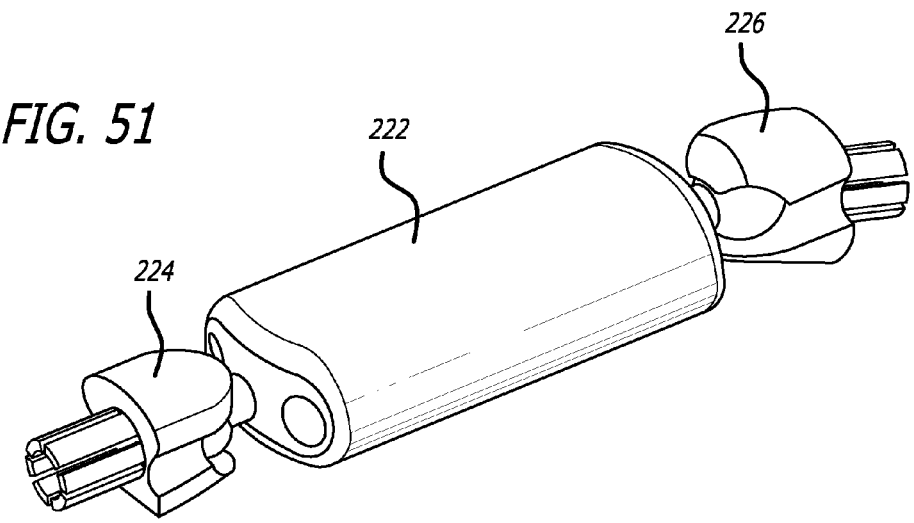
FIG. 51 is a perspective view, depicting a fixed distance link.

Turning now to FIGS. 48-50, in one approach the second base component 215 is removed from the site. A dummy link 216, including first and second tapered ends 218, 220 is inserted through the second incision 212 and is attached to a lower end of the first base 190 (where the K-wire socket structure 208 has been removed). The second base 215, the size and shape of which were previously described, is subsequently inserted through the second incision 212 and placed against bone. Further, the second base component 215 is connected to the dummy link 216 so as to get a sense of the dimensions required for a proper link assembly to be attached to both bases and to span a joint. This step can also help to confirm or select the optimum placement of the second base 215 to bone.

In a related approach (See FIGS. 51-55), a fixed distance link 222 having first and second ends 224, 226 can be utilized for proper link selection and for confirming and selecting the optimum second base position on a bone. Here, the second end 226 of the fixed distance link 222 is releasably attached to a distal end of an insertion and tunneling tool 228. A cover 230 having a tapered profile is placed upon the first end portion of the fixed distance link. A second cover 232 (See FIG. 54) can be additionally provided to facilitate operation of the tunneling tool 228 within patient's anatomy.

Figure 54:
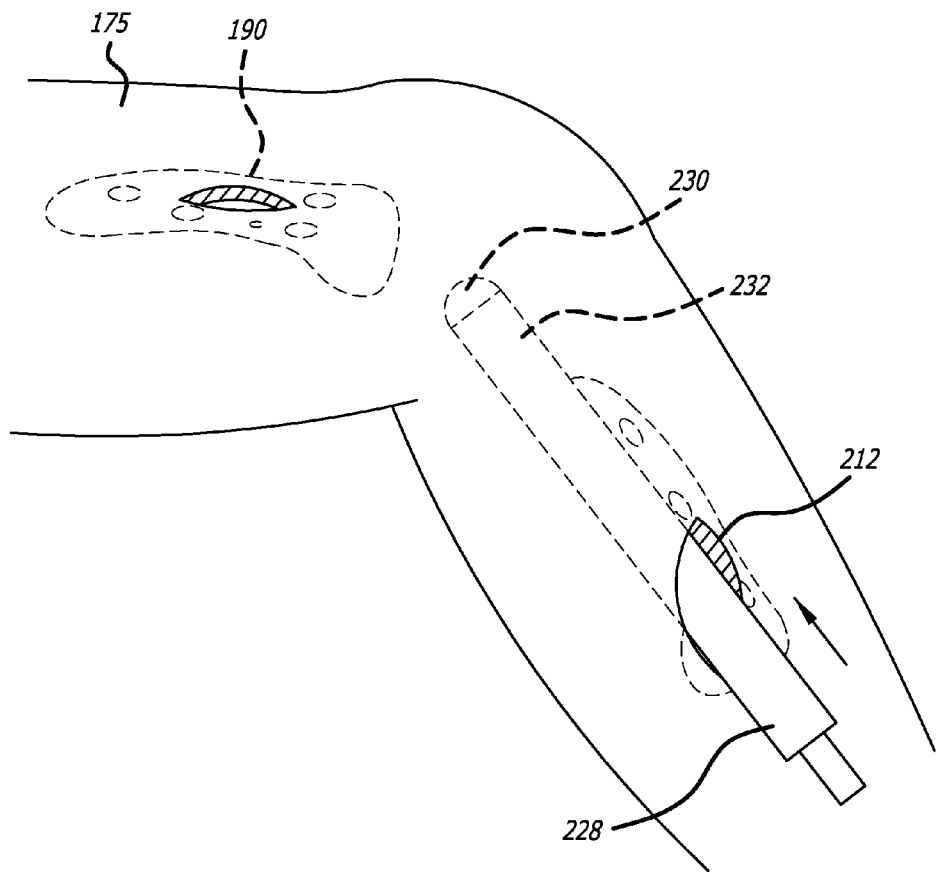
FIG. 54 is a perspective view, depicting use of the assembly of FIG. 53 at an interventional site.
Figure 55:
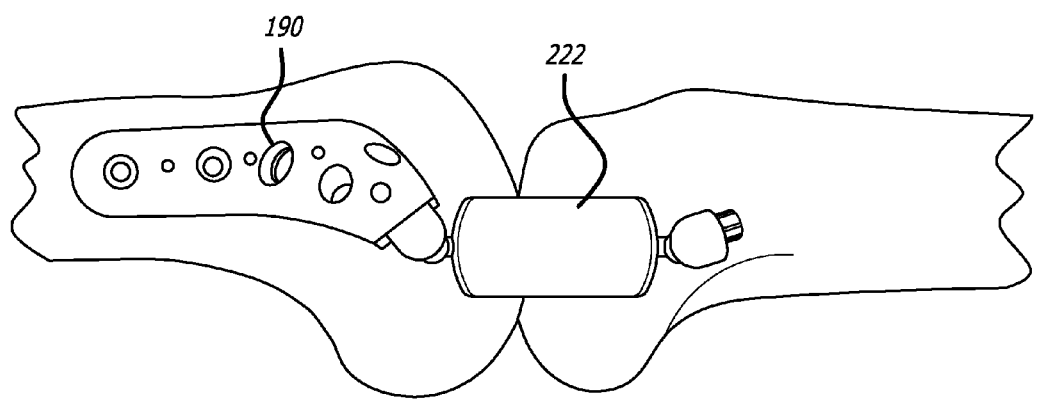
FIG. 55 is a perspective view, depicting placement of the fixed distance link to a first base.

The insertion and tunneling tool 228 is placed within the second incision 212 and is advanced toward the implanted first base component 190 (See FIG. 54). The tool 228 forms a tunnel between mounting locations without causing excessive tissue disruption. At this time, the knee is flexed to ensure the tunnel is established for all possible flexion/extension angles. Once there, the cover 230 is removed from the device and the first end 224 of the fixed distance link 226 is attached to the first base 190. If a second cover 232 is used, it is retracted to expose the fixed link 222. The previously described clamp 206 can be used to accomplish the connection between the components. The tunneling tool 228 is then removed.

Figure 56:
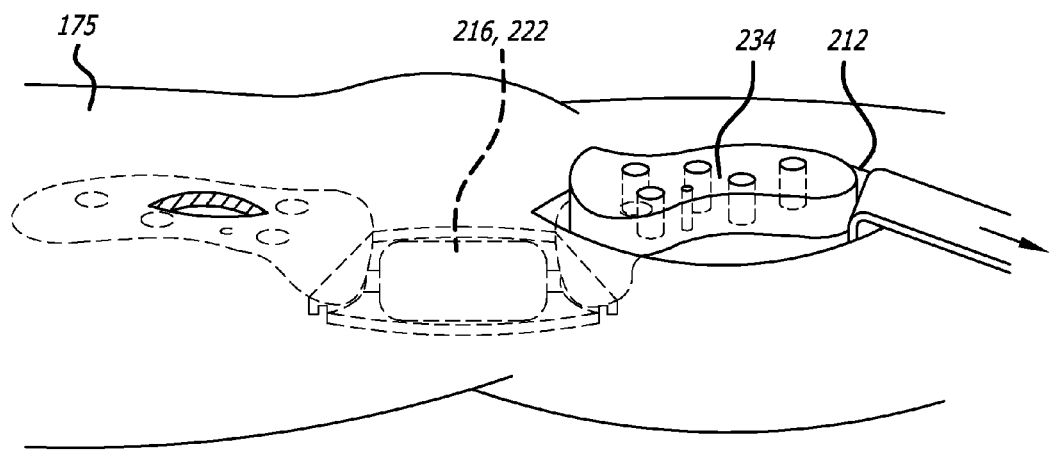
FIG. 56 is a perspective view, depicting use of a drill guide in combination with a second base at an interventional site.
Figure 57:
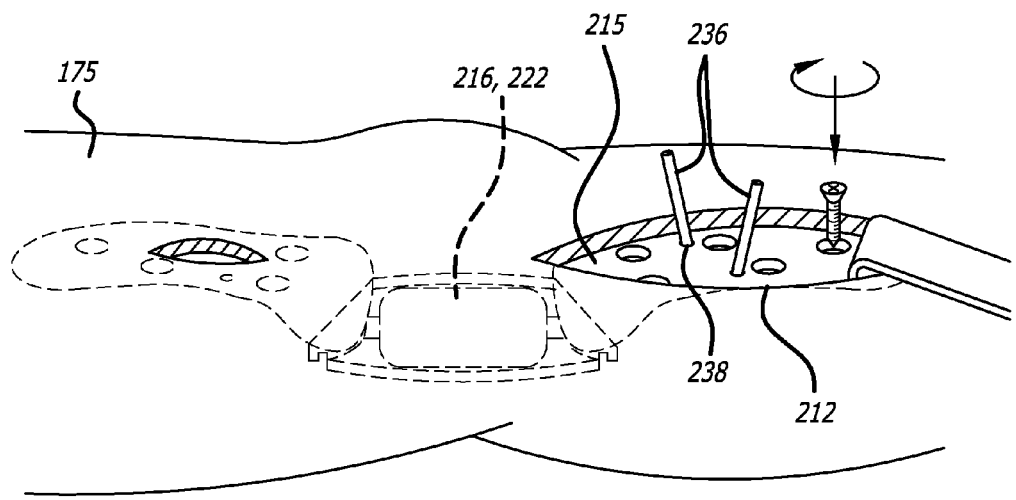
FIG. 57 is a perspective view, depicting fastening the second base at the interventional site.

Whether using the dummy link 216 or the fixed distance link 222, steps are taken to connect the second base to bone (See FIGS. 56 and 57). As was done with the first base 190, a direct guide 234 can where desirable, be placed over the second base component 215. While holding the incision 212 open, support K-wires 236 are drilled through the guide 234, second base through holes 238 and into bone. After removing the guide 234, compression screws or other fasteners are used to fix the second base component 215 to the bone. Verification of placement is confirmed through remote imaging. Finally, the K-wires 236 are removed from the second base component 215.

Figure 58:
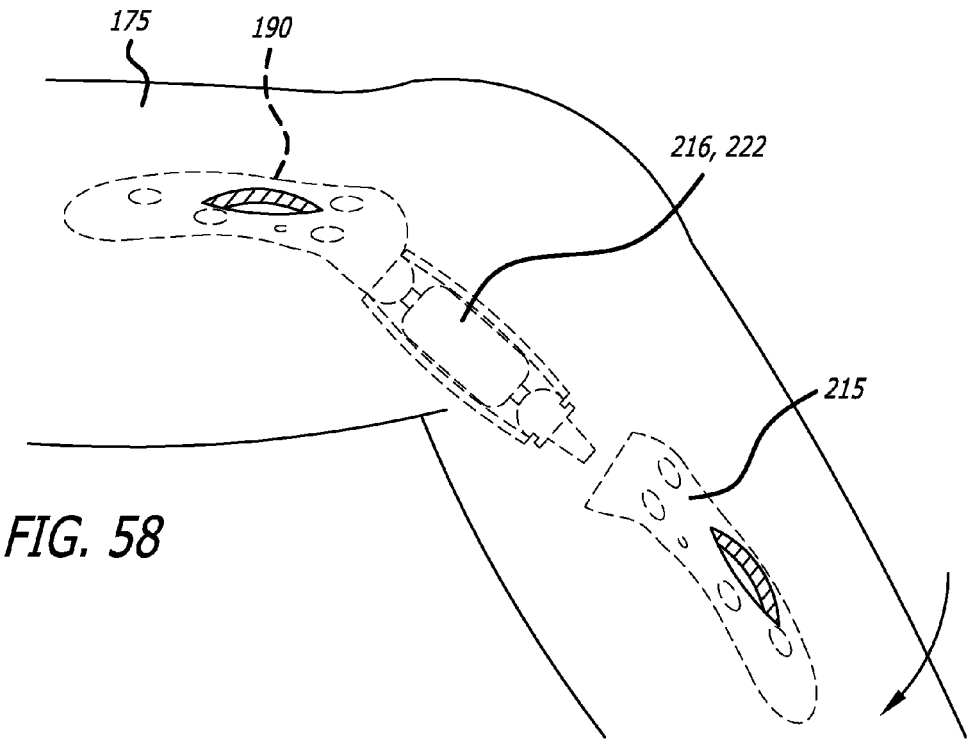
FIG. 58 is a partial cross-sectional view, depicting rotation of one articulating body member.
Figure 59:
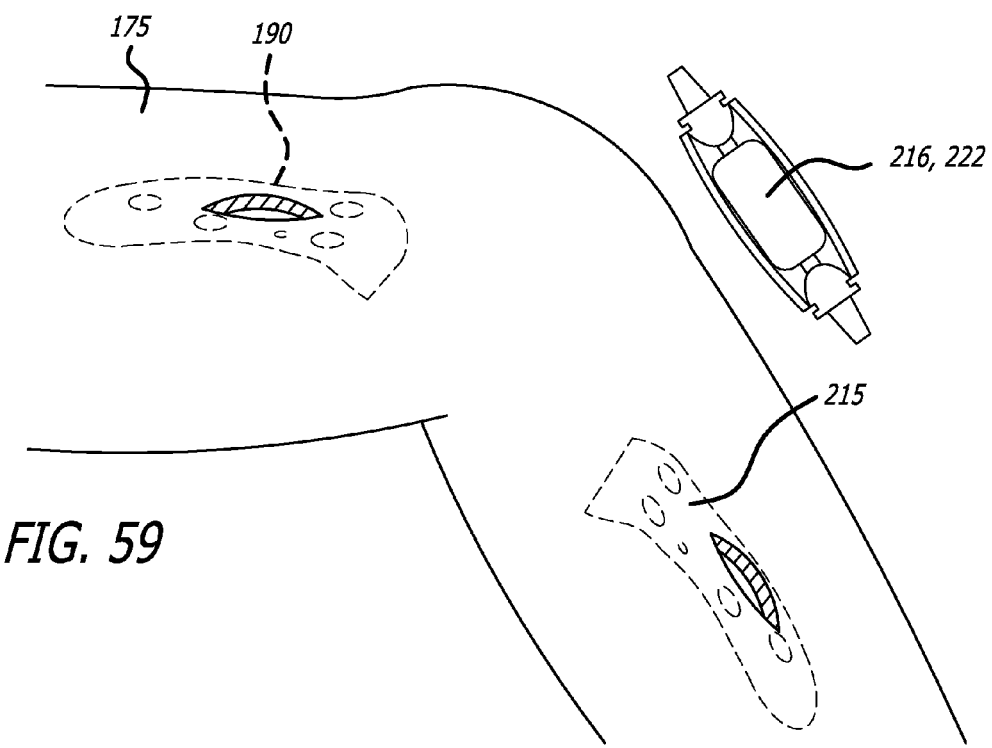
FIG. 59 is a partial cross-sectional view, depicting removal of a dummy link from the interventional site.
Figure 60:
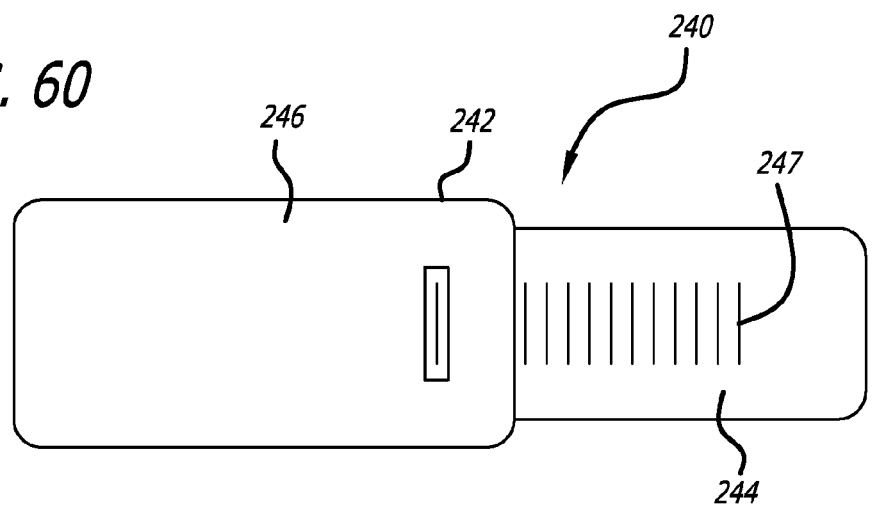
FIG. 60 is a top view of a base locating tool.
Figure 61:
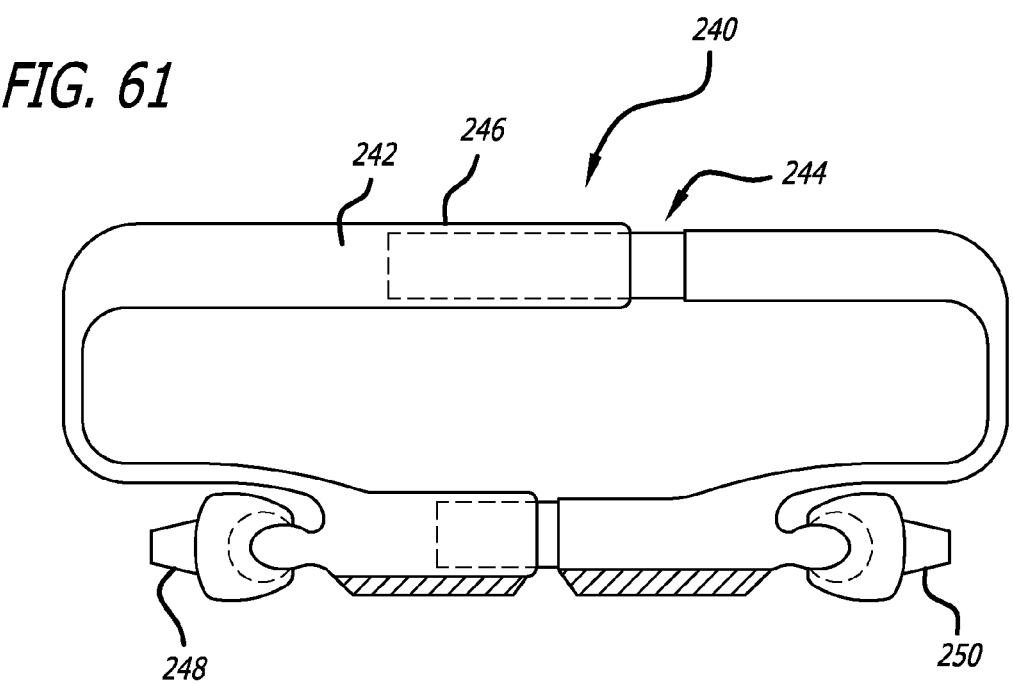
FIG. 61 is a side view, depicting the base locating tool of FIG. 60.
Figure 62:
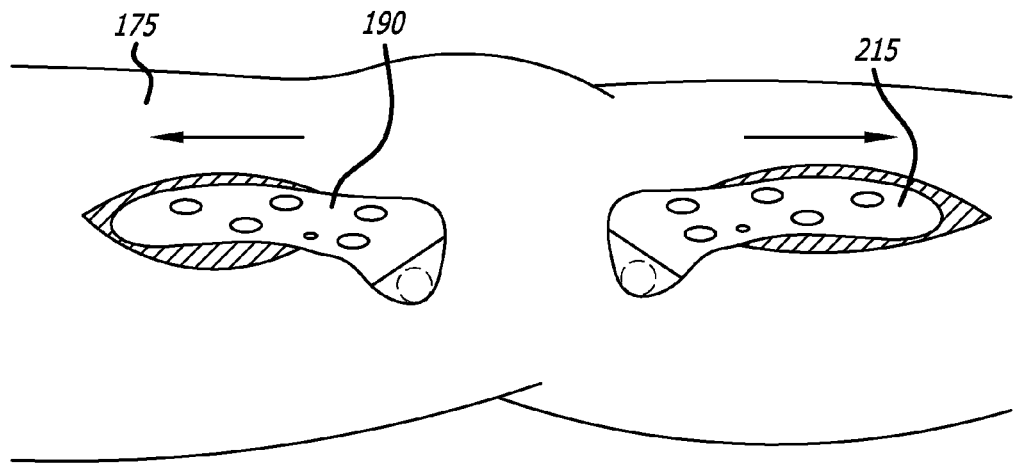
FIG. 62 is a perspective view, depicting a first step in a method involving the base locating tool.

As shown in FIGS. 58 and 59, after removing structure maintaining the position of the leg 175 in an extended position, the lower portion of the leg is flexed so that it forms an angle with the upper leg. The ends of the dummy or flexed length link 216, 222 are then disengaged from the bases 190, 215 and the link is removed from the interventional site.

Figure 63:
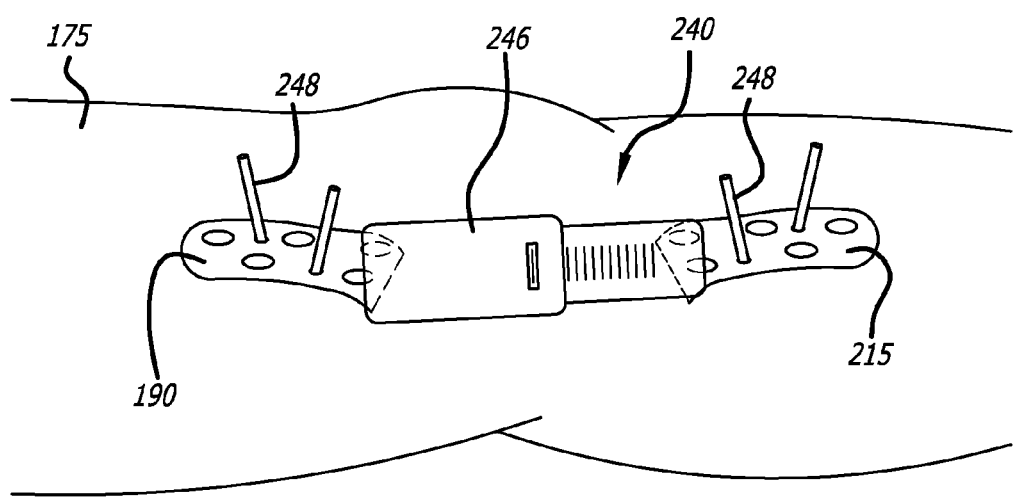
FIG. 63 is a perspective view, depicting a subsequent step involving the base locating tool.
Figure 64:
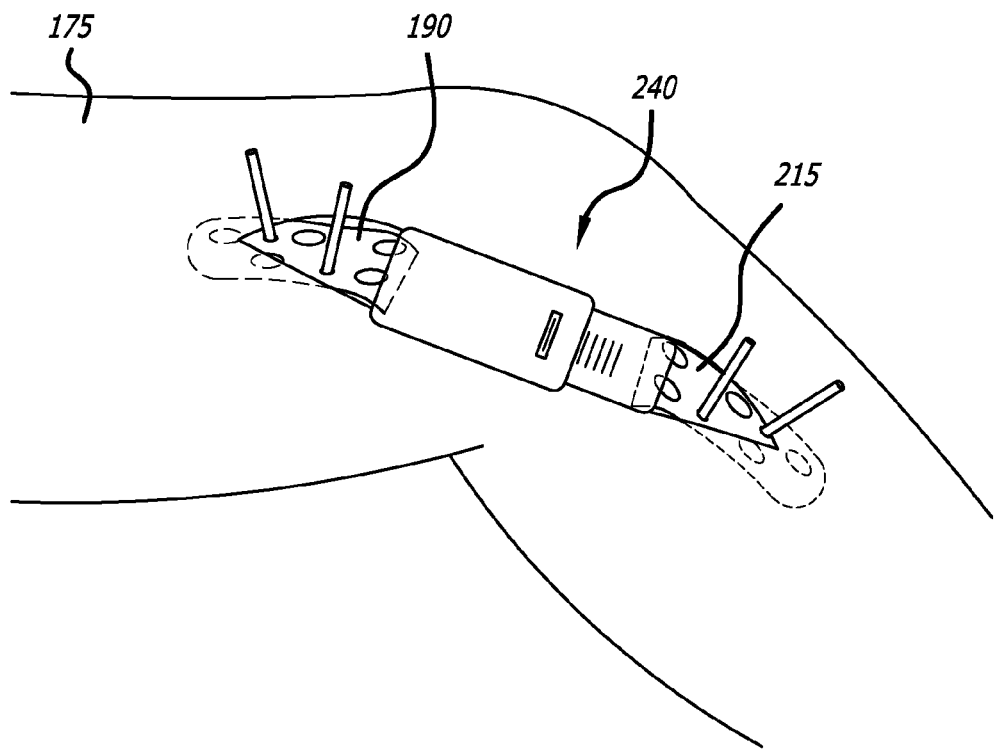
FIG. 64 is a perspective view, depicting yet another step involving the base locating tool.
Figure 65:
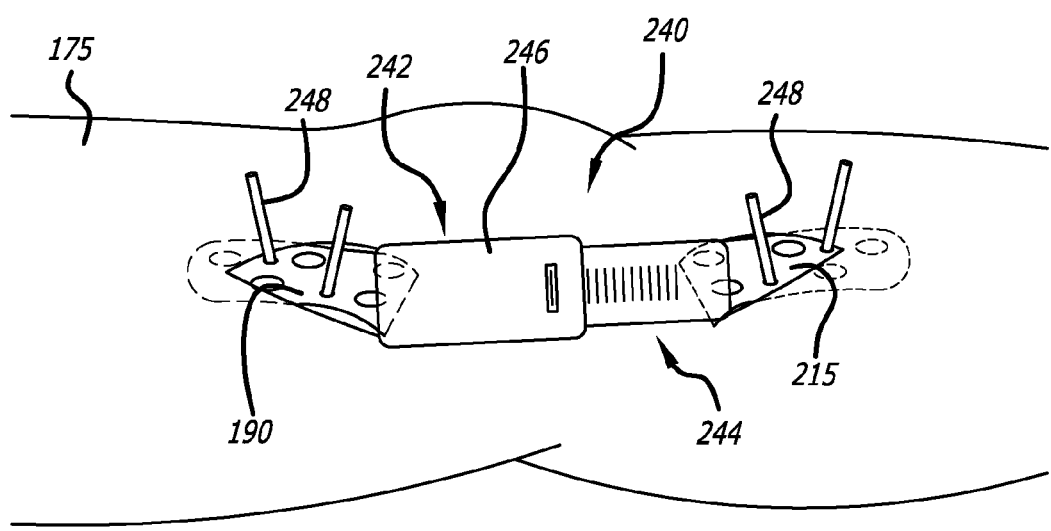
FIG. 65 is a perspective view, depicting further use of the base locating tool at an interventional site.
Figure 66:
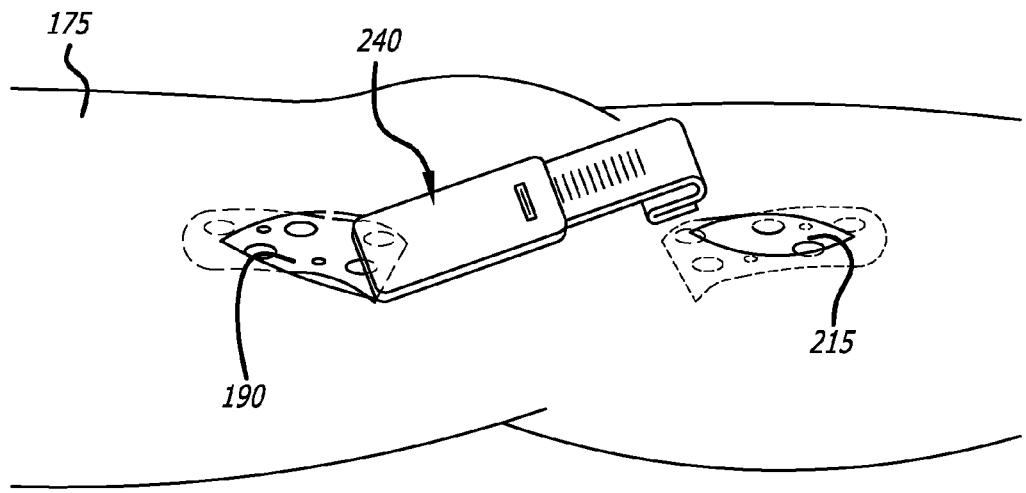
FIG. 66 is a perspective view, depicting removal of the base locating tool from an interventional site.
Figure 67:
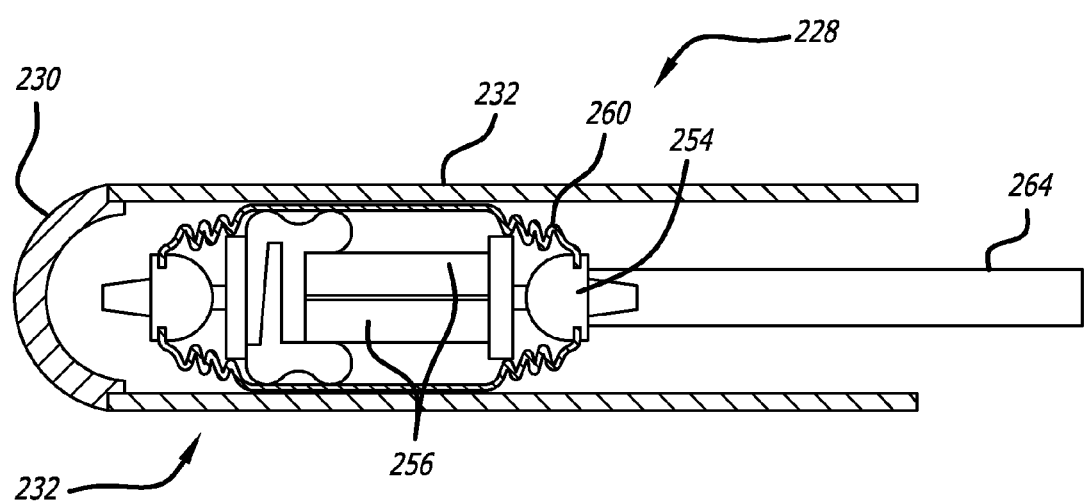
FIG. 67 is a cross-sectional view, depicting a link stored within a guide tube housing.
Figure 68:
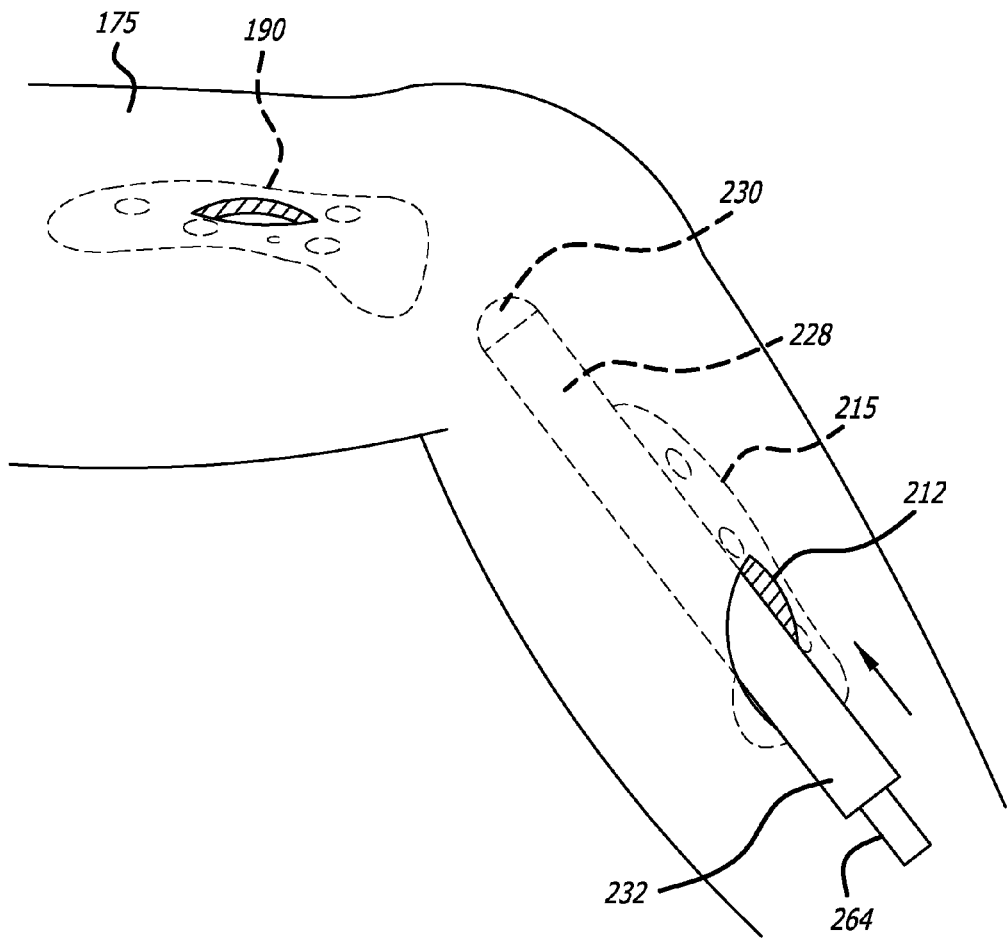
FIG. 68 is a partial cross-sectional view, depicting use of the guide tube assembly of FIG. 67 at an interventional site.
Figure 69:
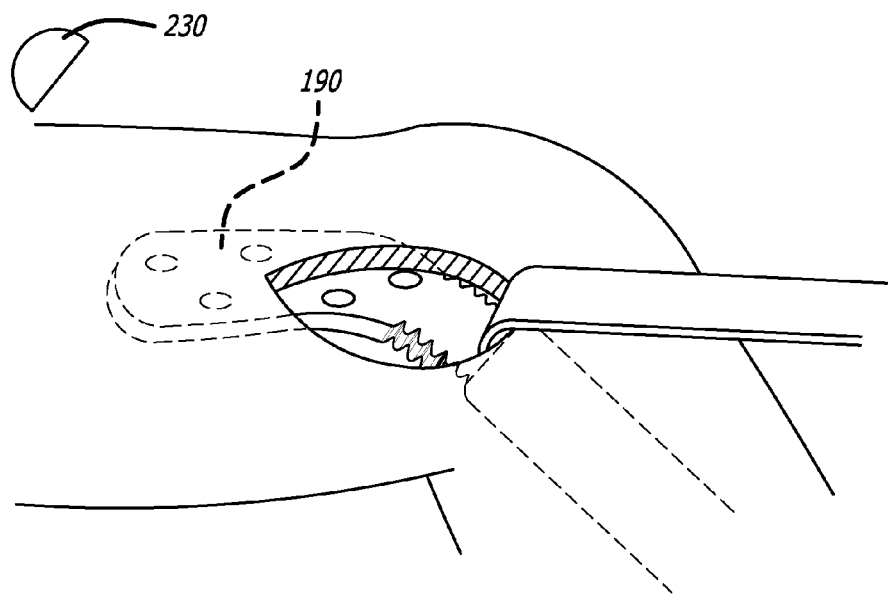
FIG. 69 is a partial cross-sectional view, depicting an attachment of the link assembly to a first base component.
Figure 73:
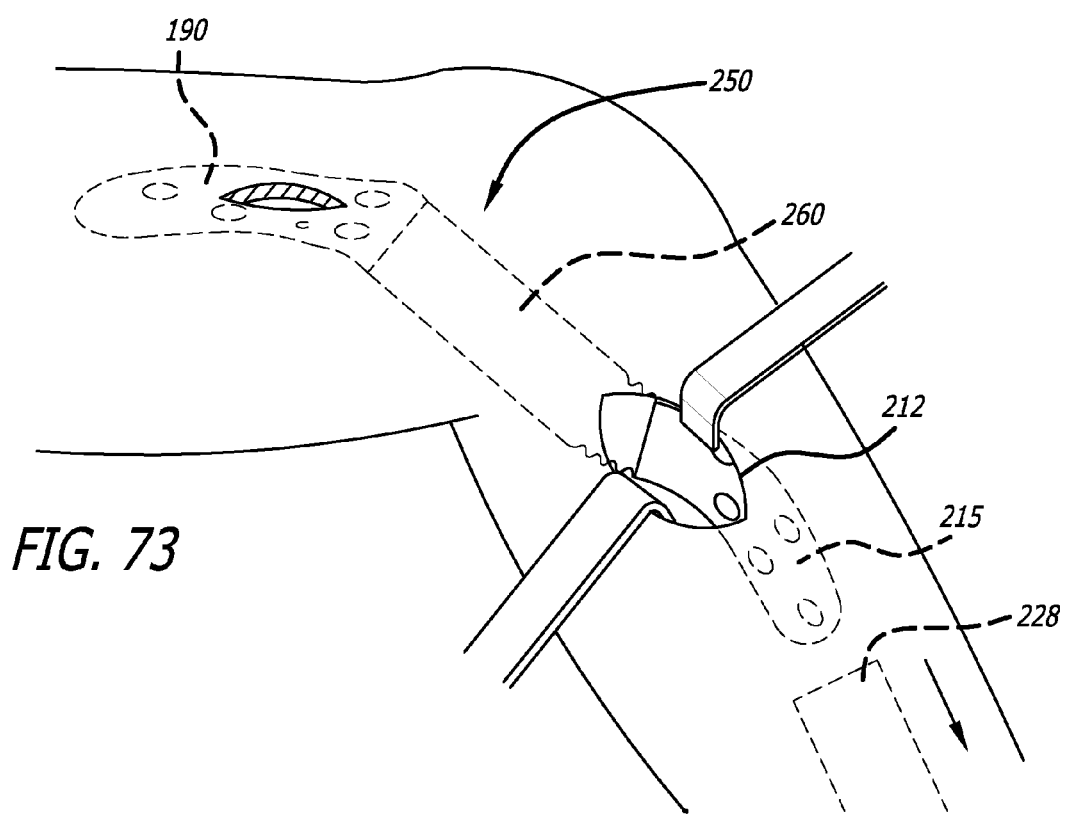
FIG. 73 is a partial cross-sectional view, depicting placement of a portion of a sheath about a portion of a second based component.

With reference now to FIGS. 60-66, one alternative or complementary approach to sizing and selecting a link component is described. A base location tool 240 including a pair of sliding halves 242, 244 which form a hoop structure can be placed between the first and second base components 190, 215. This tool 240 can be used with bases that have been fixed to bone or prior to such fixation. During use, a top side 246 resides on the outside of the patient's skin. The top portion 246 can include indicia 247 for identifying with certainty the space between the bases or the length of a proper link. A bottom portion includes a pair of oppositely located and spaced connection structure 248, 250. The spaced connecting structure 248, 250 are sized and shaped to releasably engage a respective one of the first and second bases 190, 215 and to permit a limited range of motion between the tool and bases. It is also contemplated that the height of the base locating tool can be modified for variations in patient skin and tissue thicknesses.

Where the bases are yet to be fixed to bone, K-wires 248 can be used to temporarily fix the bases in place (See FIG. 63). Various sized and shaped bases 190, 215 can be used to achieve proper fit. Next, the patient's anatomy, here the limbs forming the knee, are flexed to record the maximum link extension required. A check for bending of the components is made at this time both when the anatomy is in its flexed (FIG. 64) and in its extended position (FIG. 65). The bases are then affixed to bone (if not already done so) and the base locator tool (and K-wires 248) is removed from the site. In this way, proper position of the bases 190, 215 and/or proper selection of a link is accomplished.

Turning now to FIGS. 67-73, once proper sizing of a link component 250 has been made, an insertion and tunneling tool 228 is employed to complete the assembly of a mechanical energy absorbing device at the implantation site. The mechanical energy absorbing device can be held in a longitudinally compressed condition by wires or other delivery structures. Such a wire or other structure can operate on the spring assembly of the device or can be attached to other structure to accomplish the desired compression. Although different embodiments can be used, here, the link assembly 250 includes first 252 and second 254 ends each with an articulatable tapered post. The posts are each sized to fixedly engage one base component 190, 215. The two part base/tapered post mounts provide a method for good attachment of the base to the bone and a more simple surgical technique for installing the link assembly. It also allows the sheath and/or wear components of the link/mount assembly to be removeable and/or replaceable without removing or replacing the base components. It further allows the wear components of the link/mount assembly and the base components to be different materials. For example, the base components can be titanium or titanium alloy which promote osteo-integration and the wear components can be much harder materials such as cobalt chrome (e.g., Biodur CCM Plus), ceramic, or other durable materials that produce a minimal amount of particulate material or, if particulate material is generated, the smallest size of particulate material. The link assembly also includes energy absorbing and manipulating structure 256 as well as an extendable sheath 260 extending between a pair of spaced socket locks 262.

The tunneling tool 228 further includes a push rod 264, a distal end of which releasably engages and stabilizes the link assembly 250 through a connection with the second tapered post structure 254. In use, the tunneling device 228 loaded with a link assembly 250 is placed within the second incision 212 (an approach through the first incision can also be employed with a link assembly loaded in an opposite direction) and advanced as described above previously toward the first base component 190. After removing the distal cover 230, the first end 252 of the link assembly is placed into complementary structure 266 of the base component (See FIG. 70). To accomplish this connection, clamp 206 (See FIG. 27) or a similar tool is utilized. Additionally, a plastic barrier can be temporarily inserted to keep the soft tissues beneath the joint from interfering in connection of the link assembly and sheath to the base component. An adjacent socket lock 262 (See FIG. 71) is then manipulated to permit extending the sheath (See FIG. 72) over a portion of the first base component 190. Similar steps are taken to connect and cover the second base component 215 to the link assembly 250. Inspections are made to ensure proper connections and the tunneling tool is then removed from the site.

In an alternate approach, after creating a tunnel, the link assembly can be placed in a sheath like sheath 232 of tunneling tool 228 having a leading end closed by a suture (not shown). The sheath with a leading suture can be inserted through the second incision 212 and then through the space created between the incision 190, 232, and thereafter, advanced toward the first incision 190 by pulling on the lead suture. It is also contemplated that one or more colored sutures can be employed for different functions, such as pulling the sheath through the site and holding a link assembly in a compressed state. In this way, the sheath acts like a protective poncho facilitating the advancement of the link assembly, being held in a longitudinally compressed state, through the interventional space. Subsequently, cutting the suture can release the link from the sheath so that the sheath can be removed from the site. In the event multiple colored sutures are employed, a second suture can be severed when desired to permit the link device to assume a longitudinally expanded state.

Figure 74:
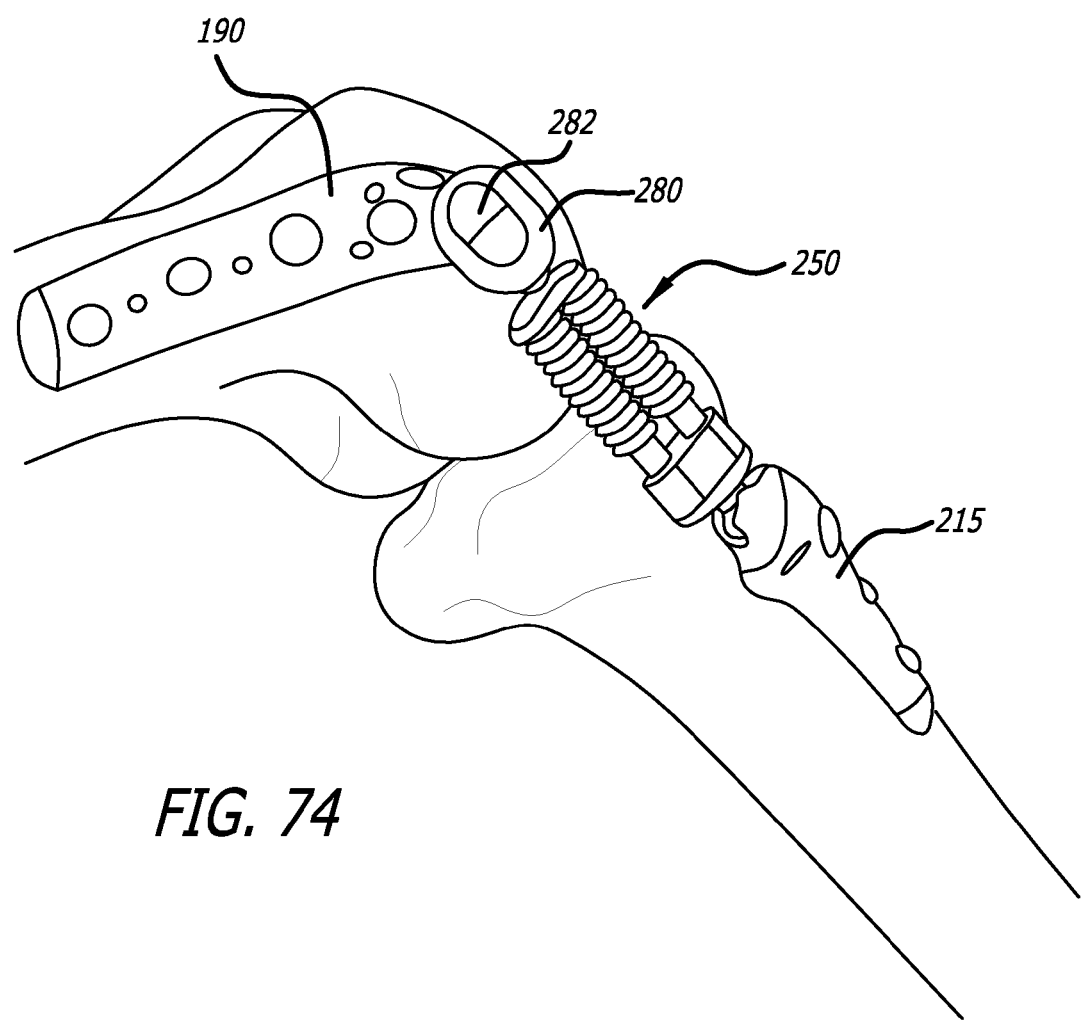
FIG. 74 is a perspective view, depicting a tool for temporarily attaching to a mount.
Figure 75:
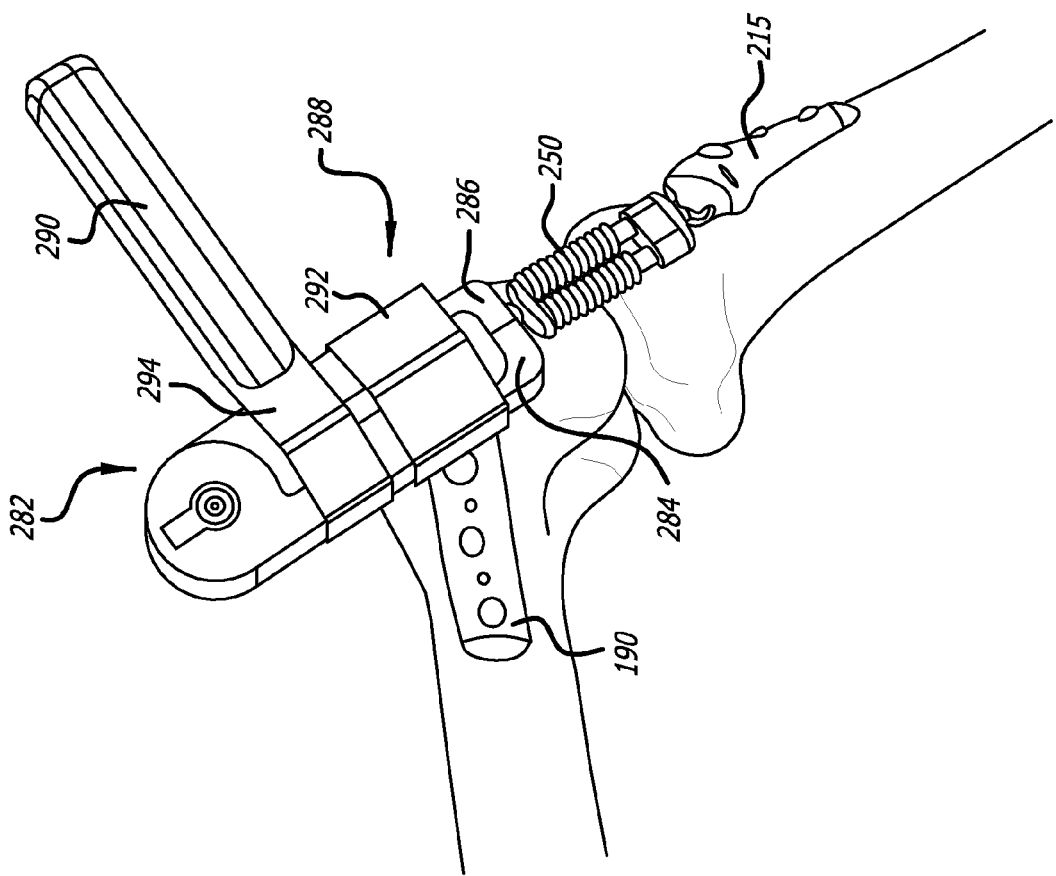
FIG. 75 is a perspective view, depicting a tool for locking a link assembly to a mount.
Figure 76:
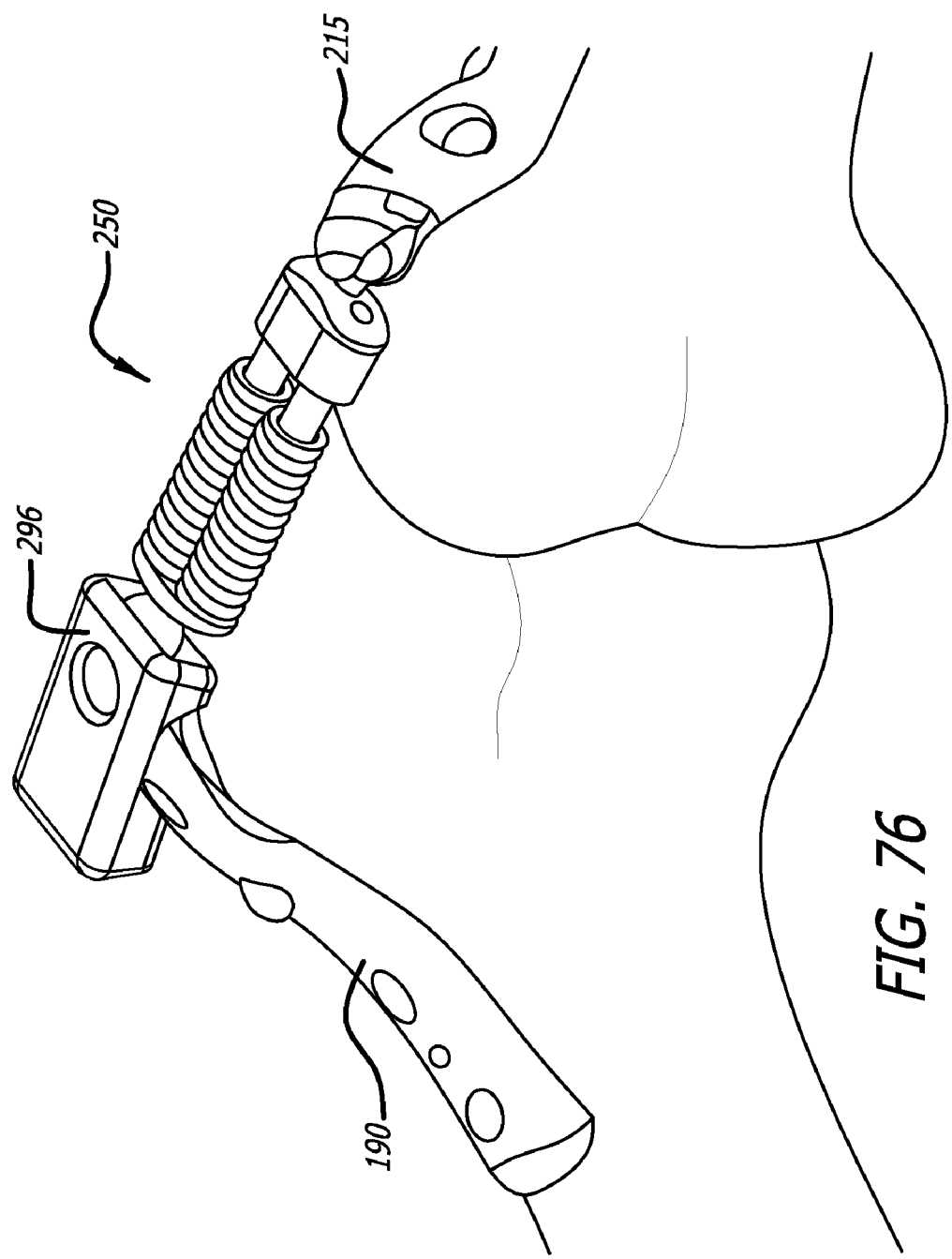
FIG. 76 is a perspective view, depicting another tool for accomplishing attachment of a link to a base.

Moreover, various tools can be employed to aid in configuring a link assembly 250 between the bases 190, 215. As shown in FIG. 74, a socket holder 280 including a ringlet 282 is used to temporarily attach the link assembly 250 to a mount of the femoral base 190. The ringlet can be pulled by hand or another tool through a tunnel formed beneath the skin between the bases 190, 215 or alternatively simply used to temporarily attach the link to the mount of the base. After temporarily attaching the link assembly 250 to the femoral base 190, the temporary socket holder is replaced by a socket holder assembly 282 (See FIG. 75) which includes clamping arms 284, 286 each having a terminal end which engages opposing sides of a mount of a femoral base assembly. A taper lock tool assembly 288 is configured about the clamping arms 284, 286. The taper lock tool assembly 288 includes an activation arm 290 and a taper lock pusher block 292, each of which are guided by a pair of spaced shafts 294. Actuation of the activation arm results in the pusher block 292 accomplishing a locking engagement of the link assembly 250 to the femoral base 190. In yet another approach, temporary attachment of the link assembly 250 to the femoral base 190 as well as the advancement of the link assembly 250 within a patient's skin can be achieved by using the socket hook 296 shown in FIG. 76.

Figure 77:
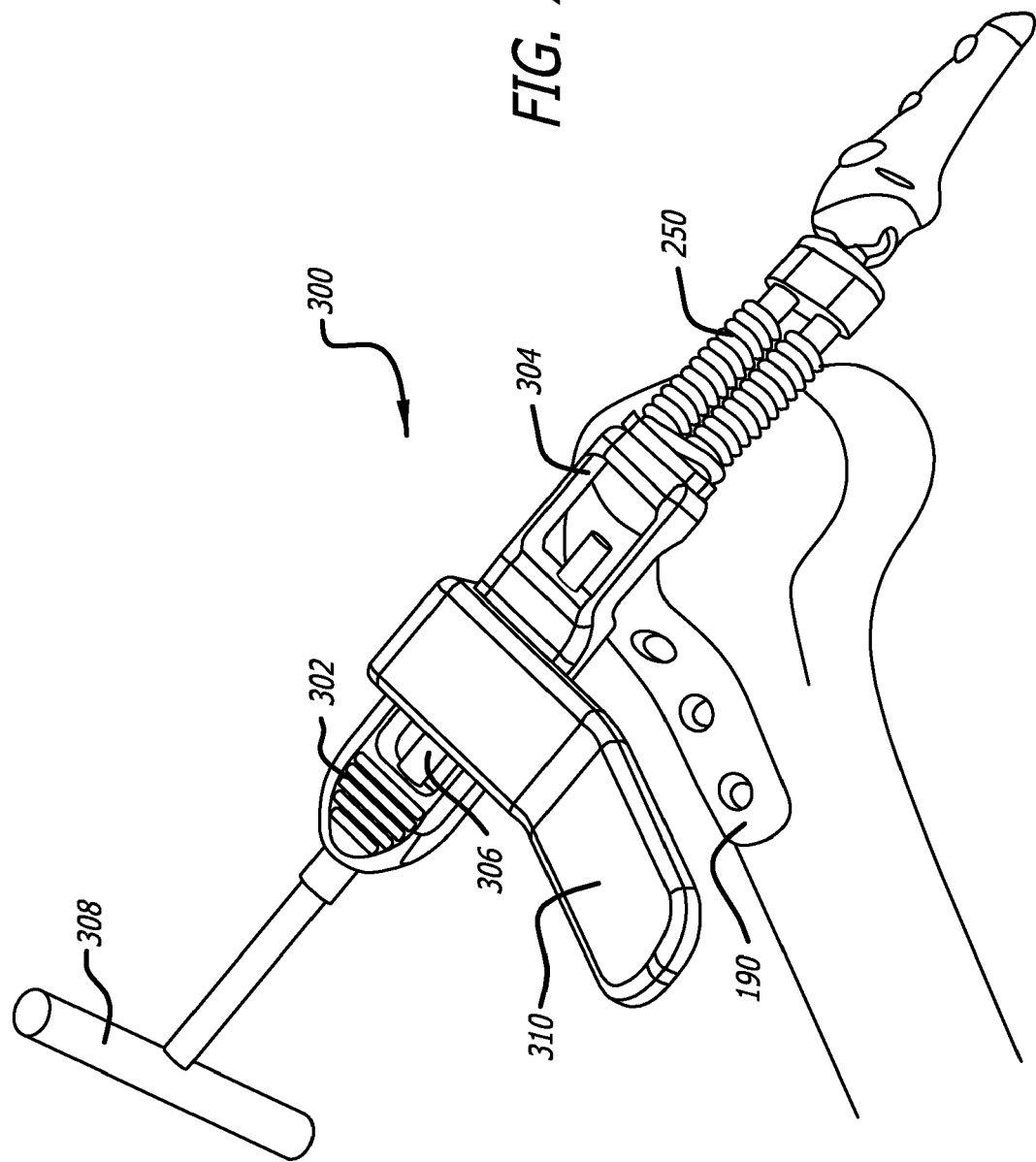
FIG. 77 is a perspective view, depicting an additional approach to a tool for assembling a mechanical energy absorbing apparatus.
Figure 78:
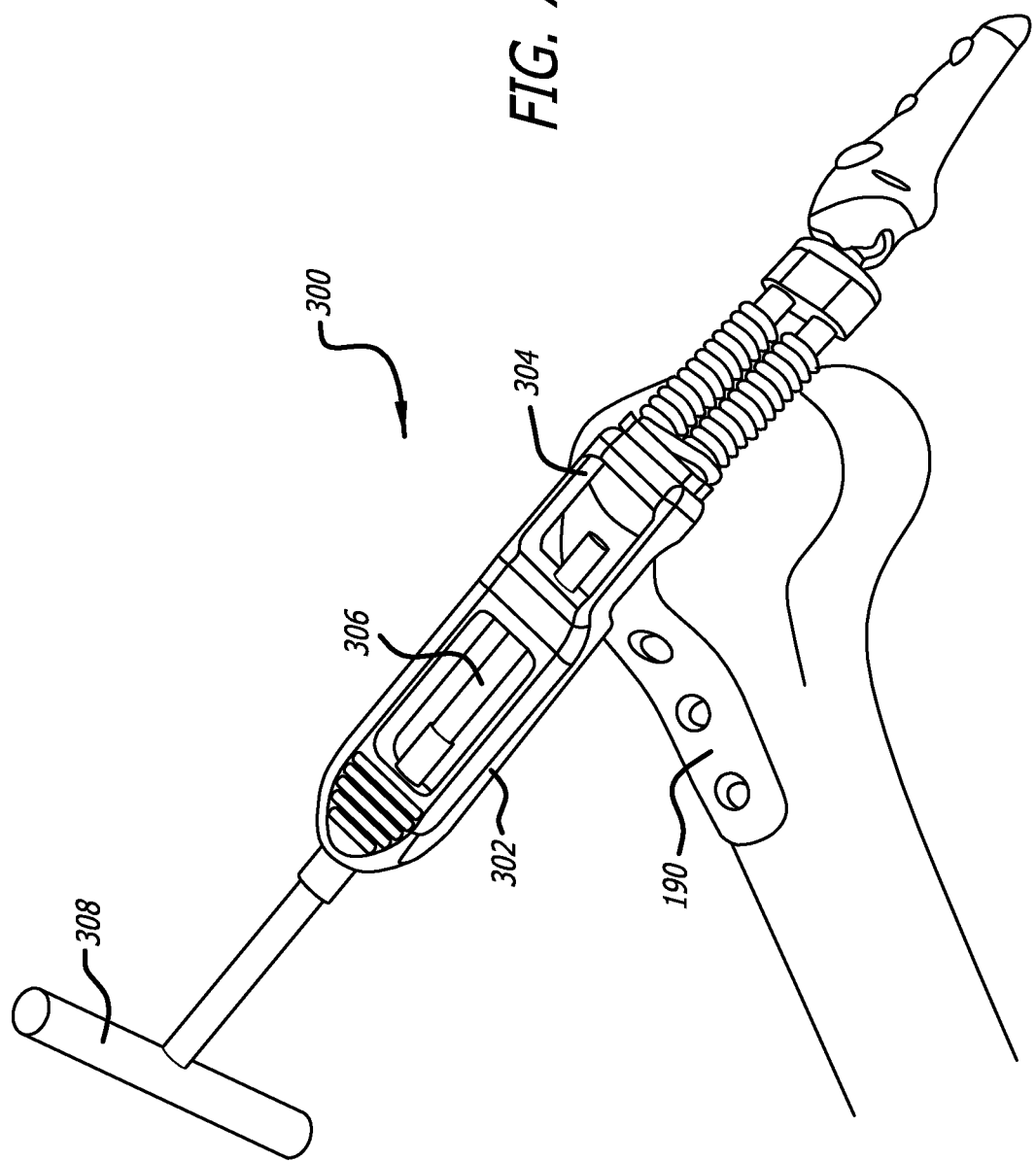
FIG. 78 is a perspective view, depicting the tool of FIG. 77 with a handle removed.
Figure 79:
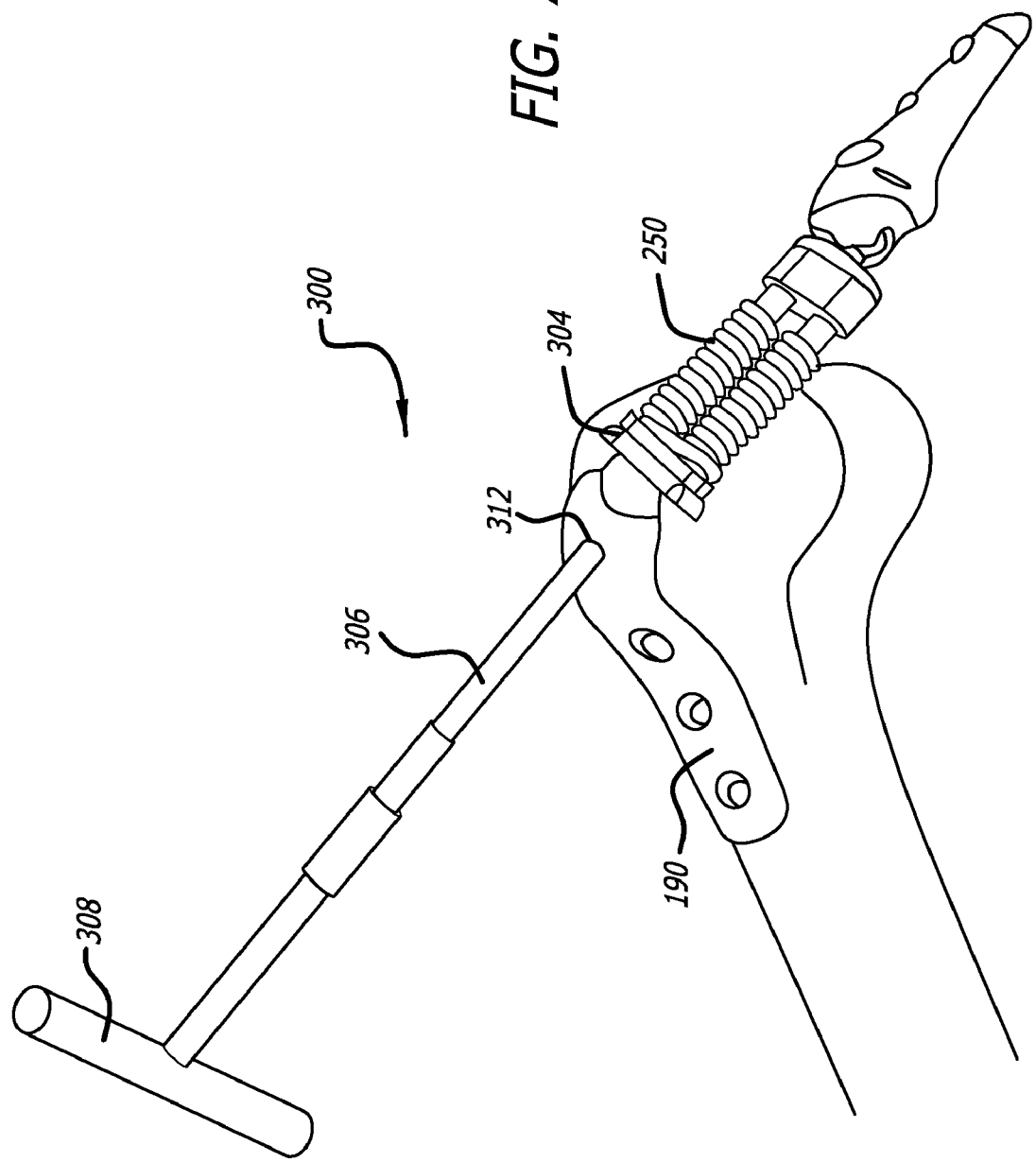
FIG. 79 is a perspective view, depicting the tool of FIG. 78 with a socket loading tool removed.
Figure 80:
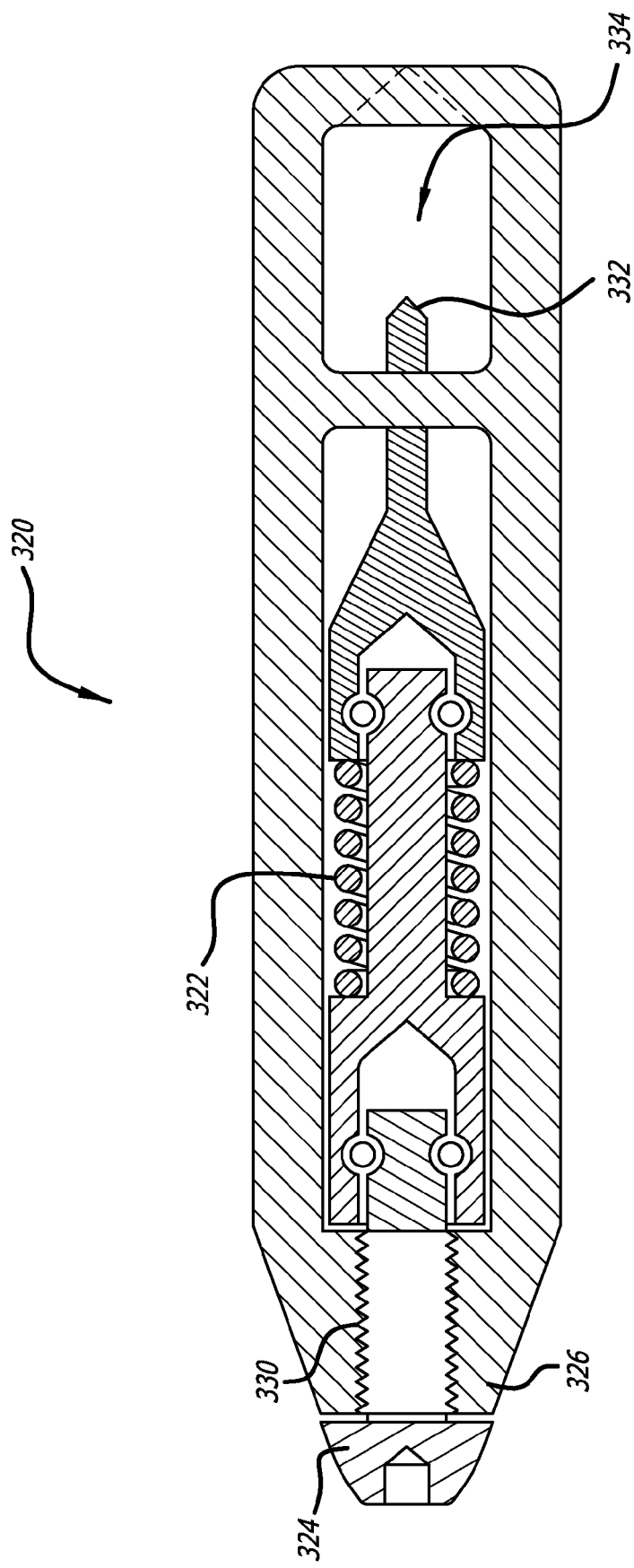
FIG. 80 is a non-sectional view, depicting another approach to an attachment tool.

Turning now to FIGS. 77-79, another locking tool 300 is illustrated. Here, the tool 300 includes a socket loader 302 having a lead end configured to graspingly engage a mount 304 of a link assembly 250. The socket loader 302 is sized and shaped to receive a shaft 306 having a threaded portion for engagement with complementary structures formed in the socket loader. A back end of the shaft 306 includes a hex structure configured to receive a hex drive component 308. In order to stabilize the tool 300, a counter torque handle 310 sized to grasp the socket loader 302 is further provided. In use, the socket holder 302 is placed into engagement with a mount 304 and the hex drive 308 is turned to advance the shaft distally. As the shaft 306 is advanced, it engages a recess 312 or other convenient structure of the base 190. From this anchor position, the mount 304 is effectively drawn into locking engagement with the base 190.

In an alternate approach, a locking tool 320 can further include such structure intended to prevent damage to an implant should a physician attempt to over tighten or use excessive force to accomplish a locking engagement between implant components. Thus, the tool 320 can embody a Belleville spring stack 322 configured to compress enough so that a shoulder on a hex 324 will advance against a body 326 of the tool 320 and thus absorb the excess forces rather than allow the same to be applied against the implant. Accordingly, turning the hex 324 will advance a threaded shaft 330 within the tool 320 to thereby move a top of a base/mount engagement member 332 against a mount placed within a recess 334 sized for receiving the mount. Again, any excessive forces employed to accomplish a locking engagement between implant components will be blocked by the Belleville stack 327.

Figure 81:
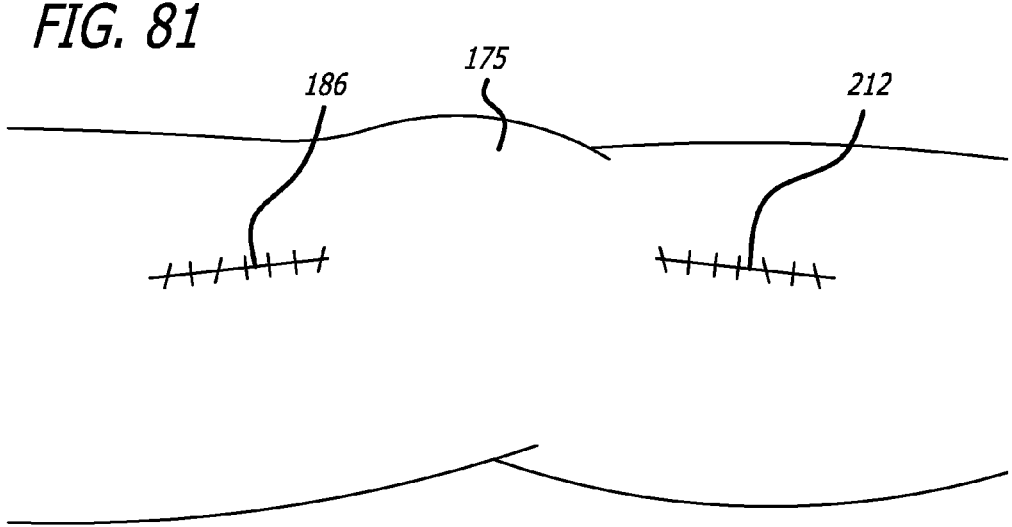
FIG. 81 is a perspective view, depicting an exterior of body anatomy having mechanical energy absorbing apparatus implanted therein.

Once the physician is satisfied with the implantation, the first 180 and second 212 incisions made at the interventional site are then closed (See FIG. 81) and post-surgery clean-up is performed. In instances where it is desirable to remove or replace the link across two previously implanted base components two incisions are made above each end of the absorber and tissue is retracted to expose the absorber base coupling area and the sheath is retracted or cut back. Using a removal tool the absorber is decoupled from each base component without permanent deformation of the base component and the absorber removed from within the tissue tunnel. Another absorber unit may be coupled to the remaining bases using previously described methods. In instances where it is desirable to remove the base components in addition to the absorber, the screws are removed and base components lifted from the bone surface. In this scenario the device assembly including absorber may be removed as a single unit.

In the event that it becomes necessary to remove the device the following should be considered. To remove the kinematic absorber unit, a removal instrument is inserted into the base socket access port. The instrument is levered to press on locked portion of the implant. Once this step is completed on both the femoral and tibial bases, the absorber unit can be removed.

Stimulation of the interventional sites in combination with implantation of a mechanical energy absorption device may facilitate treating conditions affecting a body joint, such as osteoarthritis, via a number of different mechanisms. Such stimulation means can form an integral part of the mechanical energy absorbing apparatus or can define separate structure.

In a first approach, electrical stimulation may block the perception of pain associated with osteoarthritis. Electrical stimulation of a joint affected by osteoarthritis, an intraarticular joint space of the affected joint, one or more peripheral nerves that innervate the affected joint, the spinal cord, spinal segments supplying somatic sensation at the affected joint, spinal segments supplying sympathetic control of the affected joint, the nucleus gracilis, one or more cranial nerves, one or more areas in the brain, the hypothalamus, the thalamus, the motor cortex, and/or any other stimulation site may effectively inhibit or relieve pain associated with osteoarthritis and help with the efficacy of the implantation procedure.

Another contemplated approach involves the infusion of drugs, chemicals, and/or other substances designed to or known empirically to treat osteoarthritis. Infusing drugs, chemicals, and/or other substances directly into the local area of an affected joint or into nerves and/or arteries supplying the joint may allow relatively high therapeutic doses. Thus, the infusion of drugs, chemicals, and/or other substances into a joint affected by osteoarthritis, an intraarticular joint space of the affected joint, an artery supplying the affected joint, one or more peripheral nerves that innervate the affected joint, the spinal cord, spinal segments supplying somatic sensation at the affected joint, spinal segments supplying sympathetic control of the affected joint, the sympathetic ganglia, the nucleus gracilis, one or more cranial nerves, one or more areas in the brain, the hypothalamus, the thalamus, the motor cortex, and/or any other stimulation site may also effectively facilitate treatment.

Stimulation can also involve proprioceptive pathways supplying a joint with osteoarthritis. Stimulation of proprioceptive pathways supplying a joint may improve patient proprioception through the phenomenon of stochastic resonance. Accordingly, stimulation of a joint affected by osteoarthritis, an intraarticular joint space of the affected joint, one or more peripheral nerves that innervate the affected joint, the spinal cord, spinal segments supplying sympathetic control of the affected joint, the nucleus gracilis, one or more cranial nerves, one or more areas in the brain, the hypothalamus, the thalamus, the motor cortex, and/or any other stimulation site may also lead to higher incidence of efficacy.

Moreover, modulating the blood supply to a joint or direct stimulation of the arteries supplying an affected joint may have beneficial results. Therefore, stimulation of an artery supplying the affected joint, one or more peripheral nerves that innervate the affected joint, the spinal cord, spinal segments supplying somatic sensation at the affected joint, spinal segments supplying sympathetic control of the affected joint, the sympathetic ganglia, the nucleus gracilis, one or more cranial nerves, and/or any other stimulation site is contemplated. Alternatively, the blood flow into a joint may be decreased by exciting sympathetic drive responsible for generating vasoconstriction. Decreasing the blood flow into a joint may reduce swelling in the affected joint and aid in joint improvement.

Therefore, the present disclosure provides a number of ways to treat body tissues and in particular, to implant absorb energy or manipulate forces to reduce pain. Various aspects of the disclosed approaches can be substituted for or used to complement other of the disclosed approaches. Moreover, the present disclosure can be used throughout the body but have clear applications to articulating body structures such as joints.

Thus, it will be apparent from the foregoing that, while particular forms of the invention have been illustrated and described, various modifications can be made without parting from the spirit and scope of the present disclosure.

We claim:

1. A method of implanting an extra-articular medical device at an interventional site of a patient, comprising:

implanting a first component at the interventional site on a medial or lateral side of an articulating knee joint;
   implanting a second component at the interventional site;
   inserting a temporary component at the interventional site between the first and second components;
   assessing kinematic characteristics including desired energy absorption for load bypassing support for a link component carrying load in compression; and removing the temporary component from the interventional site.

2. The method of claim 1, wherein implanting a first component and implanting a second component includes affixing the first and second components within the interventional site.

3. The method of claim 1, wherein the patient is placed in a lateral decubitus position.

4. The method of claim 3, wherein legs of the patient are secured in place with an upper leg in flexion and a lower leg in extension.

5. The method of claim 1, further comprising attaching the link component to each of the first and second components, wherein the link component is implanted subcutaneous and extra-capsular.

6. The method of claim 5, wherein the link component spans an articulating joint.

7. The method of claim 5, further comprising implanting the link component subcutaneous and extra-capsular.

* * * * *